(12) United States Patent
Nelson et al.

(10) Patent No.: US 11,607,148 B2
(45) Date of Patent: Mar. 21, 2023

(54) METHODS AND APPARATUS FOR PATIENT POSITIONING IN MAGNETIC RESONANCE IMAGING

(71) Applicant: Hyperfine Operations, Inc., Guilford, CT (US)

(72) Inventors: Anne Michele Nelson, Guilford, CT (US); Christopher Thomas McNulty, Guilford, CT (US); Jeremy Christopher Jordan, Cromwell, CT (US); Michael Stephen Poole, Guilford, CT (US); Gang Chen, Guilford, CT (US)

(73) Assignee: Hyperfine Operations, Inc., Guilford, CT (US)

( * ) Notice: Subject to any disclaimer, the term of this patent is extended or adjusted under 35 U.S.C. 154(b) by 0 days.

(21) Appl. No.: 17/551,996

(22) Filed: Dec. 15, 2021

(65) Prior Publication Data

US 2022/0104722 A1 Apr. 7, 2022

Related U.S. Application Data

(63) Continuation of application No. 16/516,373, filed on Jul. 19, 2019, now Pat. No. 11,234,610.
(Continued)

(51) Int. Cl.
*G01R 33/34* (2006.01)
*A61B 5/055* (2006.01)
(Continued)

(52) U.S. Cl.
CPC .............. *A61B 5/055* (2013.01); *A61B 90/14* (2016.02); *G01R 33/307* (2013.01);
(Continued)

(58) Field of Classification Search
CPC ........... A61B 5/055; A61B 90/14; A61B 5/70; A61B 6/04; A61B 5/0042; A61B 5/0046;
(Continued)

(56) References Cited

U.S. PATENT DOCUMENTS

| 4,771,785 A | 9/1988 | Duer |
| 4,882,560 A | 11/1989 | Young et al. |

(Continued)

FOREIGN PATENT DOCUMENTS

JP 2011-206230 A 10/2011

OTHER PUBLICATIONS

Invitation to Pay Additional Fees for International Application No. PCT/US2019/042585 dated Oct. 29, 2019.
(Continued)

*Primary Examiner* — G. M. A Hyder
(74) *Attorney, Agent, or Firm* — Wolf, Greenfield & Sacks, P.C.

(57) ABSTRACT

According to some aspects, a magnetic resonance imaging system capable of imaging a patient is provided. The magnetic resonance imaging system comprising at least one B0 magnet to produce a magnetic field to contribute to a B0 magnetic field for the magnetic resonance imaging system and a member configured to engage with a releasable securing mechanism of a radio frequency coil apparatus, the member attached to the magnetic resonance imaging system at a location so that, when the member is engaged with the releasable securing mechanism of the radio frequency coil apparatus, the radio frequency coil apparatus is secured to the magnetic resonance imaging system substantially within an imaging region of the magnetic resonance imaging system.

20 Claims, 40 Drawing Sheets

Related U.S. Application Data

(60) Provisional application No. 62/811,361, filed on Feb. 27, 2019, provisional application No. 62/700,711, filed on Jul. 19, 2018.

(51) Int. Cl.
| | |
|---|---|
| *G01R 33/30* | (2006.01) |
| *A61B 90/14* | (2016.01) |
| *G01R 33/483* | (2006.01) |
| *G01R 33/54* | (2006.01) |
| *A61B 5/00* | (2006.01) |
| *A61B 6/04* | (2006.01) |

(52) U.S. Cl.
CPC .......... *G01R 33/34007* (2013.01); *A61B 5/70* (2013.01); *A61B 6/04* (2013.01); *G01R 33/4833* (2013.01); *G01R 33/543* (2013.01)

(58) Field of Classification Search
CPC ............ G01R 33/307; G01R 33/34007; G01R 33/4833; G01R 33/543; G01R 33/34084; G01R 33/3802; G01R 33/3806; G01R 33/422; G01R 33/445; A61G 13/121
See application file for complete search history.

(56) References Cited

U.S. PATENT DOCUMENTS

| | | | |
|---|---|---|---|
| 5,083,105 A | 1/1992 | Herd et al. |
| 5,261,403 A | 11/1993 | Saito et al. |
| 5,361,764 A | 11/1994 | Reynolds et al. |
| 5,388,580 A | 2/1995 | Sullivan et al. |
| 5,952,830 A | 9/1999 | Petropoulos et al. |
| 6,037,773 A | 3/2000 | Mitsumata et al. |
| 6,317,618 B1 | 11/2001 | Livni et al. |
| 6,577,888 B1 | 6/2003 | Chan et al. |
| 6,591,128 B1 | 7/2003 | Wu et al. |
| 6,737,866 B2 | 5/2004 | Belt et al. |
| 7,046,008 B2 | 5/2006 | Okamoto et al. |
| 7,382,132 B1 | 6/2008 | Matthew et al. |
| 7,474,095 B2 | 1/2009 | Levitt et al. |
| 7,906,966 B1 | 3/2011 | Votruba |
| 8,188,740 B2 | 5/2012 | Ninomiya et al. |
| 8,294,460 B2 | 10/2012 | Driemel |
| 8,638,100 B2 | 1/2014 | Driemel |
| 9,134,389 B2 | 9/2015 | Driemel |
| 9,285,440 B2 | 3/2016 | Driemel |
| 9,364,293 B2 | 7/2016 | Shalgi et al. |
| 9,386,940 B2 | 7/2016 | Friman |
| 9,541,616 B2 | 1/2017 | Rothberg et al. |
| 9,547,057 B2 | 1/2017 | Rearick et al. |
| 9,625,543 B2 | 4/2017 | Rearick et al. |
| 9,625,544 B2 | 4/2017 | Poole et al. |
| 9,638,773 B2 | 5/2017 | Poole et al. |
| 9,645,210 B2 | 5/2017 | McNulty et al. |
| 9,797,971 B2 | 10/2017 | Rearick et al. |
| 9,817,093 B2 | 11/2017 | Rothberg et al. |
| 9,835,702 B2 | 12/2017 | Takami et al. |
| 9,841,473 B2 | 12/2017 | Driemel |
| 10,139,464 B2 | 11/2018 | Rearick et al. |
| 10,145,913 B2 | 12/2018 | Hugon et al. |
| 10,145,922 B2 | 12/2018 | Rothberg et al. |
| 10,222,434 B2 | 3/2019 | Poole et al. |
| 10,222,435 B2 | 3/2019 | Mileski et al. |
| 10,241,177 B2 | 3/2019 | Poole et al. |
| 10,274,561 B2 | 4/2019 | Poole et al. |
| 10,281,540 B2 | 5/2019 | Mileski et al. |
| 10,281,541 B2 | 5/2019 | Poole et al. |
| 10,295,628 B2 | 5/2019 | Mileski et al. |
| 10,310,037 B2 | 6/2019 | McNulty et al. |
| 10,324,147 B2 | 6/2019 | McNulty et al. |
| 10,330,755 B2 | 6/2019 | Poole et al. |
| 10,353,030 B2 | 7/2019 | Poole et al. |
| 10,371,773 B2 | 8/2019 | Poole et al. |
| 10,379,186 B2 | 8/2019 | Rothberg et al. |
| 10,416,264 B2 | 9/2019 | Sofka et al. |
| 10,444,310 B2 | 10/2019 | Poole et al. |
| 10,466,327 B2 | 11/2019 | Rothberg et al. |
| 10,488,482 B2 | 11/2019 | Rearick et al. |
| 10,495,712 B2 | 12/2019 | Rothberg et al. |
| 10,520,566 B2 | 12/2019 | Poole et al. |
| 10,551,452 B2 | 2/2020 | Rearick et al. |
| 10,591,561 B2 | 3/2020 | Sacolick et al. |
| 10,709,387 B2 | 7/2020 | Poole et al. |
| 11,006,851 B2 | 5/2021 | Nelson et al. |
| 11,234,610 B2 | 2/2022 | Nelson et al. |
| 11,298,042 B2 | 4/2022 | Nelson et al. |
| 11,357,420 B2 | 6/2022 | Nelson et al. |
| 2002/0077539 A1 | 6/2002 | Schmit et al. |
| 2004/0030241 A1 | 2/2004 | Green et al. |
| 2005/0054910 A1 | 3/2005 | Tremblay et al. |
| 2005/0228267 A1 | 10/2005 | Bulkes et al. |
| 2007/0035301 A1 | 2/2007 | Nakabayashi et al. |
| 2007/0191706 A1 | 8/2007 | Calderon et al. |
| 2007/0255132 A1 | 11/2007 | Shalgi et al. |
| 2008/0275333 A1 | 11/2008 | Fain et al. |
| 2009/0216110 A1 | 8/2009 | Piron et al. |
| 2010/0271026 A1 | 10/2010 | Amm et al. |
| 2011/0031970 A1 | 2/2011 | Ninomiya et al. |
| 2011/0037470 A1 | 2/2011 | Driemel et al. |
| 2011/0040174 A1 | 2/2011 | Driemel |
| 2012/0119739 A1 | 5/2012 | Gleich |
| 2012/0126815 A1 | 5/2012 | Hahn |
| 2013/0154636 A1 | 6/2013 | Takami et al. |
| 2014/0039301 A1 | 2/2014 | Driemel |
| 2015/0022201 A1 | 1/2015 | Han et al. |
| 2015/0087966 A1 | 3/2015 | Anderson et al. |
| 2015/0102813 A1 | 4/2015 | Dumoulin et al. |
| 2016/0054404 A1 | 2/2016 | Duensing et al. |
| 2016/0069968 A1 | 3/2016 | Rothberg et al. |
| 2016/0069970 A1 | 3/2016 | Rearick et al. |
| 2016/0069971 A1 | 3/2016 | McNulty et al. |
| 2016/0069972 A1 | 3/2016 | Poole et al. |
| 2016/0069975 A1 | 3/2016 | Rothberg et al. |
| 2016/0077172 A1 | 3/2016 | Duesing et al. |
| 2016/0081582 A1 | 3/2016 | Rapoport |
| 2016/0089055 A1 | 3/2016 | Rapoport |
| 2016/0128592 A1 | 5/2016 | Rosen et al. |
| 2016/0131727 A1 | 5/2016 | Sacolick et al. |
| 2016/0169992 A1 | 6/2016 | Rothberg et al. |
| 2016/0169993 A1 | 6/2016 | Rearick et al. |
| 2016/0195594 A1 | 7/2016 | Leussler et al. |
| 2016/0209482 A1 | 7/2016 | Hwang et al. |
| 2016/0223631 A1 | 8/2016 | Poole et al. |
| 2016/0231399 A1 | 8/2016 | Rothberg et al. |
| 2016/0231402 A1 | 8/2016 | Rothberg et al. |
| 2016/0231403 A1 | 8/2016 | Rothberg et al. |
| 2016/0231404 A1 | 8/2016 | Rothberg et al. |
| 2016/0299203 A1 | 10/2016 | Mileski et al. |
| 2016/0334479 A1 | 11/2016 | Poole et al. |
| 2017/0102443 A1 | 4/2017 | Rearick et al. |
| 2017/0153303 A1 | 6/2017 | Tomiha et al. |
| 2017/0227616 A1 | 8/2017 | Poole et al. |
| 2017/0276747 A1 | 9/2017 | Hugon et al. |
| 2017/0276749 A1 | 9/2017 | Hugon et al. |
| 2018/0024208 A1 | 1/2018 | Rothberg et al. |
| 2018/0038931 A1 | 2/2018 | Rearick et al. |
| 2018/0088193 A1 | 3/2018 | Rearick et al. |
| 2018/0143274 A1 | 5/2018 | Poole et al. |
| 2018/0143275 A1 | 5/2018 | Sofka et al. |
| 2018/0143280 A1 | 5/2018 | Dyvorne et al. |
| 2018/0143281 A1 | 5/2018 | Sofka et al. |
| 2018/0144467 A1 | 5/2018 | Sofka et al. |
| 2018/0156881 A1 | 6/2018 | Poole et al. |
| 2018/0164390 A1 | 6/2018 | Poole et al. |
| 2018/0168527 A1 | 6/2018 | Poole et al. |
| 2018/0210047 A1 | 7/2018 | Poole et al. |
| 2018/0224512 A1 | 8/2018 | Poole et al. |
| 2018/0238978 A1 | 8/2018 | McNulty et al. |
| 2018/0238980 A1 | 8/2018 | Poole et al. |
| 2018/0238981 A1 | 8/2018 | Poole et al. |
| 2019/0004130 A1 | 1/2019 | Poole et al. |
| 2019/0011510 A1 | 1/2019 | Hugon et al. |

(56) References Cited

U.S. PATENT DOCUMENTS

| | | |
|---|---|---|
| 2019/0011513 A1 | 1/2019 | Poole et al. |
| 2019/0011514 A1 | 1/2019 | Poole et al. |
| 2019/0011521 A1 | 1/2019 | Sofka et al. |
| 2019/0018094 A1 | 1/2019 | Mileski et al. |
| 2019/0018095 A1 | 1/2019 | Mileski et al. |
| 2019/0018096 A1 | 1/2019 | Poole et al. |
| 2019/0025389 A1 | 1/2019 | McNulty et al. |
| 2019/0033402 A1 | 1/2019 | McNulty et al. |
| 2019/0033414 A1 | 1/2019 | Sofka et al. |
| 2019/0033415 A1 | 1/2019 | Sofka et al. |
| 2019/0033416 A1 | 1/2019 | Rothberg et al. |
| 2019/0038233 A1 | 2/2019 | Poole et al. |
| 2019/0086497 A1 | 3/2019 | Rearick et al. |
| 2019/0101607 A1 | 4/2019 | Rothberg et al. |
| 2019/0154775 A1 | 5/2019 | Stack et al. |
| 2019/0162806 A1 | 5/2019 | Poole et al. |
| 2019/0170838 A1 | 6/2019 | George |
| 2019/0178962 A1 | 6/2019 | Poole et al. |
| 2019/0178963 A1 | 6/2019 | Poole et al. |
| 2019/0227136 A1 | 7/2019 | Mileski et al. |
| 2019/0227137 A1 | 7/2019 | Mileski et al. |
| 2019/0250227 A1 | 8/2019 | McNulty et al. |
| 2019/0250228 A1 | 8/2019 | McNulty et al. |
| 2019/0257903 A1 | 8/2019 | Poole et al. |
| 2019/0277927 A1 | 9/2019 | Stickle et al. |
| 2019/0324098 A1 | 10/2019 | McNulty et al. |
| 2019/0353720 A1 | 11/2019 | Dyvorne et al. |
| 2019/0353723 A1 | 11/2019 | Dyvorne et al. |
| 2019/0353726 A1 | 11/2019 | Poole et al. |
| 2019/0353727 A1 | 11/2019 | Dyvorne et al. |
| 2020/0022611 A1 | 1/2020 | Nelson et al. |
| 2020/0022612 A1 | 1/2020 | McNulty et al. |
| 2020/0022613 A1 | 1/2020 | Nelson et al. |
| 2020/0025846 A1 | 1/2020 | Nelson et al. |
| 2020/0034998 A1 | 1/2020 | Schlemper et al. |
| 2020/0041588 A1 | 2/2020 | O'Halloran et al. |
| 2020/0045112 A1 | 2/2020 | Sacolick et al. |
| 2020/0054241 A1 | 2/2020 | Nelson et al. |
| 2020/0058106 A1 | 2/2020 | Lazarus et al. |
| 2020/0200844 A1 | 6/2020 | Boskamp et al. |
| 2020/0209334 A1 | 7/2020 | O'Halloran et al. |
| 2020/0289019 A1 | 9/2020 | Schlemper et al. |
| 2020/0289022 A1 | 9/2020 | Coumans et al. |
| 2020/0294229 A1 | 9/2020 | Schlemper et al. |
| 2020/0294282 A1 | 9/2020 | Schlemper et al. |
| 2020/0294287 A1 | 9/2020 | Schlemper et al. |
| 2020/0355765 A1 | 11/2020 | Chen et al. |
| 2021/0244306 A1 | 8/2021 | Nelson et al. |

OTHER PUBLICATIONS

International Search Report and Written Opinion for International Application No. PCT/US2019/042585 dated Jan. 2, 2020.
International Preliminary Report on Patentability for International Application No. PCT/US2019/042585 dated Jan. 28, 2021.

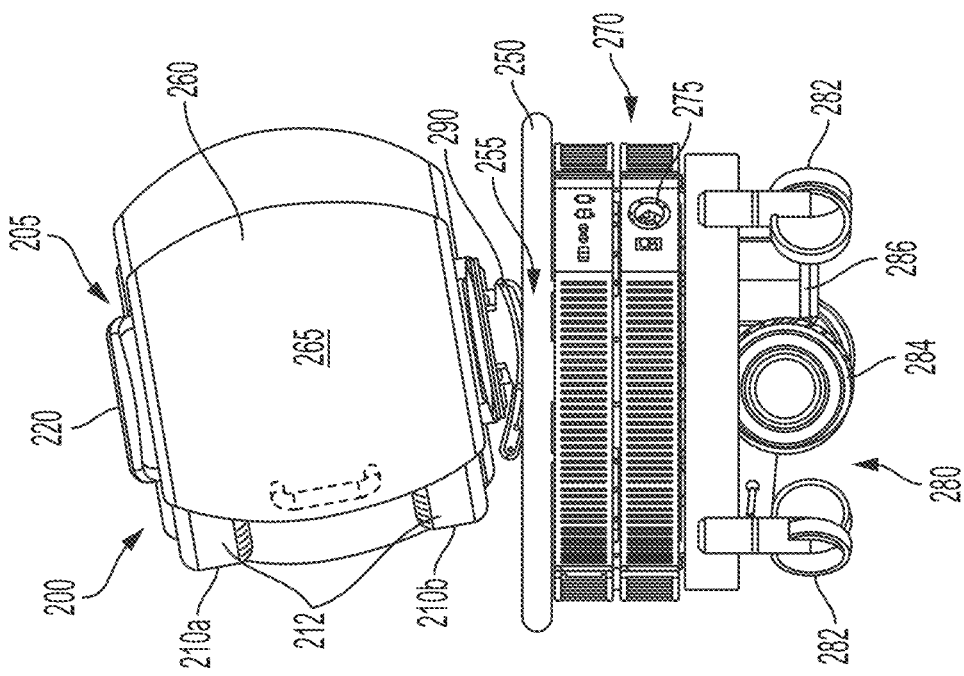
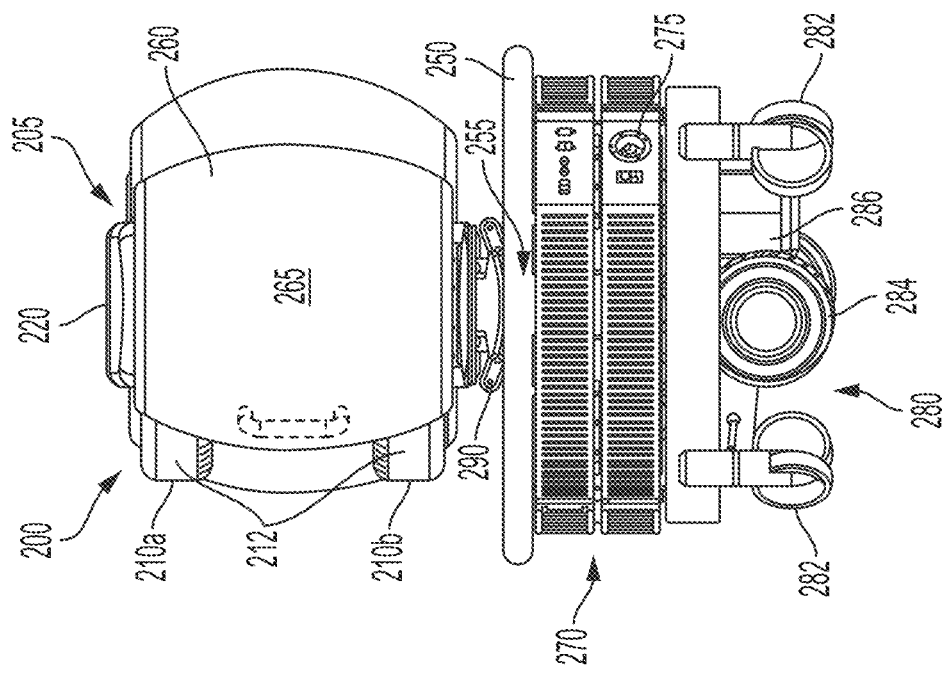
FIG. 2B
FIG. 2A

METHODS AND APPARATUS FOR PATIENT POSITIONING IN MAGNETIC RESONANCE IMAGING

CROSS REFERENCE TO RELATED APPLICATIONS

This application claims priority under 35 U.S.C. § 120 and is a continuation application of U.S. patent application Ser. No. 16/516,373, filed Jul. 19, 2019 and titled "Methods and Apparatus for Patient Positioning in Magnetic Resonance Imaging," which claims priority under 35 U.S.C. § 119 to U.S. Provisional Application Ser. No. 62/700,711 filed Jul. 19, 2018 and titled "Methods and Apparatus for Patient Positioning in Magnetic Resonance Imaging," and U.S. Provisional Application Ser. No. 62/811,361 filed Feb. 27, 2019 and titled "Methods and Apparatus for Patient Positioning in Magnetic Resonance Imaging," each application of which is herein incorporated by reference in its entirety.

BACKGROUND

Magnetic resonance imaging (MRI) provides an important imaging modality for numerous applications and is widely utilized in clinical and research settings to produce images of the inside of the human body. As a generality, MRI is based on detecting magnetic resonance (MR) signals, which are electromagnetic waves emitted by atoms in response to state changes resulting from applied electromagnetic fields. For example, nuclear magnetic resonance (NMR) techniques involve detecting MR signals emitted from the nuclei of excited atoms upon the re-alignment or relaxation of the nuclear spin of atoms in an object being imaged (e.g., atoms in the tissue of the human body). Detected MR signals may be processed to produce images, which in the context of medical applications, allows for the investigation of internal structures and/or biological processes within the body for diagnostic, therapeutic and/or research purposes.

MRI provides an attractive imaging modality for biological imaging due to the ability to produce non-invasive images having relatively high resolution and contrast without the safety concerns of other modalities (e.g., without needing to expose the subject to ionizing radiation, e.g., x-rays, or introducing radioactive material to the body). Additionally, MRI is particularly well suited to provide soft tissue contrast, which can be exploited to image subject matter that other imaging modalities are incapable of satisfactorily imaging. Moreover, MR techniques are capable of capturing information about structures and/or biological processes that other modalities are incapable of acquiring. However, there are a number of drawbacks to MRI that, for a given imaging application, may involve the relatively high cost of the equipment, limited availability and/or difficulty in gaining access to clinical MRI scanners and/or the length of the image acquisition process.

The trend in clinical MRI has been to increase the field strength of MRI scanners to improve one or more of scan time, image resolution, and image contrast, which, in turn, continues to drive up costs. The vast majority of installed MRI scanners operate at 1.5 or 3 tesla (T), which refers to the field strength of the main magnetic field $B_0$. A rough cost estimate for a clinical MRI scanner is approximately one million dollars per tesla, which does not factor in the substantial operation, service, and maintenance costs involved in operating such MRI scanners.

Additionally, conventional high-field MRI systems typically require large superconducting magnets and associated electronics to generate a strong uniform static magnetic field ($B_0$) in which an object (e.g., a patient) is imaged. The size of such systems is considerable with a typical MRI installment including multiple rooms for the magnet, electronics, thermal management system, and control console areas. The size and expense of MRI systems generally limits their usage to facilities, such as hospitals and academic research centers, which have sufficient space and resources to purchase and maintain them. The high cost and substantial space requirements of high-field MRI systems results in limited availability of MRI scanners. As such, there are frequently clinical situations in which an MRI scan would be beneficial, but due to one or more of the limitations discussed above, is not practical or is impossible, as discussed in further detail below.

SUMMARY

Some embodiments include a patient handling apparatus configured to facilitate positioning a patient within a magnetic resonance imaging device, the patient handling apparatus comprising a patient support having a surface adapted to be positioned between the patient and a bed so that, when positioned, the surface of the patient support is underneath at least a portion of the patient's body, and a securing portion comprising at least one first releasable securing mechanism configured to engage with a radio frequency component to secure the radio frequency component to the securing portion, and at least one second releasable securing mechanism configured to engage with the magnetic resonance imaging device to secure the securing portion to the magnetic resonance imaging device.

Some embodiment include a helmet configured to accommodate a patient's head during magnetic resonance imaging, the helmet comprising at least one radio frequency transmit and/or receive coil, and at least one first releasable securing mechanism configured to engage with a member attached to a magnetic resonance imaging system at a location such that, when the at least one securing mechanism engages with the member, the helmet is positioned within the imaging region of the magnetic resonance imaging system.

Some embodiments include a helmet configured to accommodate a patient's head during magnetic resonance imaging, the helmet comprising at least one radio frequency transmit and/or receive coil, at least one first releasable securing mechanism configured to engage with a member of the magnetic resonance imaging system such that, when the at least one securing mechanism engages with the member, the at least one securing mechanism resists translation of the helmet relative to the cooperating member, and at least one second securing mechanism configured to, when engaged with a cooperating portion of the member, prevent rotation of the helmet about the member.

Some embodiments include a magnetic resonance imaging system capable of imaging a patient at least partially supported by a support comprising ferromagnetic material, the magnetic resonance imaging system comprising at least one first $B_0$ magnet to produce a first magnetic field to contribute to a $B_0$ magnetic field for the magnetic resonance imaging system, the $B_0$ magnetic field having a field strength of less than or equal to 0.2 T, at least one second $B_0$ magnet to produce a second magnetic field to contribute to the $B_0$ magnetic field for the magnetic resonance imaging system, wherein the at least one first $B_0$ magnet and the at least one second $B_0$ magnet are arranged relative to one another so that an imaging region is provided there between, and a member configured to engage with a releasable securing mechanism of a radio frequency coil apparatus, the member attached to the magnetic resonance imaging between the at least one first $B_0$ magnet and the at least one second $B_0$ magnet at a location so that, when the member is engaged with the releasable securing mechanism of the radio frequency coil apparatus, the radio frequency coil apparatus is secured to the magnetic resonance imaging system substantially within the imaging region.

Some embodiments include a magnetic resonance imaging system capable of imaging a patient at least partially supported by a support comprising ferromagnetic material, the magnetic resonance imaging system comprising at least one first $B_0$ magnet to produce a first magnetic field to contribute to a $B_0$ magnetic field for the magnetic resonance imaging system, the $B_0$ magnetic field having a field strength of less than or equal to 0.2 T, at least one second $B_0$ magnet to produce a second magnetic field to contribute to the $B_0$ magnetic field for the magnetic resonance imaging system, wherein the at least one first $B_0$ magnet and the at least one second $B_0$ magnet are arranged relative to one another so that an imaging region is provided there between, and a member configured to engage with a releasable securing mechanism of a patient handling apparatus configured to secure a radio frequency coil apparatus, the member attached to the magnetic resonance imaging between the at least one first $B_0$ magnet and the at least one second $B_0$ magnet at a location so that, when the member is engaged with the releasable securing mechanism of the patient handling apparatus, the radio frequency coil secured to the patient handling apparatus is positioned substantially within the imaging region.

Some embodiments include a method, comprising releasably securing a support to a magnetic resonance imaging device so as to facilitate magnetic resonance imaging of a patient, the support disposed between the patient and a standard medical bed.

Some embodiments include a method comprising positioning a portion of anatomy of a patient within an imaging region of a magnetic resonance imaging system while the patient is at least partially supported by a standard medical bed, and acquiring at least one magnetic resonance image of the portion of the anatomy of the patient while the patient is at least partially supported by the standard medical bed.

Some embodiments include an apparatus for imaging a foot, the apparatus comprising at least one housing configured to accommodate a patient's foot during magnetic resonance imaging, at least one radio frequency transmit and/or receive coil, and at least one first releasable securing mechanism configured to engage with a member attached to a magnetic resonance imaging system at a location such that, when the at least one securing mechanism engages with the member, the apparatus is positioned within the imaging region of the magnetic resonance imaging system.

Some embodiments include an apparatus for imaging a foot, the apparatus comprising at least one radio frequency transmit and/or receive coil, and at least one housing configured to accommodate a patient's foot during magnetic resonance imaging, the at least one housing tilted at an angle relative to a vertical axis Some embodiments include a bridge adapted for attachment to a magnetic resonance imaging system and configured to facilitate positioning a patient within the magnetic resonance imaging system, the bridge comprising a support having a surface configured to support at least a portion of the patient, the support being moveable between an up position and a down position, wherein the surface is substantially vertical in the up position and substantially horizontal in the down position, a hinge configured to allow the support to be moved from the up position to the down position and vice versa, and a base configured to attach the bridge to the magnetic resonance imaging system.

Some embodiments include a magnetic resonance imaging system comprising a $B_0$ magnet configured to generate a magnetic field suitable for magnetic resonance imaging, a conveyance mechanism configured to allow the magnetic resonance imaging system to be moved to different locations, and a bridge configured to facilitate positioning a patient within the magnetic resonance imaging system, the bridge comprising a support having a surface configured to support at least a portion of the patient, the support being moveable between an up position and a down position, wherein the surface is substantially vertical in the up position and substantially horizontal in the down position, a hinge configured to allow the support to be moved from the up position to the down position and vice versa, and a base attaching the bridge to the magnetic resonance imaging system.

Some embodiments include a method of imaging a portion of anatomy of a patient while the patient is at least partially supported by a standard medical bed, the method comprising positioning a magnetic resonance imaging system and the bed proximate one another, moving a bridge attached to the magnetic resonance imaging system from a vertical position to a horizontal position so that the bridge overlaps a portion of the bed, positioning the patient via the bridge so that the portion of anatomy of the patient is within an imaging region of the magnetic resonance imaging system, and acquiring at least one magnetic resonance image of the portion of the anatomy of the patient while the patient is at least partially supported by the bed and at least partially supported by the bridge.

BRIEF DESCRIPTION OF THE DRAWINGS

Various aspects and embodiments of the disclosed technology will be described with reference to the following figures. It should be appreciated that the figures are not necessarily drawn to scale.

FIGS. 2A and 2B illustrate a portable low-field MRI system, in accordance with some embodiments.

DETAILED DESCRIPTION

Figure 1:
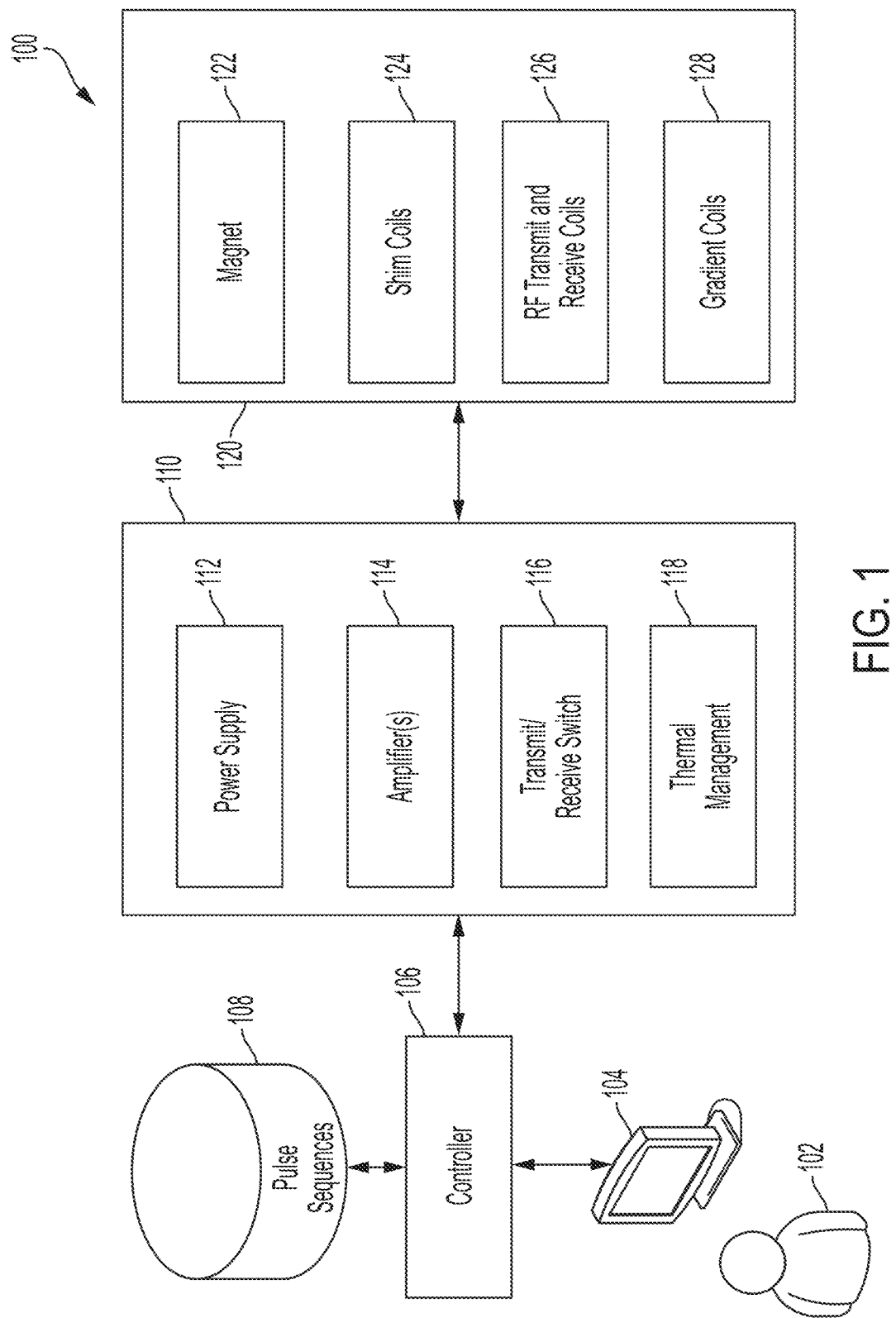
FIG. 1 illustrates exemplary components of a magnetic resonance imaging system.

The MRI scanner market is overwhelmingly dominated by high-field systems, and particularly for medical or clinical MRI applications. As discussed above, the general trend in medical imaging has been to produce MRI scanners with increasingly greater field strengths, with the vast majority of clinical MRI scanners operating at 1.5 T or 3 T, with higher field strengths of 7 T and 9 T used in research settings. As used herein, "high-field" refers generally to MRI systems presently in use in a clinical setting and, more particularly, to MRI systems operating with a main magnetic field (i.e., a $B_0$ field) at or above 1.5 T, though clinical systems operating between 0.5 T and 1.5 T are often also characterized as "high-field." Field strengths between approximately 0.2 T and 0.5 T have been characterized as "mid-field" and, as field strengths in the high-field regime have continued to increase, field strengths in the range between 0.5 T and 1 T have also been characterized as mid-field. By contrast, "low-field" refers generally to MRI systems operating with a $B_0$ field of less than or equal to approximately 0.2 T, though systems having a $B_0$ field of between 0.2 T and approximately 0.3 T have sometimes been characterized as low-field as a consequence of increased field strengths at the high end of the high-field regime. Within the low-field regime, low-field MRI systems operating with a $B_0$ field of less than 0.1 T are referred to herein as "very low-field" and low-field MRI systems operating with a $B_0$ field of less than 10 mT are referred to herein as "ultra-low field."

As discussed above, conventional MRI systems require specialized facilities. An electromagnetically shielded room is required for the MRI system to operate and the floor of the room must be structurally reinforced. Additional rooms must be provided for the high-power electronics and the scan technician's control area. Secure access to the site must also be provided. In addition, a dedicated three-phase electrical connection must be installed to provide the power for the electronics that, in turn, are cooled by a chilled water supply. Additional HVAC capacity typically must also be provided. These site requirements are not only costly, but significantly limit the locations where MRI systems can be deployed. Conventional clinical MRI scanners also require substantial expertise to both operate and maintain. These highly trained technicians and service engineers add large on-going operational costs to operating an MRI system. Conventional MRI, as a result, is frequently cost prohibitive and is severely limited in accessibility, preventing MRI from being a widely available diagnostic tool capable of delivering a wide range of clinical imaging solutions wherever and whenever needed. Typically, patient must visit one of a limited number of facilities at a time and place scheduled in advance, preventing MRI from being used in numerous medical applications for which it is uniquely efficacious in assisting with diagnosis, surgery, patient monitoring and the like.

As discussed above, high-field MRI systems require specially adapted facilities to accommodate the size, weight, power consumption and shielding requirements of these systems. For example, a 1.5 T MRI system typically weighs between 4-10 tons and a 3 T MRI system typically weighs between 8-20 tons. In addition, high-field MRI systems generally require significant amounts of heavy and expensive shielding. Many mid-field scanners are even heavier, weighing between 10-20 tons due, in part, to the use of very large permanent magnets and/or yokes. Commercially available low-field MRI systems (e.g., operating with a $B_0$ magnetic field of 0.2 T) are also typically in the range of 10 tons or more due to the large amounts of ferromagnetic material used to generate the $B_0$ field, with additional tonnage in shielding. To accommodate this heavy equipment, rooms (which typically have a minimum size of 30-50 square meters) have to be built with reinforced flooring (e.g., concrete flooring), and must be specially shielded to prevent electromagnetic radiation from interfering with operation of the MRI system. Thus, available clinical MRI systems are immobile and require the significant expense of a large, dedicated space within a hospital or facility, and in addition to the considerable costs of preparing the space for operation, require further additional on-going costs in expertise in operating and maintaining the system.

In addition, currently available MRI systems typically consume large amounts of power. For example, common 1.5 T and 3 T MRI systems typically consume between 20-40 kW of power during operation, while available 0.5 T and 0.2 T MRI systems commonly consume between 5-20 kW, each using dedicated and specialized power sources. Unless otherwise specified, power consumption is referenced as average power consumed over an interval of interest. For example, the 20-40 kW referred to above indicates the average power consumed by conventional MRI systems during the course of image acquisition, which may include relatively short periods of peak power consumption that significantly exceeds the average power consumption (e.g., when the gradient coils and/or RF coils are pulsed over relatively short periods of the pulse sequence). Intervals of peak (or large) power consumption are typically addressed via power storage elements (e.g., capacitors) of the MRI system itself. Thus, the average power consumption is the more relevant number as it generally determines the type of power connection needed to operate the device. As discussed above, available clinical MRI systems must have dedicated power sources, typically requiring a dedicated three-phase connection to the grid to power the components of the MRI system. Additional electronics are then needed to convert the three-phase power into single-phase power utilized by the MRI system. The many physical requirements of deploying conventional clinical MRI systems creates a significant problem of availability and severely restricts the clinical applications for which MRI can be utilized.

Accordingly, the many requirements of high-field MRI render installations prohibitive in many situations, limiting their deployment to large institutional hospitals or specialized facilities and generally restricting their use to tightly scheduled appointments, requiring the patient to visit dedicated facilities at times scheduled in advance. Thus, the many restrictions on high field MRI prevent MRI from being fully utilized as an imaging modality. Despite the drawbacks of high-field MRI mentioned above, the appeal of the significant increase in SNR at higher fields continues to drive the industry to higher and higher field strengths for use in clinical and medical MRI applications, further increasing the cost and complexity of MRI scanners, and further limiting their availability and preventing their use as a general-purpose and/or generally-available imaging solution.

The low SNR of MR signals produced in the low-field regime (particularly in the very low-field regime) has prevented the development of a relatively low cost, low power and/or portable MRI system. Conventional "low-field" MRI systems operate at the high end of what is typically characterized as the low-field range (e.g., clinically available low-field systems have a floor of approximately 0.2 T) to achieve useful images. Though somewhat less expensive than high-field MRI systems, conventional low-field MRI systems share many of the same drawbacks. In particular, conventional low-field MRI systems are large, fixed and immobile installments, consume substantial power (requiring dedicated three-phase power hook-ups) and require specially shielded rooms and large dedicated spaces. The challenges of low-field MRI have prevented the development of relatively low cost, low power and/or portable MRI systems that can produce useful images.

The inventors have developed techniques enabling portable, low-field, low power and/or lower-cost MRI systems that can improve the wide-scale deployability of MRI technology in a variety of environments beyond the current MRI installments at hospitals and research facilities. As a result, MRI can be deployed in emergency rooms, small clinics, doctor's offices, in mobile units, in the field, etc. and may be brought to the patient (e.g., bedside) to perform a wide variety of imaging procedures and protocols. Some embodiments include very low-field MRI systems (e.g., 0.1 T, 50 mT, 20 mT, etc.) that facilitate portable, low-cost, low-power MRI, significantly increasing the availability of MRI in a clinical setting.

There are numerous challenges to developing a clinical MRI system in the low-field regime. As used herein, the term clinical MRI system refers to an MRI system that produces clinically useful images, which refers to images having sufficient resolution and adequate acquisition times to be useful to a physician or clinician for its intended purpose given a particular imaging application. As such, the resolutions/acquisition times of clinically useful images will depend on the purpose for which the images are being obtained.

Among the numerous challenges in obtaining clinically useful images in the low-field regime is the relatively low SNR. Specifically, the relationship between SNR and $B_0$ field strength is approximately $B_0^{5/4}$ at field strength above 0.2 T and approximately $B_0^{3/2}$ at field strengths below 0.1 T. As such, the SNR drops substantially with decreases in field strength with even more significant drops in SNR experienced at very low field strength. This substantial drop in SNR resulting from reducing the field strength is a significant factor that has prevented development of clinical MRI systems in the very low-field regime. In particular, the challenge of the low SNR at very low field strengths has prevented the development of a clinical MRI system operating in the very low-field regime. As a result, clinical MRI systems that seek to operate at lower field strengths have conventionally achieved field strengths of approximately the 0.2 T range and above. These MRI systems are still large, heavy and costly, generally requiring fixed dedicated spaces (or shielded tents) and dedicated power sources.

The inventors have developed low-field and very low-field MRI systems capable of producing clinically useful images, allowing for the development of portable, low cost and easy to use MRI systems not achievable using state of the art technology. According to some embodiments, an MRI system can be transported to the patient to provide a wide variety of diagnostic, surgical, monitoring and/or therapeutic procedures, generally, whenever and wherever needed. There are challenges to providing an MRI system that can be transported to the patient and/or operated outside specialized facilities (e.g., outside secure and shielded rooms), a number of which are addressed using the techniques described in U.S. patent Ser. No. 10/222,434 (hereinafter, "the '434 patent"), titled "Portable Magnetic Resonance Imaging Methods and Apparatus," issued Mar. 5, 2019, which patent is herein incorporated by reference in its entirety.

Another challenge involves positioning the patient within the MRI system for imaging. As discussed above, conventional MRI is confined to specialized facilities, including a room for the device itself that is outfitted with extensive shielding and must meet stringent safety regulations, including requiring the room to be secure and free from ferrous material due to the high field strengths involved in conventional clinical MRI. Standard hospital beds are constructed using ferrous material, often steel, prohibiting there use with conventional clinical MRI systems. As a result, a patient must be brought to the specialized facility dedicated to the MRI system and transferred to a custom bed designed for use with the MRI system.

For patients that are ambulatory, this may mean requiring the patient to enter the secure room housing the MRI device and positioning themselves on a MRI-safe bed integrated with the MRI device. For patients that are not ambulatory or are otherwise immobilized, the patient may need to be first transferred to a customized MRI-safe bed to be transported to the secure room and then transferred to the integrated bed of the MRI system. Such requirements limit the circumstances in which a patient can undergo MRI and in some cases prohibits the use of MRI entirely. For example, transfer of non-ambulatory and/or immobile patients to an MRI safe bed or wheel chair to transport the patient into the secure room and, potentially, another transfer to the integrated bed or patient support of the MRI system is difficult and, in some circumstances, not feasible for medical safety reasons. Additionally, MRI safe beds are costly and not widely available.

The inventors have developed techniques that allow MRI to be performed in conjunction with a standard patient support, such as a standard hospital bed or standard wheelchair, thereby eliminating the requirement of transferring patients one or more times, as well eliminating costs and availability issues associated with specialized MRI safe transports (e.g., beds, wheelchairs, etc.). Additionally, techniques that allow MRI to be performed, for example, from a standard hospital bed, facilitate point-of-care MRI. According to some embodiments, MRI is performed at field strengths that are low enough to allow for imaging to be performed on a patient positioned on or in a standard patient support, for example, a patient lying on a standard hospital bed or seated in a standard wheelchair. As used herein, a standard hospital bed or standard wheelchair refers to a patient support that has not been outfitted for use with conventional high-field MRI. Standard hospital beds or wheelchairs will often be constructed of ferromagnetic material, such as steel, that prevents there use with high-field MRI.

To image a patient from, for example, a standard hospital bed, certain MRI imaging procedures may require positioning target anatomy of the patient within an MRI system moved to a location, for example, the bed on which the patient is currently lying. The inventors have developed techniques for facilitating the positioning of a patient within an MRI system for imaging of desired anatomy of the patient. According to some embodiments, a patient handling system that can be secured to the MRI system is used to support the patient and position the desired anatomy of the patient within the MRI system.

Conventional MRI systems typically include an integrated bed or support for the patient that is constructed using non-ferrous material to satisfy stringent regulatory requirements (e.g., regulations promulgated to ensure both patient and clinician safety) and so as to not disturb the magnetic fields produced by the MRI system. This customized MRI-safe bed is generally configured to be slid into and out of the bore of the system and typically has mounts that allow the appropriate radio frequency coil apparatus to be connected over the portion of the anatomy to be imaged. When preparing a patient for imaging, the patient is positioned on the bed outside the magnet bore so that the radio frequency coil apparatus can be positioned and attached to the cooperating mounts on the bed. For example, for a brain scan, a radio frequency head coil apparatus is positioned about the patient's head and attached to cooperating mounts fixed to the bed. After the radio frequency coil apparatus is attached and positioned correctly, the bed is moved inside the $B_0$ magnet so that the portion of the anatomy being imaged is positioned within the image region of the MRI system.

The inventors have recognized that this conventional process is not applicable to portable or point-of-care MRI, nor can this process be used to image a patient from a standard medical bed or wheelchair. For example, standard medical beds are not equipped with mounts to which a radio frequency coil apparatus can be attached, nor are radio frequency coil apparatus configured to be attached to standard medical beds. In addition, a standard medical bed or wheelchair cannot be positioned within the imaging region of an MRI system. To facilitate imaging from, for example, a standard medical bed, the inventors have developed radio frequency coil apparatus adapted to accommodate target anatomy of a patient and configured to engage with a cooperating member attached to the MRI system so that when the radio frequency coil apparatus is engaged with the member, the target anatomy is positioned within the imaging region of the MRI system. In this way, the radio frequency coil apparatus can be positioned about the patient and then attached to a portable MRI system so that the patient can be imaged from a standard medical bed or wheelchair, allowing the MRI system to be brought to the patient or the patient wheeled to an available MRI system and imaged from the standard medical bed. Such point-of-care MRI allows MRI to be utilized in a wide variety of medical situations where conventional MRI is not available (e.g., in the emergency room, intensive care unit, operating rooms, etc.).

According to some embodiments, a radio frequency helmet comprising one or more radio frequency coils is adapted to accommodate a patient's head. The radio frequency helmet comprises a releasable securing mechanism configured to secure the helmet to a member attached to the MRI system at a location so that whenever the radio frequency helmet is secured to the member, the helmet is substantially within the imaging region of the MRI system. In particular, when the helmet accommodates a patient's head and is secured to the member, the patient's head is positioned within the imaging region of the MRI system. According to some embodiments, a radio frequency coil apparatus comprising one or more radio frequency coils adapted to accommodate an appendage, such as a leg or an arm, is equipped with such a releasable securing mechanism so that when the radio frequency coil apparatus is secured to the member, the radio frequency coil apparatus is substantially within the imaging region of the MRI system so that the appendage positioned for imaging.

FIG. 1 is a block diagram of typical components of a MRI system 100. In the illustrative example of FIG. 1, MRI system 100 comprises computing device 104, controller 106, pulse sequences store 108, power management system 110, and magnetics components 120. It should be appreciated that system 100 is illustrative and that a MRI system may have one or more other components of any suitable type in addition to or instead of the components illustrated in FIG. 1. However, a MRI system will generally include these high level components, though the implementation of these components for a particular MRI system may differ vastly, as discussed in further detail below.

As illustrated in FIG. 1, magnetics components 120 comprise $B_0$ magnet 122, shim coils 124, RF transmit and receive coils 126, and gradient coils 128. Magnet 122 may be used to generate the main magnetic field $B_0$. Magnet 122 may be any suitable type or combination of magnetics components that can generate a desired main magnetic $B_0$ field. As discussed above, in the high field regime, the $B_0$ magnet is typically formed using superconducting material generally provided in a solenoid geometry, requiring cryogenic cooling systems to keep the $B_0$ magnet in a superconducting state. Thus, high-field $B_0$ magnets are expensive, complicated and consume large amounts of power (e.g., cryogenic cooling systems require significant power to maintain the extremely low temperatures needed to keep the $B_0$ magnet in a superconducting state), require large dedicated spaces, and specialized, dedicated power connections (e.g., a dedicated three-phase power connection to the power grid). Conventional low-field $B_0$ magnets (e.g., $B_0$ magnets operating at 0.2 T) are also often implemented using superconducting material and therefore have these same general requirements. Other conventional low-field $B_0$ magnets are implemented using permanent magnets, which to produce the field strengths to which conventional low-field systems are limited (e.g., between 0.2 T and 0.3 T due to the inability to acquire useful images at lower field strengths), need to be very large magnets weighing 5-20 tons. Thus, the $B_0$ magnet of conventional MRI systems alone prevents both portability and affordability.

Gradient coils 128 may be arranged to provide gradient fields and, for example, may be arranged to generate gradients in the $B_0$ field in three substantially orthogonal directions (X, Y, Z). Gradient coils 128 may be configured to encode emitted MR signals by systematically varying the $B_0$ field (the $B_0$ field generated by magnet 122 and/or shim coils 124) to encode the spatial location of received MR signals as a function of frequency or phase. For example, gradient coils 128 may be configured to vary frequency or phase as a linear function of spatial location along a particular direction, although more complex spatial encoding profiles may also be provided by using nonlinear gradient coils. For example, a first gradient coil may be configured to selectively vary the $B_0$ field in a first (X) direction to perform frequency encoding in that direction, a second gradient coil may be configured to selectively vary the $B_0$ field in a second (Y) direction substantially orthogonal to the first direction to perform phase encoding, and a third gradient coil may be configured to selectively vary the $B_0$ field in a third (Z) direction substantially orthogonal to the first and second directions to enable slice selection for volumetric imaging applications. As discussed above, conventional gradient coils also consume significant power, typically operated by large, expensive gradient power sources, as discussed in further detail below.

MRI is performed by exciting and detecting emitted MR signals using transmit and receive coils, respectively (often referred to as radio frequency (RF) coils). Transmit/receive coils may include separate coils for transmitting and receiving, multiple coils for transmitting and/or receiving, or the same coils for transmitting and receiving. Thus, a transmit/receive component may include one or more coils for transmitting, one or more coils for receiving and/or one or more coils for transmitting and receiving. Transmit/receive coils are also often referred to as Tx/Rx or Tx/Rx coils to generically refer to the various configurations for the transmit and receive magnetics component of an MRI system. These terms are used interchangeably herein. In FIG. 1, RF transmit and receive coils 126 comprise one or more transmit coils that may be used to generate RF pulses to induce an oscillating magnetic field Bi. The transmit coil(s) may be configured to generate any suitable types of RF pulses.

Power management system 110 includes electronics to provide operating power to one or more components of the low-field MRI system 100. For example, as discussed in more detail below, power management system 110 may include one or more power supplies, gradient power components, transmit coil components, and/or any other suitable power electronics needed to provide suitable operating power to energize and operate components of MRI system 100. As illustrated in FIG. 1, power management system 110 comprises power supply 112, power component(s) 114, transmit/receive switch 116, and thermal management components 118 (e.g., cryogenic cooling equipment for superconducting magnets). Power supply 112 includes electronics to provide operating power to magnetic components 120 of the MRI system 100. For example, power supply 112 may include electronics to provide operating power to one or more $B_0$ coils (e.g., $B_0$ magnet 122) to produce the main magnetic field for the low-field MRI system. Transmit/receive switch 116 may be used to select whether RF transmit coils or RF receive coils are being operated.

Power component(s) 114 may include one or more RF receive (Rx) pre-amplifiers that amplify MR signals detected by one or more RF receive coils (e.g., coils 126), one or more RF transmit (Tx) power components configured to provide power to one or more RF transmit coils (e.g., coils 126), one or more gradient power components configured to provide power to one or more gradient coils (e.g., gradient coils 128), and one or more shim power components configured to provide power to one or more shim coils (e.g., shim coils 124).

In conventional MRI systems, the power components are large, expensive and consume significant power. Typically, the power electronics occupy a room separate from the MRI scanner itself. The power electronics not only require substantial space, but are expensive complex devices that consume substantial power and require wall mounted racks to be supported. Thus, the power electronics of conventional MRI systems also prevent portability and affordability of MRI.

As illustrated in FIG. 1, MRI system 100 includes controller 106 (also referred to as a console) having control electronics to send instructions to and receive information from power management system 110. Controller 106 may be configured to implement one or more pulse sequences, which are used to determine the instructions sent to power management system 110 to operate the magnetic components 120 in a desired sequence (e.g., parameters for operating the RF transmit and receive coils 126, parameters for operating gradient coils 128, etc.). As illustrated in FIG. 1, controller 106 also interacts with computing device 104 programmed to process received MR data. For example, computing device 104 may process received MR data to generate one or more MR images using any suitable image reconstruction process(es). Controller 106 may provide information about one or more pulse sequences to computing device 104 for the processing of data by the computing device. For example, controller 106 may provide information about one or more pulse sequences to computing device 104 and the computing device may perform an image reconstruction process based, at least in part, on the provided information. In conventional MRI systems, computing device 104 typically includes one or more high performance work-stations configured to perform computationally expensive processing on MR data relatively rapidly. Such computing devices are relatively expensive equipment on their own.

As should be appreciated from the foregoing, currently available clinical MRI systems (including high-field, midfield and low-field systems) are large, expensive, fixed installations requiring substantial dedicated and specially designed spaces, as well as dedicated power connections. As discussed above, the inventors have developed low power, portable low-field MRI systems that can be deployed in virtually any environment and that can be brought to the patient who will undergo an imaging procedure. In this way, patients in emergency rooms, intensive care units, operating rooms and a host of other locations can benefit from MRI in circumstances where MRI is conventionally unavailable. The exemplary portable MRI systems described below in connection with FIGS. 2A, 2B and 3A are capable of being moved to locations at which MRI is needed (e.g., emergency and operating rooms, primary care offices, neonatal units, intensive care units, specialty departments, hospital rooms, recovery units, etc.), facilitating point-of-care MRI operable in proximity to standard hospital equipment such as hospital beds, wheelchairs, other medical devices, computing equipment, life support systems, etc. Additionally, the exemplary portable MRI systems described herein, including the systems described in the '434 patent, allow for the deployment of the MRI system in virtually any location so that a patient can be easily brought to the MRI system (e.g., transported using a standard hospital bed or wheelchair) to achieve point-of-care MRI.

FIGS. 2A and 2B illustrate a low power, portable low-field MRI system, in accordance with some embodiments. Portable MRI system 200 comprises a $B_0$ magnet 205 including at least one first permanent magnet 210a and at least one second permanent magnet 210b magnetically coupled to one another by a ferromagnetic yoke 220 configured to capture and channel magnetic flux to increase the magnetic flux density within the imaging region (field of view) of the MRI system. Permanent magnets 210a and 210b may be constructed using any suitable technique, (e.g., using any of the techniques, designs and/or materials described in the '434 patent). Yoke 220 may also be constructed using any of the techniques described herein (e.g., using any of the techniques, designs and/or materials described in the '434 patent). It should be appreciated that, in some embodiments, $B_0$ magnet 205 may be formed using electromagnets using any of the electromagnet techniques described herein (e.g., using any of the techniques, designs and/or materials described in the '434 patent). $B_0$ magnet 205 may be encased or enclosed in a housing 212 along with one or more other magnetics components, such as the system's gradient coils (e.g., x-gradient, y-gradient and z-gradient coils) and/or any shim components (e.g., shim coils or permanent magnetic shims), $B_0$ correction coils, etc.

$B_0$ magnet 205 may be coupled to or otherwise attached or mounted to base 250 by a positioning mechanism 290, such as a goniometric stage (examples of which are described in the '434 patent), so that the $B_0$ magnet can be tilted (e.g., rotated about its center of mass) to provide an incline to accommodate a patient's anatomy as needed. In FIG. 2A, the $B_0$ magnet is shown level without an incline and, in FIG. 2B, the $B_0$ magnet is shown after undergoing a rotation to incline the surface supporting the patient's anatomy being scanned. Positioning mechanism 290 may be fixed to one or more load bearing structures of base 250 arranged to support the weight of $B_0$ magnet 205.

In addition to providing the load bearing structures for supporting the $B_0$ magnet, base 250 also includes an interior space configured to house the electronics 270 needed to operate the portable MRI system 200. For example, base 250 may house the power components to operate the gradient coils (e.g., X, Y and Z) and the RF transmit/receive coils. The inventors have developed generally low power, low noise and low cost gradient amplifiers configured to suitably power gradient coils in the low-field regime, designed to be relatively low cost, and constructed for mounting within the base of the portable MRI system (i.e., instead of being statically racked in a separate room of a fixed installment as is conventionally done). Examples of suitable power components to operate the gradient coils are described in further detail below (e.g., the power components described in connection with FIGS. 20-34). According to some embodiments, the power electronics for powering the gradient coils of an MRI system consume less than 50 W when the system is idle and between 100-300 W when the MRI system is operating (i.e., during image acquisition). Base 250 may also house the RF coil amplifiers (i.e., power amplifiers to operate the transmit/receive coils of the system), power supplies, console, power distribution unit and other electronics needed to operate the MRI system, further details of which are described below.

According to some embodiments, the electronics 270 needed to operate portable MRI system 200 consume less than 1 kW of power, in some embodiments, less than 750 W of power and, in some embodiments, less than 500 W of power (e.g., MRI systems utilizing a permanent $B_0$ magnet solution). Techniques for facilitating low power operation of an MRI device are discussed in further detail below. However, systems that consume greater power may also be utilized as well, as the aspects are not limited in this respect. Exemplary portable MRI system 200 illustrated in FIGS. 2A and 2B may be powered via a single power connection 275 configured to connect to a source of mains electricity, such as an outlet providing single-phase power (e.g., a standard or large appliance outlet). Accordingly, the portable MRI system can be plugged into a single available power outlet and operated therefrom, eliminating the need for a dedicated power source (e.g., eliminating the need for a dedicated three-phase power source as well as eliminating the need for further power conversion electronics to convert three phase power to single phase power to be distributed to corresponding components of the MRI system) and increasing the availability of the MRI system and the circumstances and locations in which the portable MRI system may be used.

Portable MRI system 200 illustrated in FIGS. 2A and 2B also comprises a conveyance mechanism 280 that allows the portable MRI system to be transported to different locations. The conveyance mechanism may comprise one or more components configured to facilitate movement of the portable MRI system, for example, to a location at which MRI is needed. According to some embodiments, conveyance mechanism comprises a motor 286 coupled to drive wheels 284. In this manner, conveyance mechanism 280 provides motorized assistance in transporting MRI system 200 to desired locations. Conveyance mechanism 280 may also include a plurality of castors 282 to assist with support and stability as well as facilitating transport.

According to some embodiments, conveyance mechanism 280 includes motorized assistance controlled using a controller (e.g., a joystick or other controller that can be manipulated by a person) to guide the portable MRI system during transportation to desired locations. According to some embodiments, the conveyance mechanism comprises power assist means configured to detect when force is applied to the MRI system and to, in response, engage the conveyance mechanism to provide motorized assistance in the direction of the detected force. For example, rail 255 of base 250 illustrated in FIGS. 2A and 2B may be configured to detect when force is applied to the rail (e.g., by personnel pushing on the rail) and engage the conveyance mechanism to provide motorized assistance to drive the wheels in the direction of the applied force. As a result, a user can guide the portable MRI system with the assistance of the conveyance mechanism that responds to the direction of force applied by the user. The power assist mechanism may also provide a safety mechanism for collisions. In particular, the force of contact with another object (e.g., a wall, bed or other structure) may also be detected and the conveyance mechanism will react accordingly with a motorized locomotion response away from the object. According to some embodiments, motorized assistance may be eliminated and the portable MRI system may be transported by having personnel move the system to desired locations using manual force.

Portable MRI system 200 includes slides 260 that provide electromagnetic shielding to the imaging region of the system. Slides 260 may be transparent or translucent to preserve the feeling of openness of the MRI system to assist patients who may experience claustrophobia during conventional MRI performed within a closed bore. Slides 260 may also be perforated to allow air flow to increase the sense of openness and/or to dissipate acoustic noise generated by the MRI system during operation. The slides may have shielding 265 incorporated therein to block electromagnetic noise from reaching the imaging region. According to some embodiments, slides 260 may also be formed by a conductive mesh providing shielding 265 to the imaging region and promoting a sense of openness for the system. Thus, slides 260 may provide electromagnetic shielding that is moveable to allow a patient to be positioned within the system, permitting adjustment by personnel once a patient is positioned or during acquisition, and/or enabling a surgeon to gain access to the patient, etc. Thus, the moveable shielding facilitates flexibility that allows the portable MRI system to not only be utilized in unshielded rooms, but enables procedures to be performed that are otherwise unavailable. Exemplary slides providing varying levels of electromagnetic shielding are discussed in further detail below.

Figure 3:
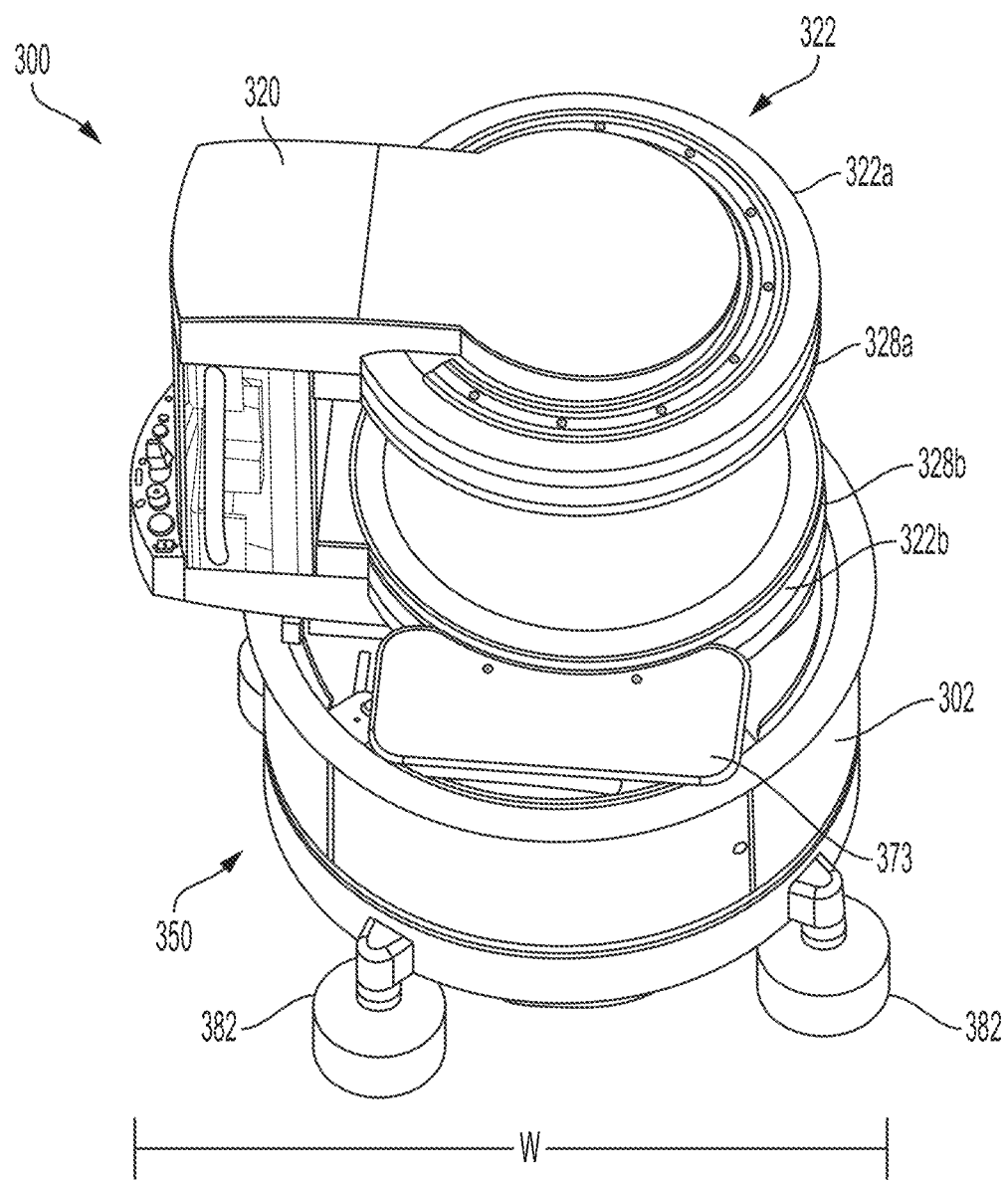
FIG. 3 illustrates a portable MRI system, in accordance with some embodiments.

According to some embodiments, a portable MRI system does not include slides, providing for a substantially open imaging region, facilitating easier placement of a patient within the system, reducing the feeling of claustrophobia and/or improving access to the patient positioned within the MRI system (e.g., allowing a physician or surgeon to access the patient before, during or after an imaging procedure without having to remove the patient from the system). As an example, FIG. 3 illustrates an exemplary portable low-field magnetic resonance imaging system that can be moved to and operated at the point of care. MRI system 300 may be similar to one or more of the portable MRI systems described in the '434 patent, comprising a $B_0$ magnet 322 that includes at least one first magnet 322a and at least one second magnet 322b magnetically coupled to one another by a ferromagnetic yoke 320 configured to capture and channel magnetic flux to increase the magnetic flux density within the imaging region (field of view) of the MRI system. Magnets 322a and 322b may be constructed using any suitable technique, including any of the techniques described in the '434 patent. For example, $B_0$ magnet 322 may include permanent magnet(s), electromagnet(s), printed magnetics, or any thereof. MRI system 300 further comprises gradient coils 328a and 328b to provide X-gradient, Y-gradient and Z-gradient coils for spatial encoding of MR signals.

$B_0$ magnet 322 may be coupled to or otherwise attached or mounted to base 350 to support the $B_0$ magnet. Base 350 includes housing 302 configured to house the electronics needed to operate the portable MRI system 300 (e.g., as described in detail in the '434 patent). To facilitate transporting the system to the point of care, MRI system 300 may include a conveyance mechanism. In FIG. 3, wheels or castors 382 allow the MRI system to be wheeled to desired locations. According to some embodiments, MRI system 300 includes motorized assist to facilitate maneuvering the system, some examples of which are described in the '434 patent. For example, the conveyance mechanism may include a motor to drive wheels/castors 382 provide motorized assistance in transporting MRI system 300 to desired locations. According to some embodiments, the conveyance mechanism may include motorized assistance controlled using a controller (e.g., a joystick or other controller that can be manipulated by a person) to guide the portable MRI system during transportation to desired locations. According to some embodiments, the conveyance mechanism comprises power assist means configured to detect when force is applied to the MRI system by an operator and to, in response, engage the conveyance mechanism to provide motorized assistance in the direction of the detected force, examples of which are described in further detail in the '434 patent.

As shown, MRI system 300 may have a maximum horizontal width W that facilitates the maneuverability of the system within the facilities in which the MRI system is used. According to some embodiments, the maximum horizontal dimension of a portable MRI system is in a range between 40 and 60 inches and, more preferably, in a range between 35 and 45 inches. For example, exemplary MRI system 300 has a maximum horizontal width of approximately 40 inches. As a result, MRI system 300 can be brought to locations in which the MRI is needed, including to the bedside of a patient to be imaged. MRI system 300 also includes bridge 373 that is mounted to the MRI system to facilitate positioning a patient within the imaging region of the MRI system. Bridge 373 may be configured to be attached to different locations around the base to allow a patient to be positioned within the imaging region from different directions and/or orientations. According to some embodiments, bridge 373 is attached to the MRI system 300 so that it can be moved around the perimeter of the $B_0$ magnet. According to some embodiments, bridge 373 is configured to be removed and reattached at different locations around the perimeter of the $B_0$ magnet. According to some embodiments, the bridge may be configured to attach to yoke 320, base 350 or any other suitable portion of MRI system 300, as the aspects are not limited in this respect.

The exemplary low-field MRI systems discussed above and in the '434 patent can be used to provide point-of-care MRI, either by bringing the MRI system directly to the patient or bringing the patient to a relatively nearby MRI system (e.g., by wheeling the patient to the MRI system in a standard hospital bed, wheelchair, etc.). To facilitate imaging of patients using the exemplary systems discussed herein, the inventors have developed techniques to allow a patient to be positioned such that the target anatomy is located correctly within the imaging region of the MRI system, including techniques that allow the patient to be positioned from a standard medical bed, wheelchair or other patient support, even when the patient has limited or no mobility (e.g., the patient is unconscious, sedated or anesthetized, or otherwise has limited autonomous motion).

Following below are more detailed descriptions of various concepts related to, and embodiments of, allowing for point-of-care MRI using a portable low-field MRI. It should be appreciated that the embodiments described herein may be implemented in any of numerous ways. Examples of specific implementations are provided below for illustrative purposes only. It should be appreciated that the embodiments and the features/capabilities provided may be used individually, all together, or in any combination of two or more, as aspects of the technology described herein are not limited in this respect.

Figure 4A:
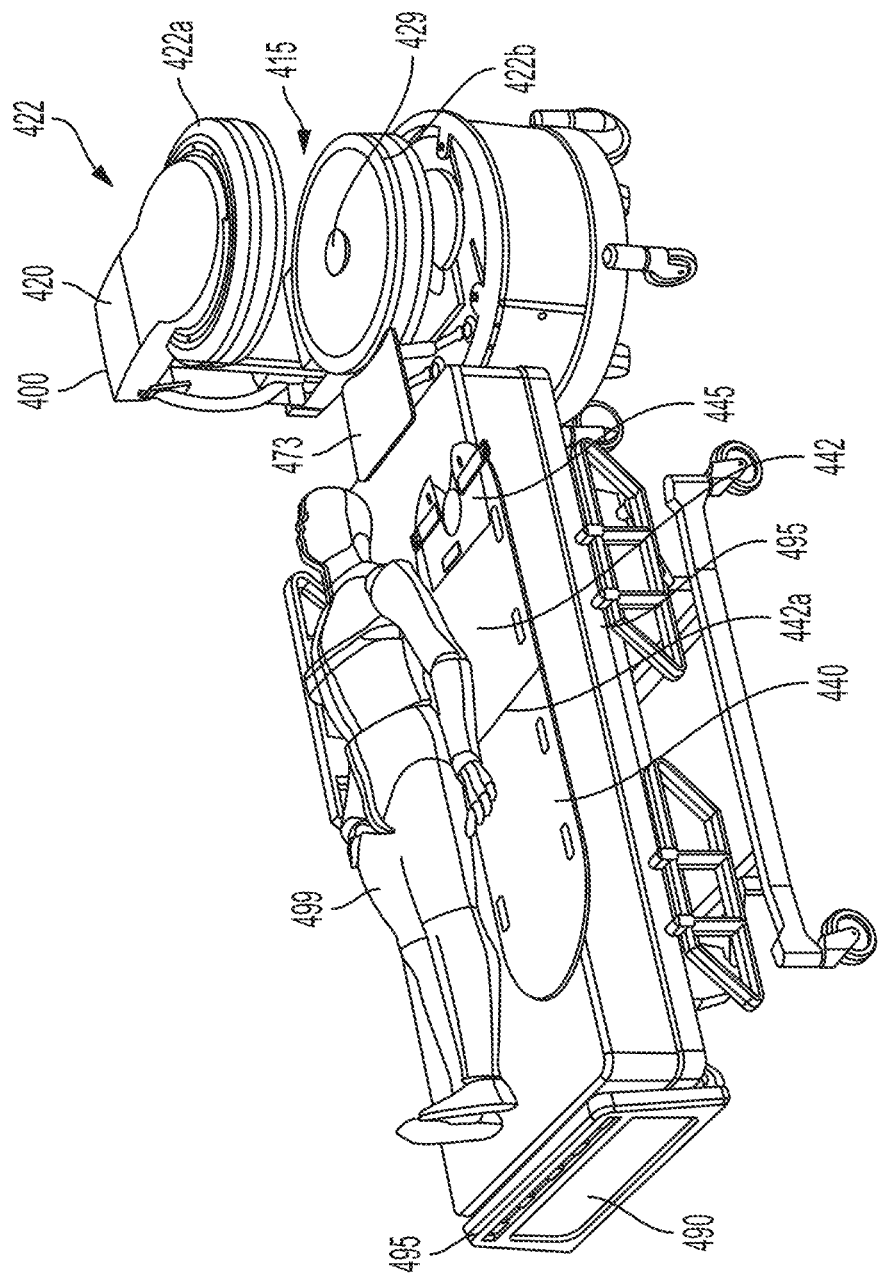
FIGS. 4A-I illustrate a patient handling apparatus that facilitates MRI of a patient from a standard hospital bed, in accordance with some embodiments.

FIG. 4A illustrates a patient handling apparatus that facilitates performing MRI on a patient from a standard hospital bed. FIG. 4A shows a first step of positioning target anatomy of patient 499 within imaging region 415 of MRI system 400 (successive steps are illustrated in FIGS. 4B-4I discussed in further detail below). In particular, a patient 499 for which MRI is desired may be confined to a bed 490 for convenience, comfort or stabilization and/or because the patient is unconscious, immobilized or otherwise is not ambulatory or cannot be safely moved. Bed 490 may be a standard medical or hospital bed of the type typically used in emergency rooms, operating rooms, intensive care units, etc. Such standard hospital beds are typically constructed using ferromagnetic, often steel, that prohibits there use with conventional clinical MRI systems. In addition, hospital beds often have motorized components for raising and lowering different portions of the bed that also often contain material not permitted to be located near a conventional clinical MRI system.

As used herein, the term standard hospital or medical bed refers generally to any bed that has not been manufactured to be MRI-safe according to regulations for current high-field MRI and/or that has not been customized for use with conventional high-field clinical MRI systems (e.g., manufactured to be free of any ferromagnetic material). Therefore, standard medical or hospital bed includes not only general purpose hospital beds, but also beds that have been configured for specific medical purposes other than customized beds manufactured to be compliant with current regulatory requirements for use with conventional high field MRI. Thus, beds that are constructed of ferrous or ferrite material (e.g., ferromagnetic material such as iron, steel, etc.) or other material prohibited from being used in restricted areas of conventional clinical MRI are considered standard hospital beds, even though they may be customized for specific purposes.

For conventional clinical MRI, exemplary bed 490 may comprise a steel frame 495 so that, in addition to needing to be transported to a dedicated MRI facility, the patient would be need to be transferred to an integrated bed of the MRI system and/or transferred to an MRI safe bed (e.g., a specially made bed using aluminum or other non-magnetic material), or both. Such requirements limit the circumstances in which a patient can undergo MRI and in some cases prohibits the use of MRI entirely. In FIG. 4, low-field MRI system 400 has been transported bed-side to the patient to perform point-of-care MRI. Alternatively, low-field MRI system 400 may be a local installation deployed in an emergency room, operating room, intensive care unit, doctor's office, etc. and bed 490 can be wheeled to the MRI system (i.e., MRI system 400 need not be portable). Because of the low-field strengths of MRI system 400, bed 490 can be safely brought into close proximity to $B_0$ magnet 422 of MRI system 400. Additionally, low-field MRI techniques are more robust to perturbations that may be caused by ferromagnetic materials of the bed or in the environment of the MRI system, allowing MRI system 400 to be operated adjacent bed 490 and proximate other equipment in the vicinity that may include ferromagnetic material.

In the embodiment illustrated in FIG. 4A, patient handling apparatus 440 is provided to assist in moving patient 499 into position within imaging region 435 of MRI system 400. The imaging region or field of view defines the volume in which the $B_0$ magnetic field produced by the $B_0$ magnet (e.g., $B_0$ magnet 422 comprising upper $B_0$ magnet 422a, lower $B_0$ magnet 422b and yoke 420 illustrated in FIG. 4A) is suitable for imaging. More particularly, the imaging region or field of view corresponds to the region for which the $B_0$ magnetic field is sufficiently homogeneous at a desired field strength that detectable MR signals are emitted by an object positioned therein in response to application of radio frequency excitation (e.g., a suitable radio frequency pulse sequence). In exemplary MRI system 400, $B_0$ magnet 422 comprises an upper $B_0$ magnet 422a and a lower $B_0$ magnet 422b, each producing a magnetic field to contribute to the $B_0$ magnetic field produced by $B_0$ magnet 422. Upper $B_0$ magnet 422a and a lower magnet 422b are arranged in a bi-planar arrangement to form imaging region 435 between them. $B_0$ magnet 422 also comprises yoke 420 to direct magnetic flux from upper $B_0$ magnet 422a and lower $B_0$ magnet 422b to imaging region 415 to increase the magnetic flux density therein.

Patient handling apparatus 440 comprises a support portion 442 configured to support at least a portion of the patient while the patient is positioned for imaging and a securing portion 445 configured to releasably secure the patient handling apparatus to a radio frequency coil apparatus (e.g., a radio frequency helmet) and to releasably secure the patient handling apparatus to MRI system 400, some embodiments of which are described in further detail below. Securing portion 445 includes at least one releasable securing mechanism configured to secure the patient handling apparatus to a member 429 attached to the MRI system. In the embodiment illustrated in FIG. 4A, member 429 is attached to lower $B_0$ magnet 422b of $B_0$ magnet 422 at a location so that when the patient handling apparatus 440 is secured to member 429, the patient handling apparatus is positioned between upper $B_0$ magnet 422a and lower $B_0$ magnet 422b of the $B_0$ magnet. When a member to which a securing mechanism is configured to engage with is described as being attached to $B_0$ magnet 422b, it means the member is attached to the cover or housing of the $B_0$ magnet, any structure contained within the cover or housing for the $B_0$ magnet and/or attached to the $B_0$ magnet itself.

As discussed in further detail below, securing portion 445 may also include at least one releasable securing mechanism to secure patient handling apparatus 440 to a radio frequency coil apparatus such that when the patient handling apparatus 440 is secured to the radio frequency coil apparatus and to member 429, the radio frequency coil apparatus is positioned at least partially in and, more preferably, substantially within the imaging region of MRI system 400. As a result, when target anatomy of a patient is positioned within the radio frequency coil secured to the patient handling apparatus 400, and the patient handling apparatus 400 is secured to member 429, the target anatomy is positioned within imaging region 415 of MRI system 400 for image acquisition.

As discussed above, patient handling apparatus comprises a support portion 442 configured to support at least a portion of the patient's body to facilitate positioning the patient within the imaging region of the MRI system. Support portion 442 may include a fold or hinge 442a that allows patient handling apparatus to be folded to make the patient handling apparatus more compact, for example, during storage and/or transport and unfolded, for example, during use. Support portion 442 may be constructed from a molded plastic, such as polyethylene or polypropylene. Fold 442a may be a living hinge, a plano hinge, or any other suitable hinge that facilitates the folding of support portion 442. It should be appreciated that support portion 442 may include multiple folds to increase compactness, or may not include a fold at all, as the aspects are not limited in this respect.

As shown in FIG. 4A, a bridge 473 may be mounted to MRI system 400 to facilitate positioning patient handling apparatus 400 within MRI system 400 to secure the securing portion 445 to member 429 via the at least one releasable securing mechanism. According to some embodiments, bridge 473 is configured to mount to bed 490 instead of MRI system 400. According to some embodiments, bridge 472 may be configured to be mountable to either the bed, the MRI system, or both, as the aspects are not limited in this respect. Bridge 473 may be made of material that reduces friction between patient handling apparatus 400 and the bridge, such as a smooth plastic, to facilitate sliding the patient support 440 across the bridge so that securing portion 445 can be secured to member 429 via the at least one releasable securing mechanism. Examples of releasable securing mechanisms for securing and releasing a patient handling apparatus to and from a radio frequency coil apparatus and to secure the patient handling apparatus to the MRI system, in accordance with some embodiments, are described in further detail below.

Figure 4B:
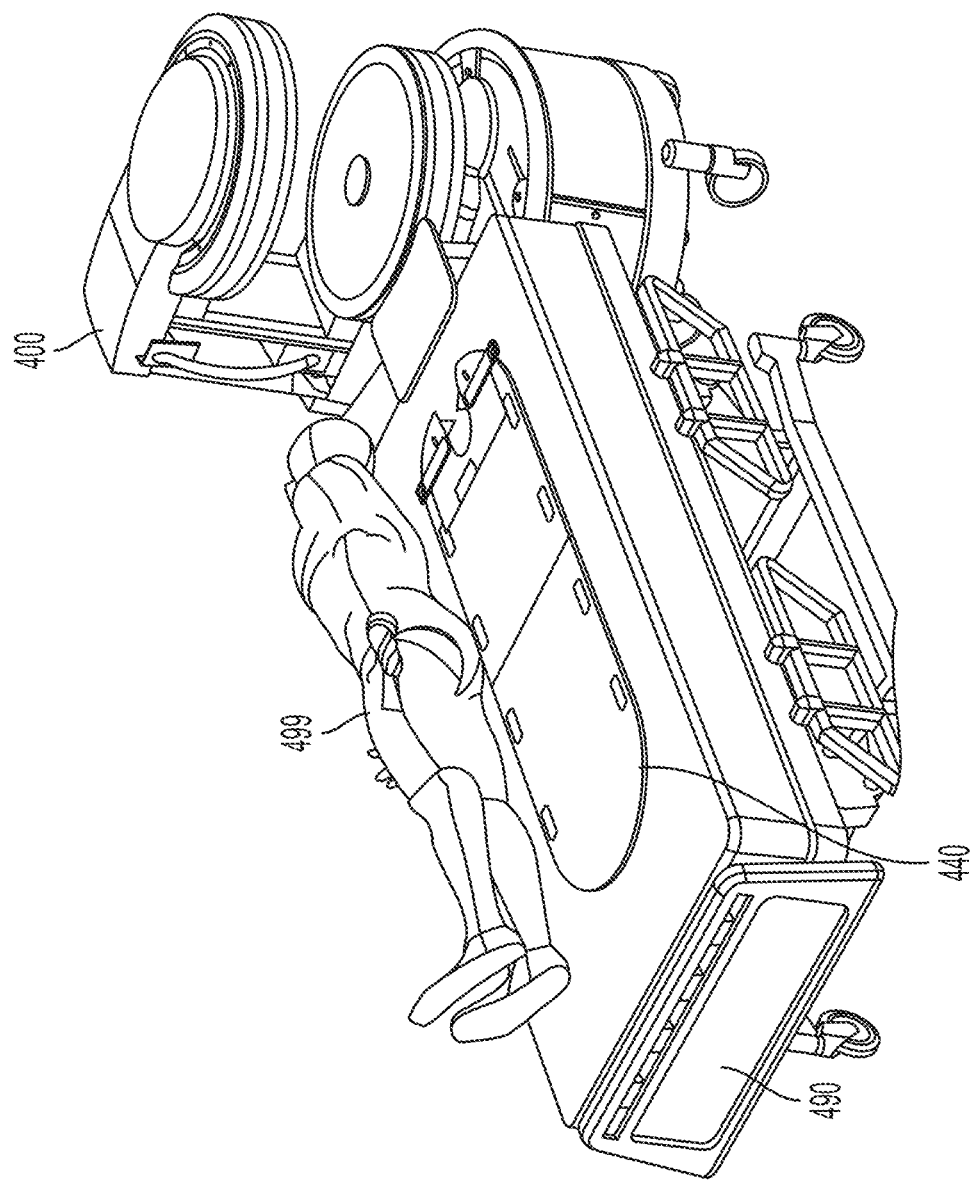
Figure 4C:
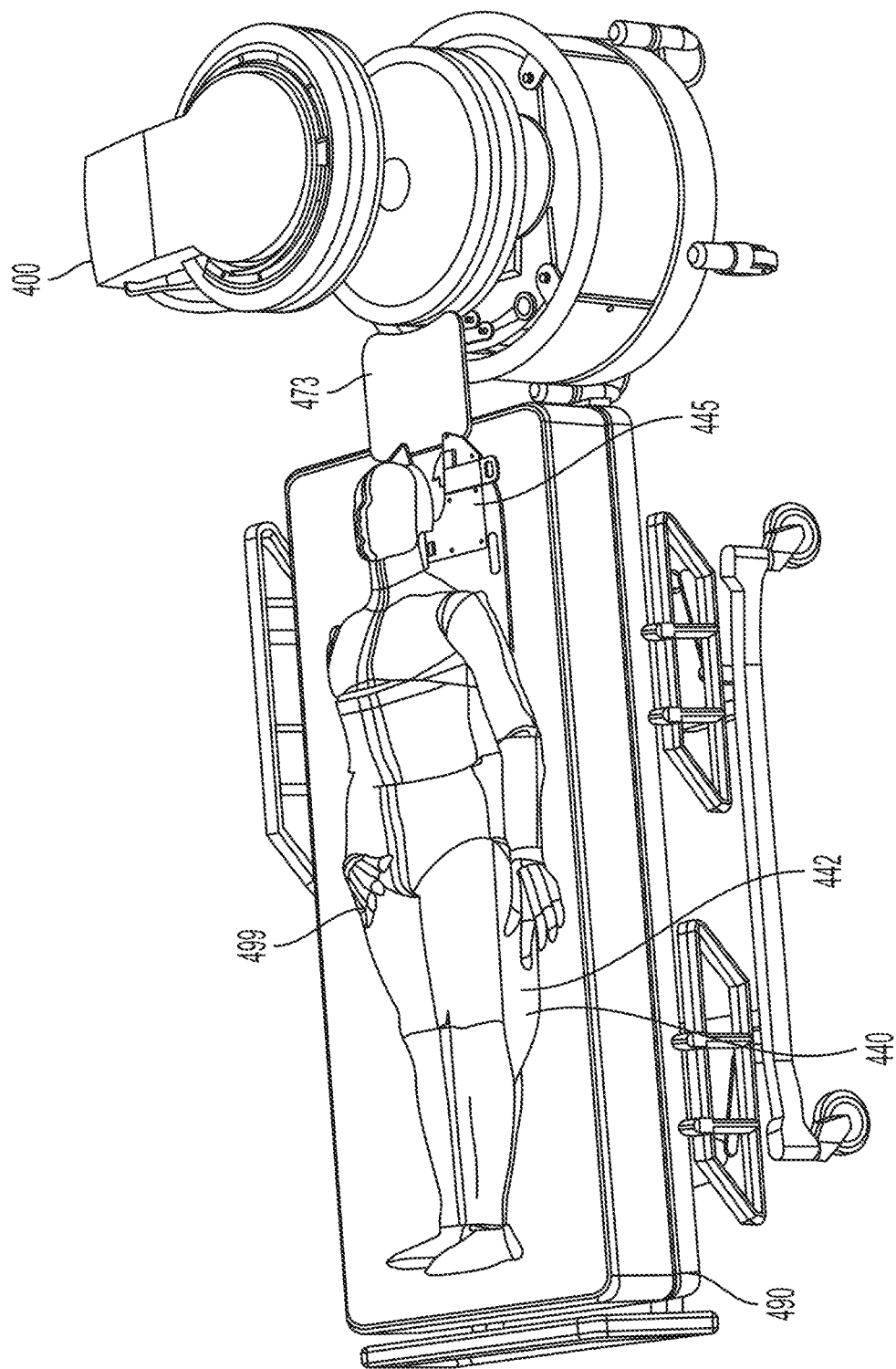
Figure 4D:
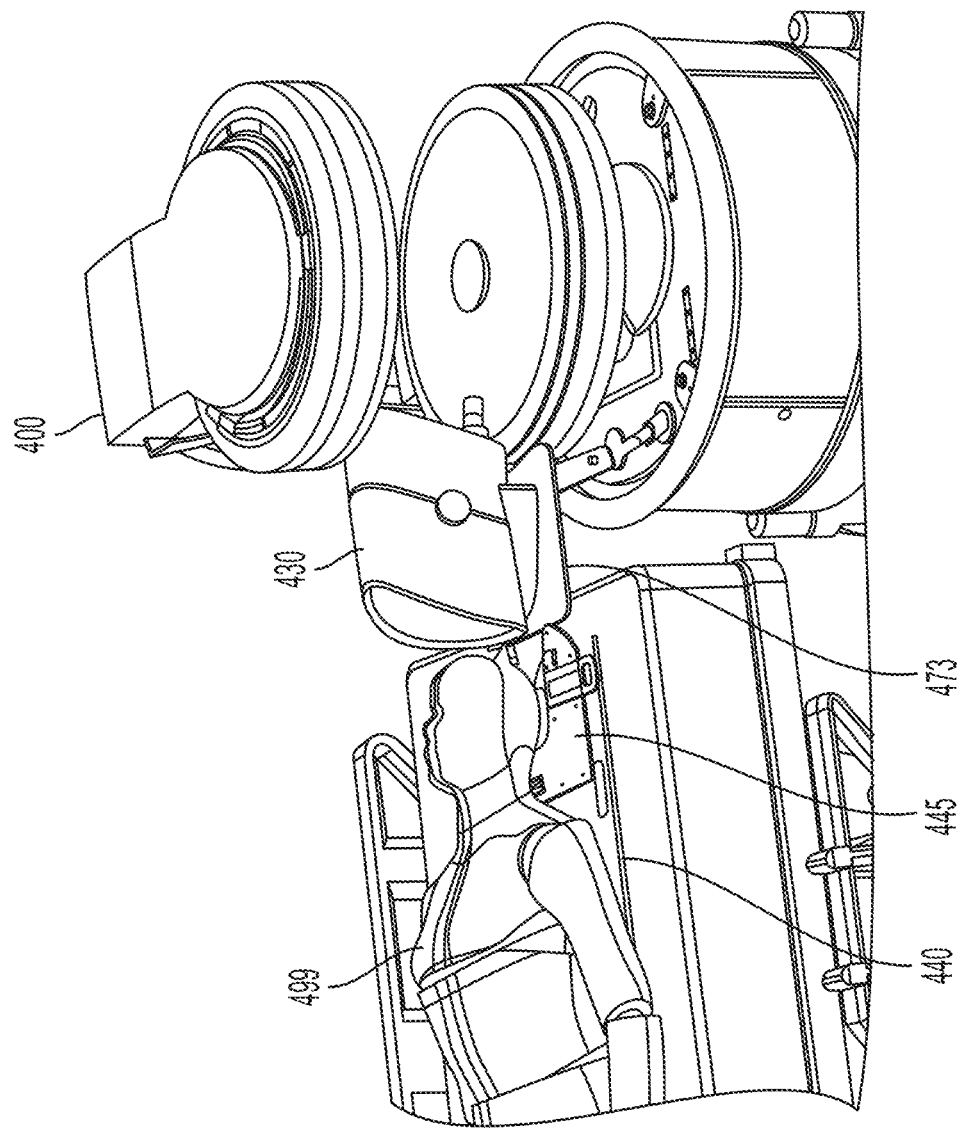
Figure 4E:
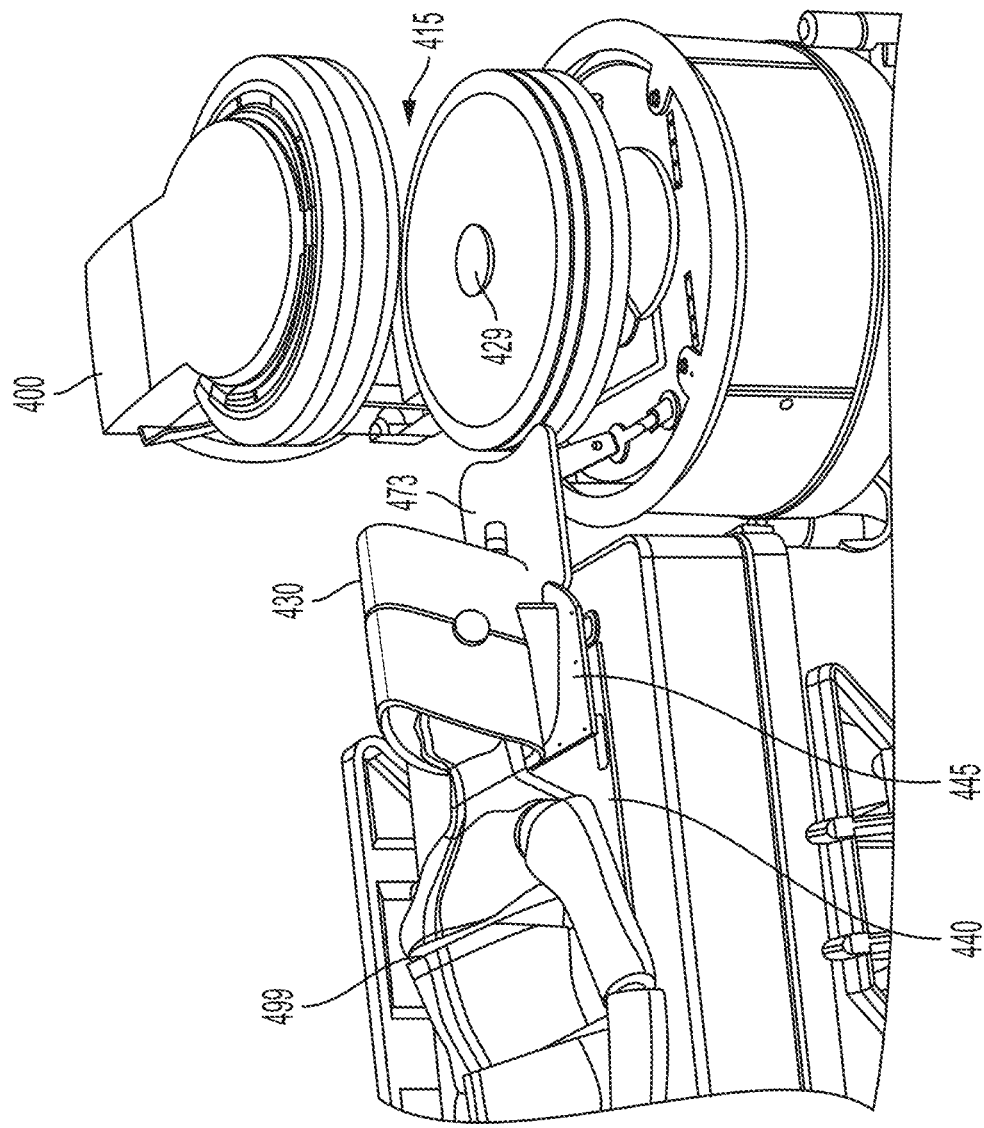
Figure 4F:
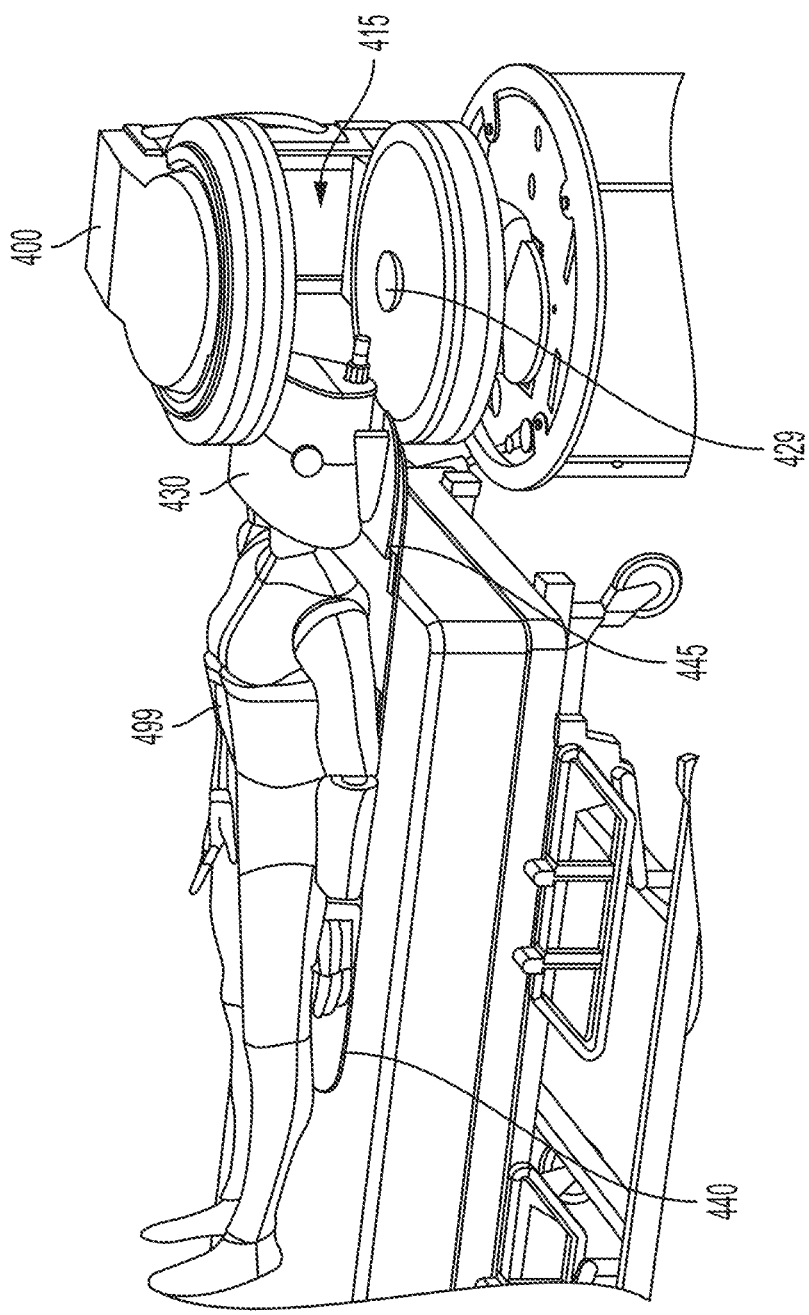
Figure 4G:
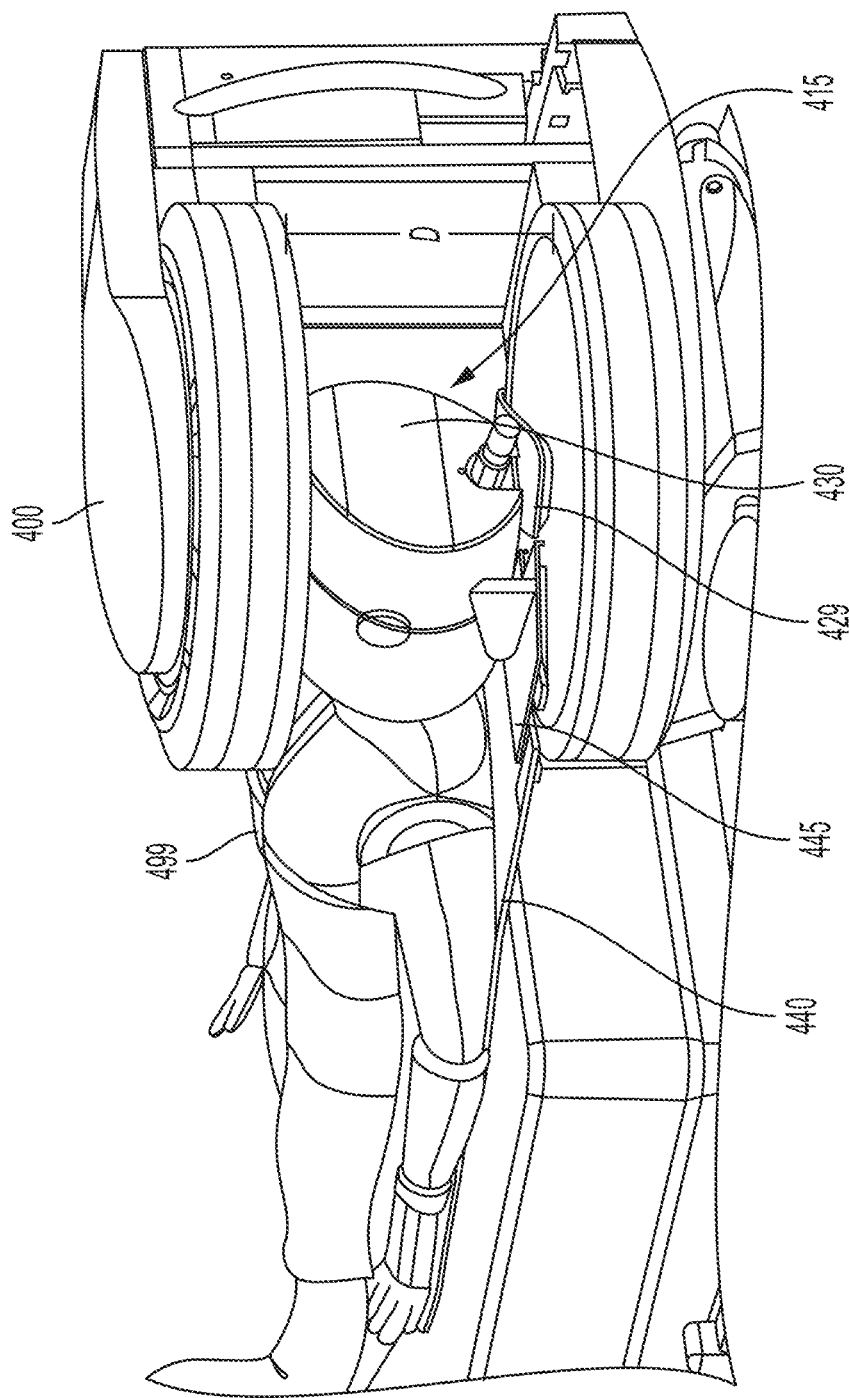
Figure 4H:
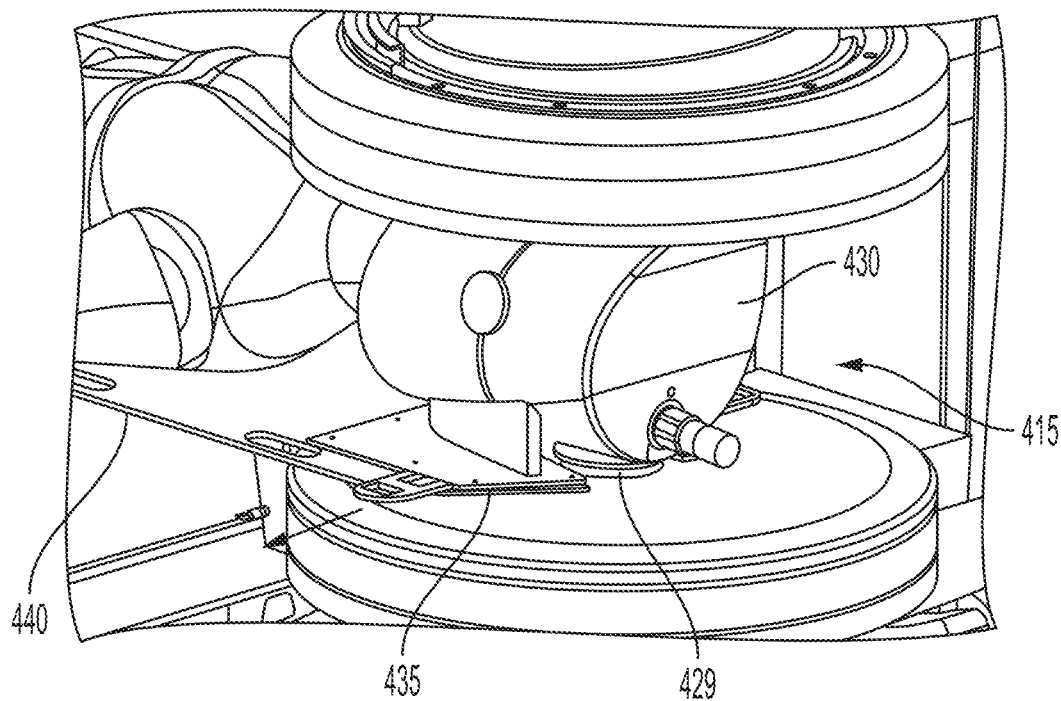
Figure 4I:
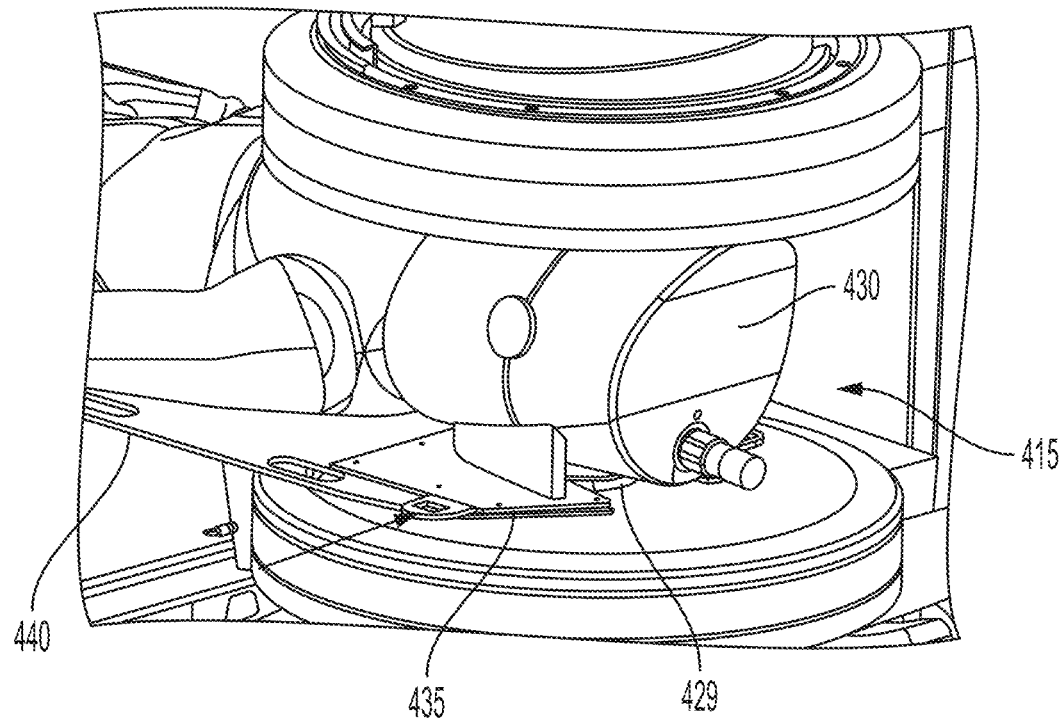
Figure 5A:
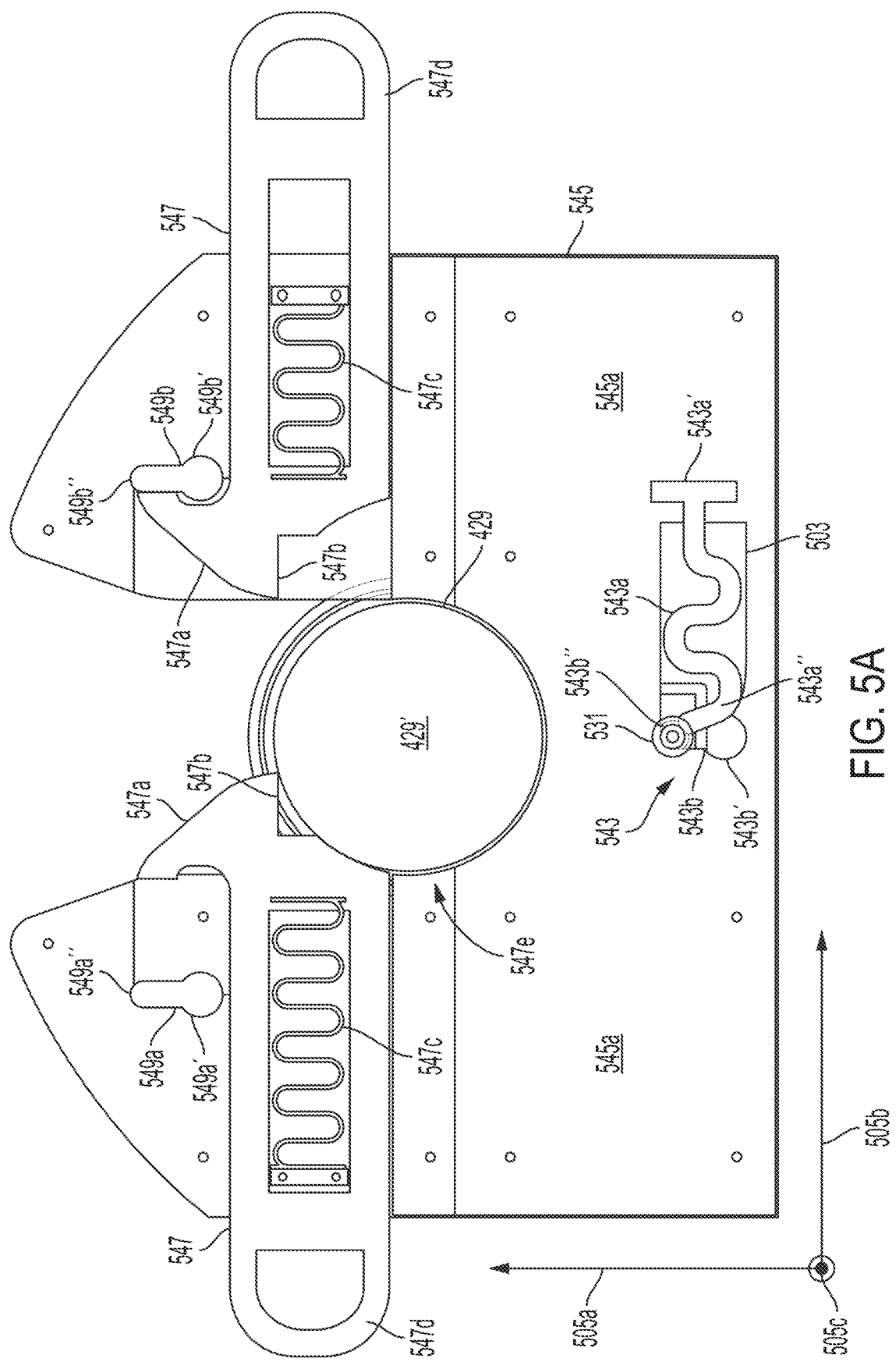
FIGS. 5A-F illustrate aspects of a securing portion of a patient handling apparatus, in accordance with some embodiments.

FIG. 5A illustrates a securing portion of a patient handling apparatus, in accordance with some embodiments. Securing portion 545 may be similar or the same as securing portion 445 of patient handling apparatus 440 illustrated in FIG. 4. In FIG. 5A, the bottom surface (underside) of securing portion 545 is shown (i.e., the surface opposite the surface on which the patient is supported). That is, when the patient handling apparatus to which securing portion 545 is coupled is positioned for use, surface 545a will face down towards the bed in the direction of the floor. In FIG. 5A, securing portion 545 is engaged with member 429 of a magnetic resonance imaging system and a member 531 of a radio frequency coil apparatus to illustrate techniques for securing a patient handling apparatus to the radio frequency coil apparatus and magnetic resonance imaging system to facilitate positioning a patient within the magnetic resonance imaging system, in accordance with some embodiments.

Securing portion 545 comprises a first releasable securing mechanism 543 configured to engage with a radio frequency coil apparatus to secure the securing portion 545 (and thus the patient handling apparatus) to the radio frequency coil apparatus. In the exemplary embodiment illustrated in FIG. 5A, the first releasable securing mechanism 543 comprises a retention member 543a and a keyhole slot 543b to engage with member 531 of a radio frequency coil apparatus (e.g., a radio frequency helmet) to secure the patient handling apparatus to the radio frequency coil apparatus. Keyhole slot 543b includes a larger diameter portion 543b' and a smaller diameter portion 543b" dimensioned so that member 531 can be inserted into larger diameter portion 543b' in a first direction along axis 505c (i.e., in a direction out of the page of the drawing) and slid into smaller diameter portion 543b" where the smaller diameter prevents member 531 from exiting keyhole slot 543b in a second direction along axis 505c (i.e., in a direction opposite the direction member 531 was inserted into keyhole slot 543b). Securing portion 545 may include additional keyhole slots 549a and 549b, each with respective larger and smaller diameter portions (e.g., larger diameter portions 549a' and 549b', and smaller diameter portions 549a" and 549b", respectively. Additional keyhole slots may be included to assist in securing the radio frequency coil apparatus to the securing portion, an example of which is illustrated in FIGS. 5B and 5C.

Retention member 543a is configured to allow member 531 to be moved into smaller diameter portion 543b" (i.e., in a first direction along axis 505a) and to snap into place to retain member 531 in smaller diameter portion 543b" (i.e., retention member 543a resists movement of member 531 in a second direction along axis 505a out of the smaller diameter portion into the larger diameter portion). Accordingly, once member 531 has been moved from larger diameter portion 543b' to smaller diameter portion 543b", smaller diameter portion 543b" and retention member 543a secure the radio frequency coil apparatus to the securing portion 545. To disengage the radio frequency coil apparatus from securing portion 545 of a patient handling apparatus, a force may be applied against retention mechanism 543a so that retention mechanism 543a moves aside to allow member 531 to be moved into larger diameter portion 543b of keyhole slot 543b so that the radio frequency coil apparatus can be lifted away from securing portion 545. For example, a force applied to the radio frequency coil apparatus in the second direction along axis 505a causes retention mechanism 543b to slip so that member 531 is allowed to slide into the larger diameter portion of the keyhole.

This process of securing a patient handling apparatus to, and releasing it from, a radio frequency helmet, is described in further detail below in connection with FIGS. 5B and 5C. In particular, FIGS. 5B and 5C illustrate the underside of a patient handling apparatus 540 comprising a support portion 542 and securing portion 545 as it is engaging with radio frequency helmet 530. Radio frequency helmet 530 is configured to accommodate the head of a patient and comprises one or more radio frequency coils configured to transmit magnetic resonance pulse sequences and/or detect MR signals emitted from the patient in response to a transmitted pulse sequence. The radio frequency coils may be, for example, any of the radio frequency coils and geometries thereof described in U.S. application Ser. No. 15/152,951, filed on May 31, 2016 and titled "Radio Frequency Coil Methods and Apparatus." Radio frequency helmet 530 comprise member 53 configured to engage with securing mechanism 543 of securing portion 545 of patient handling apparatus 540, and members 533a and 533b configured to engage with keyhole slots 549a and 549b.

Figure 5B:
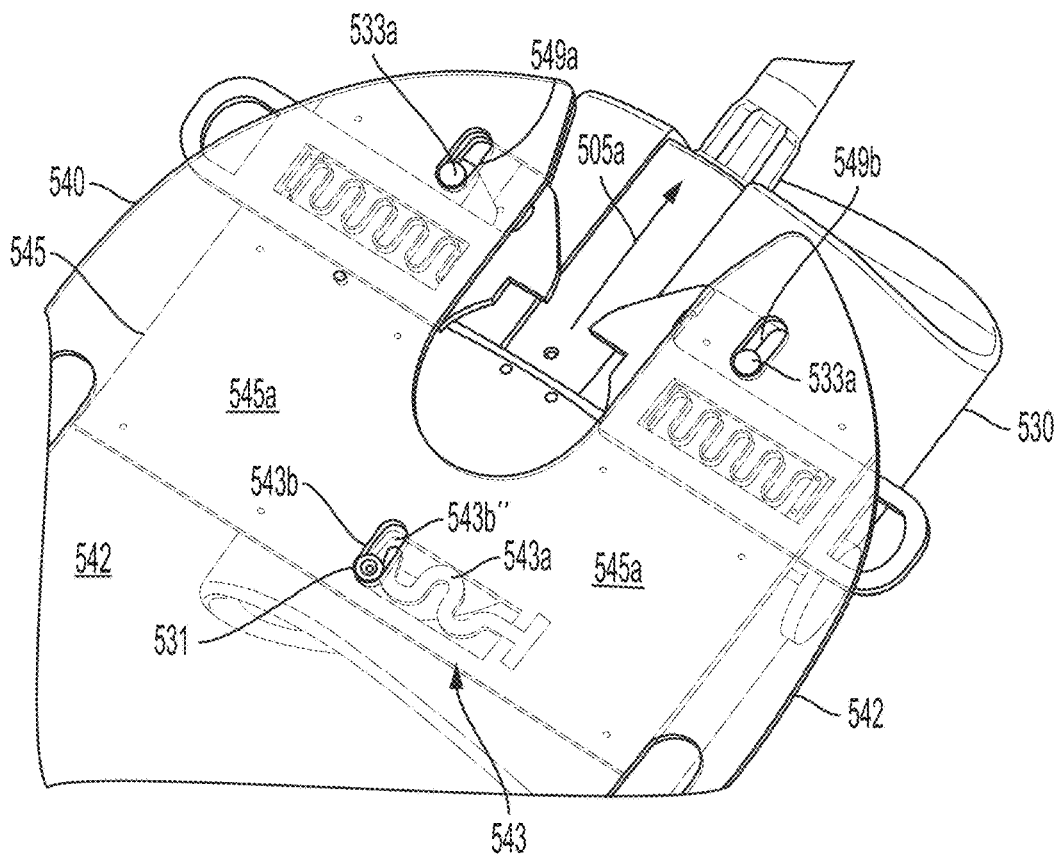
Figure 5C:
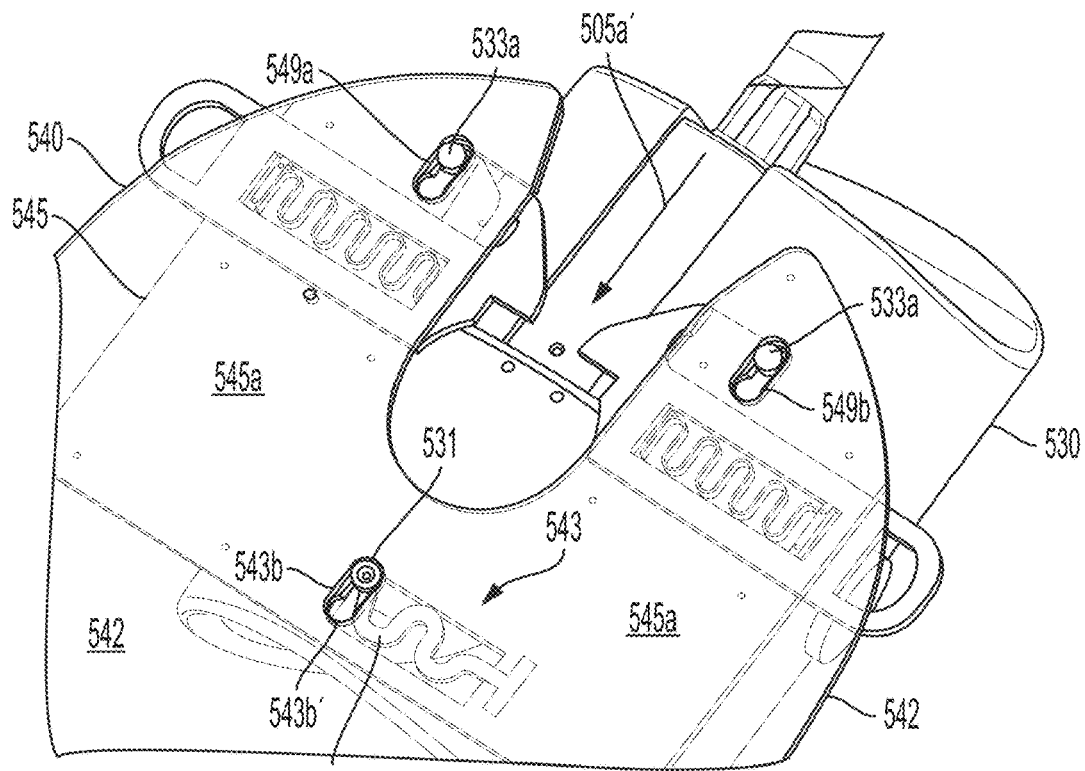

In FIG. 5B, members 531, 533a and 533b have been inserted into respective keyhole slots 543b, 549a and 549b and, more particularly, have been inserted through the respective larger diameter portions of the respective keyhole slots that are dimensioned to allow the respective member to be inserted into the respective keyhole slot. By moving the radio frequency coil apparatus 530 in the direction indicated by arrow 505 (or moving the patient handling apparatus in the opposite direction), members 531, 533a and 533b can be moved from the larger diameter portion to the smaller diameter portion of the respective keyhole slot. For example, member 531 can be moved from larger diameter portion 543b' (see FIG. 5C) to the smaller diameter portion 543b" (see FIG. 5B) of keyhole slot 543b. The result of this movement is illustrated in FIG. 5C.

As shown in FIG. 5C, radio frequency helmet 530 has been secured to patient handling apparatus 540. Because the smaller diameter portions of the keyhole slots are dimensioned to be smaller than the diameter of the portion of the member inserted through the larger diameter portion of the keyhole slot, radio frequency helmet 530 cannot be lifted from the securing portion 545 of patient handling apparatus 540 without first being returned to the large diameter portions. As also shown in FIG. 5c, retention member 543 snaps into place to resist movement of the member 531 back into the larger diameter portion 543b' of keyhole slot 543b. That is, retention member resists movement of radio frequency coil apparatus 530 in the direction indicated by arrow 505'. However, the resistance of retention member 543a can be overcome by providing a strong enough force in the direction of arrow 505' to return the radio frequency coil apparatus 530 to the position illustrated in FIG. 5B so that the radio frequency helmet 530 can moved away from or lifted off of securing portion 545, thereby disengaging radio frequency helmet 530 from patient handling apparatus 540. In this manner, securing mechanism 543 releasably secures radio frequency helmet 530 to patient handling apparatus 540 (e.g., by providing sufficient force to overcome the resistance of the retention member, the secured helmet can be released from the releasable securing mechanism 543).

Figure 6A:
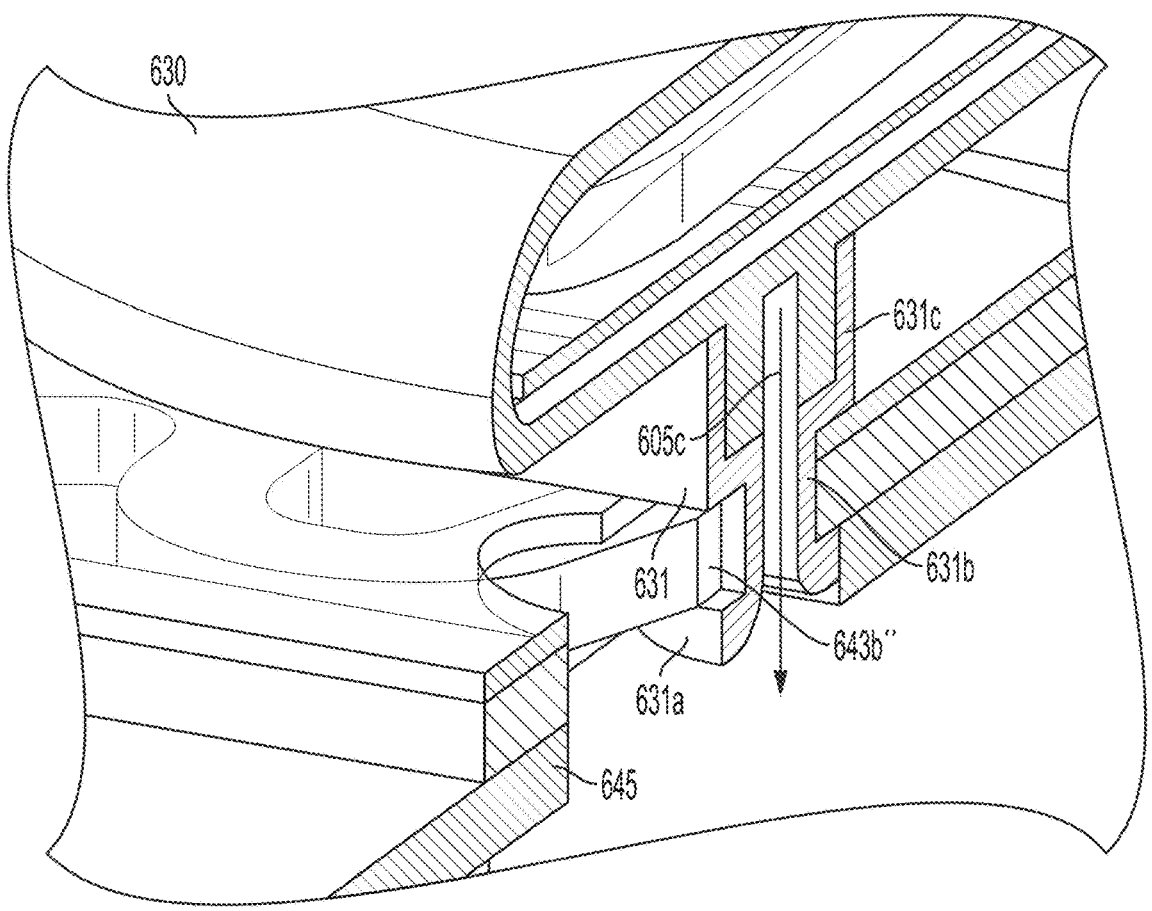
FIGS. 6A-B illustrate a releasable securing mechanism, in accordance with some embodiments.
Figure 6B:
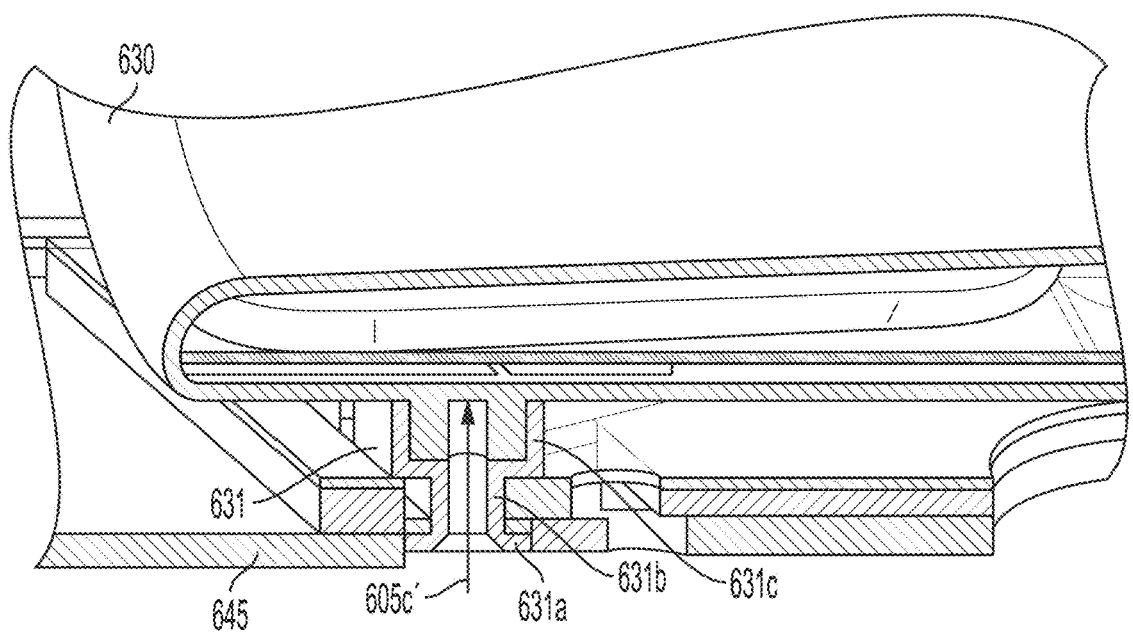

FIGS. 6A and 6B illustrates a cross-sectional view of a radio frequency coil apparatus 630 secured within a keyhole slot of a releasable securing mechanism of a securing portion 645 of a patient handling apparatus. Radio frequency coil apparatus 630 comprises a member 631 configured to engage with a keyhole slot of securing portion 645. Member 631 comprises portions 631a, 631b and 631c dimensioned differently so that member 631 can be inserted into the keyhole slot and slid into a secured position. Foot portion 631a is dimensioned to be sufficiently small so that it can be inserted into the larger diameter portion (not visible in FIGS. 6A and 6B, but see e.g., larger diameter portion 543b' illustrated in FIGS. 5A and 5C) of the keyhole slot and sufficiently large so it cannot be inserted into or removed from the smaller diameter portion 643$b''$ of the keyhole slot (see also smaller diameter portion 543$b''$ illustrated in FIGS. 5A and 5B).

Neck portion 631$b$ is dimensioned to be sufficiently small so that it can be accommodated by the smaller diameter portion 643$b''$ of the keyhole slot so that, after foot portion 631$a$ is inserted in the larger portion of the keyhole slot, member 631 can be moved into the smaller diameter portion 643$b''$. Body portion 631$c$ is dimensioned to be sufficiently large so that it cannot be accommodated by either the smaller or the larger diameter portions of the keyhole slot. Neck portion 631$b$ has height (e.g., its dimension in the direction of arrow 605$c$) so that when body portion 631$c$ prevents further insertion of member 631 into the keyhole slot (i.e, further movement in the direction of arrow 605$c$ is prevented by body portion 631$c$), foot portion 631$a$ has been positioned through the large diameter portion of the keyhole slot so that member 631 can be slid into the smaller diameter portion 643$b''$ to the secured position illustrated in FIGS. 6A and 6B. Because foot portion 631$a$ is larger than the smaller diameter portion 643$b''$, member 631 cannot be lifted from securing portion 645 in the direction of arrow 605$c'$ without first being transitioned back into the larger diameter portion of the keyhole slot.

Referring again to FIG. 5A, according to some embodiments, retention member 543$a$ is made from plastic and is formed into a flat serpentine geometry. For example, retention member 543$a$ may be a flat plastic spring, having a fixed end 543$a'$ and a free end 543$a''$ that can move to allow member 531 to be slid into smaller diameter portion 543$b''$ and return to position to resist movement of member 531 back into larger diameter portion 543$b'$. The free end 543$a''$ may be located in window 503. The depth of window 503 (i.e., generally corresponding to the thickness of securing portion 545 in the direction along axis 505$c$) may be relatively small. As a result, retention member 543$a$ may also have a relatively small thickness in directions along axis 505$c$ (i.e., the thickness of the material forming the retention member, for example, the thickness of the plastic may be required to be relatively thin). That is, retention member 543$a$ may be constructed to be flat so that the member does not extend beyond surface 545$a$ (or extend beyond the top surface of securing portion 545 on which the radio frequency apparatus rests when engaged). According to some embodiments, retention member comprises a flat plastic spring with a thickness less than or equal to approximately 0.5 inches. According to some embodiments, retention member comprises a flat plastic spring with a thickness less than or equal to approximately 0.25 inches. In this way, the retention mechanism can be contained within the thickness of the securing portion 545.

Securing portion 545 may further comprise a second releasable securing mechanism 547 configured to engage with a magnetic resonance imaging system to secure the securing portion 545 (and thus the patient handling apparatus) to the magnetic resonance imaging system. According to some embodiments, second releasable securing mechanism 547 comprises tapered lead-in portions 547$a$ that allows a member 429 attached to the magnetic resonance imaging system to enter receptacle portion 547$e$, and comprises retention portions 547$b$ that prevent member 429 from exiting receptacle 547$d$. Pulls 547$d$ allow a user to retention portions 547$b$ to allow member 549 to exit receptacle 547$d$. Springs 547$c$ allow the releasable securing mechanism to be actuated, either by utilizing pulls 547$d$ or under the force of member 429 pushing against tapered lead-in portions 547$a$. It should be appreciated that the underside of member 429 is illustrated in FIG. 5A to show how releasable securing mechanism 547 engages with member 429, but that surface 429' of member 429 is the surface that is attached to the magnetic resonance imaging system, for example, attached to lower $B_0$ magnet 422$b$ as shown in FIG. 4A.

Figure 5D:
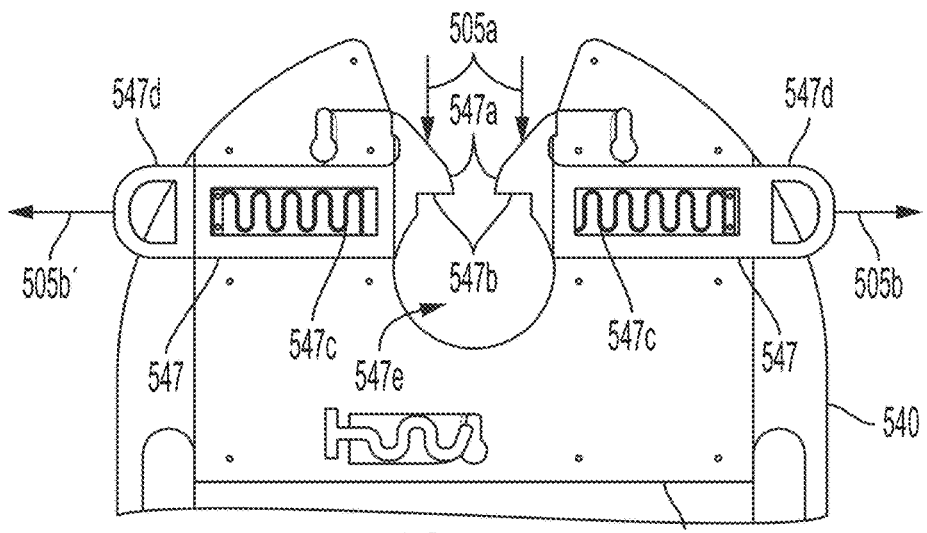
Figure 5E:
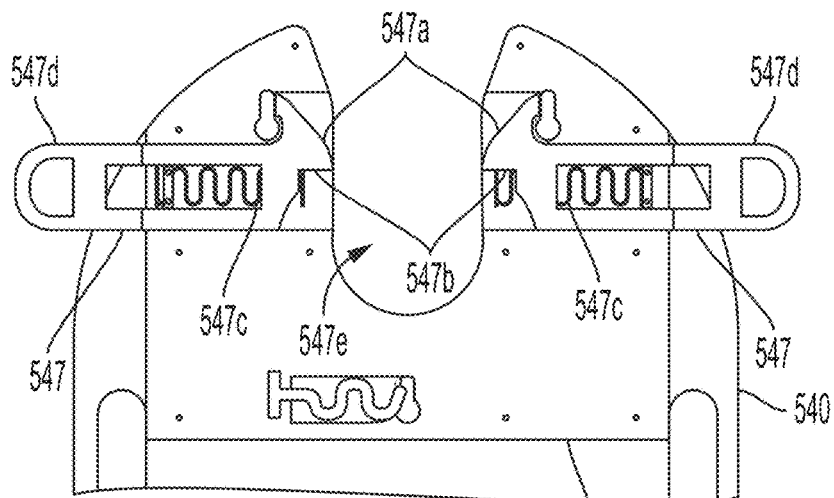
Figure 5F:
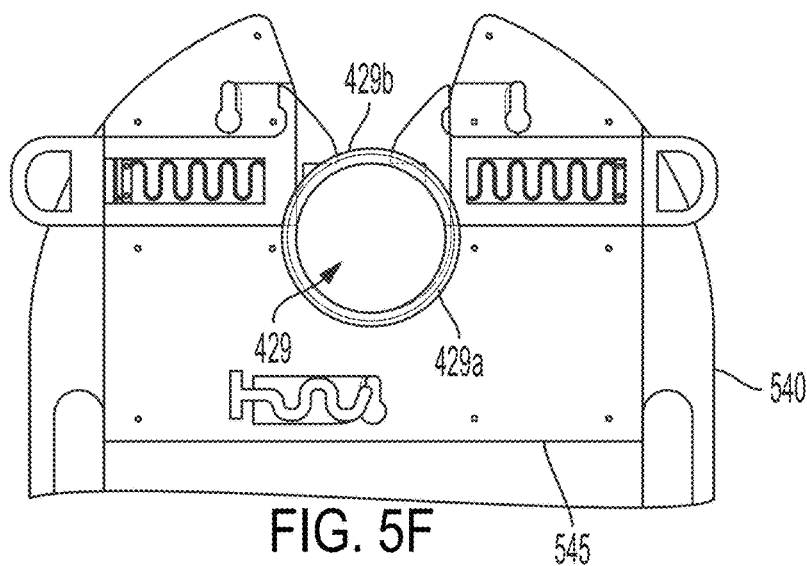

FIGS. 5D-F illustrate the operation of an exemplary releasable securing mechanism 547. FIG. 5D illustrates releasable securing mechanism 547 in a closed position in which springs 547$c$ are in repose and tapered portions 547$a$ and retentions portion 547$b$ extend into receptacle 547$e$. Releasable securing mechanism 547 can be opened by applying a force on pulls 547$d$ in the directions shown by arrows 505$b$ and 505$b'$ or by applying a force to tapered portions 547$a$ in the direction shown by arrows 505$a$ to move securing mechanism 547 to the open position shown in FIG. 5E. When releasable securing mechanism 547 is opened, springs 547$c$ are compressed and tapered portions 547$a$ and retention portions 547$b$ separate to allow entry and/or exit of member 439 into receptacle 547$e$. When the force applied to open securing mechanism 547 is removed, springs 547$c$ return to their repose position, forcing tapered portions 547$a$ and retention portions 547$b$ towards each other to close the path for 439 into and out of receptacle 547$e$, returning the releasable securing mechanism 547 to the position illustrated in FIG. 5D.

Force in the direction shown by arrows 505$a$ may be applied by pushing the tapered portions 547$a$ against member 429, thereby compressing springs 547$c$ and opening the securing mechanism to allow member 429 to enter receptacle 547$e$. After member 429 enters receptacle 547$e$, springs 547C return to their repose position and retention portions 547$b$ close behind member 429 to secure securing portion 545 of patient handling apparatus 540 to the magnetic resonance imaging system, as illustrated in FIG. 5F. As shown in FIG. 5F, member 429 may include a smaller diameter portion 429$a$ dimensioned to fit within receptacle 547$e$, and a larger diameter portion 429$b$ dimensioned to be larger than receptacle 547$e$. Securing portion 545 is dimensioned so that at least the portions forming receptacle 547$e$ fit underneath larger diameter portion 429$b$ so that when securing portion 545 is engaged with member 429 as shown FIG. 5F, the larger diameter portion 429$b$ prevents patient handling apparatus 540 from being lifted away from the magnetic resonance imaging system, while retention portions 547$b$ retain member 429 within receptacle 547$e$ of releasable securing mechanism 547. In particular, for exemplary member 429 illustrated in FIG. 5F, the smaller diameter portion 429$a$ has a height that allows those portions of securing portion 545 forming receptacle 547$e$ to fit underneath larger diameter portion 429$b$ to hold securing portion 545 to the surface to which member 429 is attached.

To release patient handling apparatus from the magnetic resonance imaging system, a user can apply a force to pulls 547$d$ in the directions shown by arrows 505$b$ and 505$b'$ to open releasable securing mechanism 547 (e.g., to place releasable securing mechanism 547 in the open position illustrated in FIG. 5E). With the path out of receptacle 547$e$ for member 429 opened, patient handling apparatus 540 can be disengaged from the magnetic resonance imaging system. According to some embodiments, pulls 547$d$ are configured to operate independently of one another so that both sides need to be pulled to open securing mechanism 547$d$. According to some embodiments, pulling on either of pulls 547$d$ engages both sides so that only one pull needs to be used to open securing mechanism 547.

Referring again to FIG. 4A, member 429 may be attached to MRI system 400 at a location such that when releasable securing mechanism 547 engages member 429 (e.g., as shown in FIGS. 5A and 5F), a radio frequency coil apparatus that has been secured to the patient handling apparatus is located substantially within the imaging region of the MRI system. For example, when radio frequency helmet 530 is secured to securing portion 545 of patient handling apparatus 540 via releasable securing mechanism 543 and second releasable securing mechanism 547 is engaged with member 429, radio frequency helmet 530 is positioned substantially within the imaging region of the MRI system (e.g., as shown in FIG. 4I). As a result, when target anatomy is positioned within the radio frequency coil apparatus, the target anatomy is within imaging region 415 of MRI system 400.

FIGS. 4A-4I illustrate exemplary steps that allow a patient to be imaged from a standard hospital bed, in accordance with some embodiments. In FIG. 4A, a patient handling apparatus 440 may be positioned on bed 490 proximate patient 499 patient to begin the process of positioning the patient within MRI system 400. As shown in FIG. 4B, patient 499 may be rolled to the side or partially lifted so that patient handling apparatus can be moved towards the center of bed 490 and/or generally aligned with MRI system 400. Patient 499 can then be rolled back or released so that patient handling apparatus 440 is positioned between bed 490 and patient 499 and at least a portion of patient 499 is supported by support 442 of patient handling apparatus 440, as shown in FIG. 4C. The head of patient 499 may be positioned generally over securing portion 445 of patient handling apparatus 440, which itself may be positioned proximate bridge 473 to facilitate positioning patient 499 within MRI system 400.

As shown in FIG. 4D, a radio frequency helmet 430 may be positioned on bridge 473 or otherwise positioned to engage with securing portion 445 of patient handling apparatus 440. Radio frequency helmet 430 may then be secured to securing portion 435 of patient handling apparatus 440 with the patient's head positioned within the radio frequency helmet 430, as shown in FIG. 4E. For example, radio frequency helmet 430 may be secured by engaging a releasable securing mechanism of securing portion 435 with a cooperating member or members of radio frequency helmet 430, as discussed in connection with FIGS. 5A-C and FIGS. 6A-B. Patient handling apparatus 440, with radio frequency helmet 430 secured, is ready to be moved over bridge 473 to engage with member 429 to secure the patient handling apparatus to MRI system 400, as shown in FIG. 4F.

FIG. 4G illustrates patient handling apparatus 440 as the entrance to a releasable securing mechanism of securing portion 445 approaches member 429 (e.g., approaches the entrance to a receptacle of the releasable securing mechanism). As shown, radio frequency helmet 430, which is accommodating or holding the patient's head, has entered imaging region 415 of MRI system 400. At the stage illustrated in FIG. 4H, member 429 engages with tapered lead-in portions of a releasable securing mechanism (e.g., tapered lead-in portions 547a of releasable securing mechanism 547 illustrated in FIGS. 5A and 5D-F) causing the releasable securing mechanism to open to allow member 429 to enter a receptacle of the releasable securing mechanism (e.g., receptacle 547e illustrated in FIGS. 5A-F). Once member 429 has passed into the receptacle beyond the tapered lead-in portions, the releasable securing mechanism closes and retention portions of releasable securing mechanism prevent member 439 from exiting the receptacle, as shown in FIG. 4I. In this position, patient handling apparatus 440 is secured to MRI system 400 and radio frequency helmet 430 and the patient's head are positioned correctly with imaging region 415 so that one or more image acquisition processes may be performed.

As shown in FIGS. 4A-4I, point-of-care MRI may be performed by bringing a portable low field MRI system (e.g., MRI system 400) to the patient (or wheeling a patient to the MRI system in the patient's bed) so that MRI can be performed on the patient from the patient's bed, even under circumstances where the patient has limited or no mobility (e.g., the patient is injured, unconscious or otherwise has limited mobility). As a result, MRI may be made available in numerous circumstances where it was previously unavailable. As discussed above, because of the relatively low field strengths involved in low-field MRI, MRI can be performed on the patient without needing to transfer the patient to an MRI-safe bed, allowing for imaging of the patient from whatever bed the patient is positioned on, opening up MRI to emergency rooms, operating rooms, intensive care units, doctor's offices and clinics, etc.

Figure 7A:
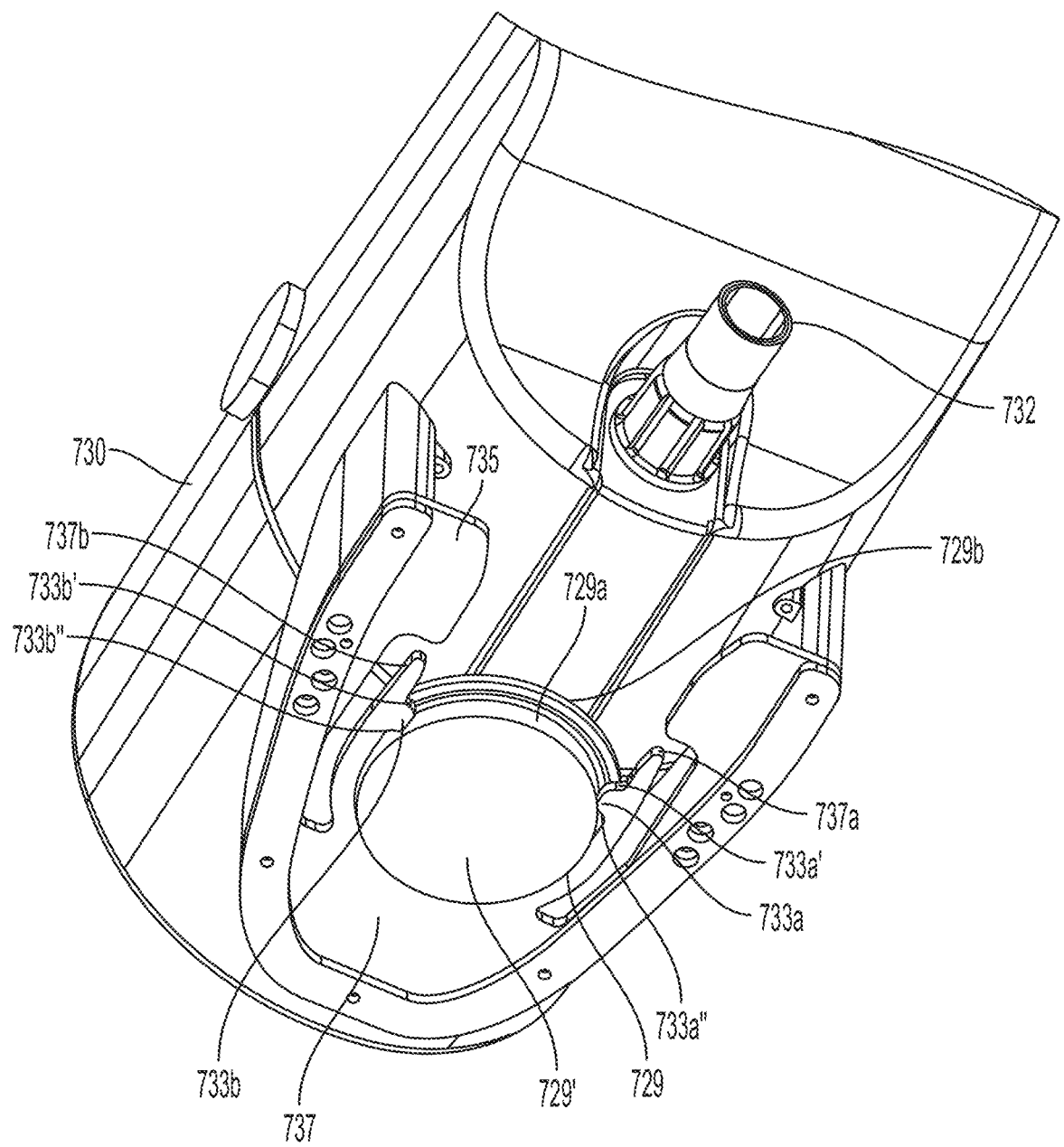
FIGS. 7A-B illustrate aspects of a releasable securing mechanism of a radio frequency coil apparatus, in accordance with some embodiments.

According to some embodiments, a radio frequency coil apparatus may be configured to be directly secured to an MRI system without first being secured to a patient handling apparatus. FIG. 7A illustrates a radio frequency helmet configured to engage directly with the MRI system to secure the radio frequency helmet within the imaging region of the MRI system to position the patient for imaging, in accordance with some embodiments. In particular, FIG. 7A illustrates the underside of a radio frequency helmet 730 equipped with a releasable securing mechanism 735 configured to engage with and grip a member 729 attached to the MRI system. Member 729 may be similar or the same as member 429 in that it is attached to the MRI system at a location such that when radio frequency helmet 730 is secured to member 729, the radio frequency helmet 730 is positioned within the imaging region of the MRI system. Member 729 may also include a smaller diameter portion 729a and a larger diameter portion 729b configured to cooperate with releasable securing mechanism 735 to secure radio frequency helmet 730, as discussed in further detail below.

Releasable securing mechanism 735 comprises a receptacle dimensioned to accommodate member 729 and a retention portion 737 configured to resist movement of the cooperating member 729 once the member has been positioned within the receptacle, as shown in FIG. 7A. Exemplary retention portion 737 comprises two arm portions 737a and 737b forming a portion of the receptacle and configured to grip member 729 when member 729 is positioned within the receptacle. According to some embodiments, arm portions 737a and 737b include protrusions 733a and 733b, respectively, configured to resist movement of member 729 after it has been inserted into the receptacle of releasable securing mechanism 735. Protrusions 733a and 733b comprise respective outward facing sides 733a' and 733b' and respective inward facing sides 733a" and 733b" dimensioned to facilitate engaging with member 729 to secure radio frequency helmet 730 to the MRI system. According to some embodiments, the angle of the outward facing sides of protrusions 733a and 733b and the angle of the inward facing sides of protrusions are configured such that less forced is required to allow member 729 to enter into the receptacle of securing mechanism 735 than to allow member 729 to exit from the receptacle. For example, the relative angles of the outward and inward facing sides may be selected so that a relatively small force on the outward facing sides is needed to part arm portions 737a and 737b to allow member 729 to enter the receptacle of releasable securing mechanism 735 and a larger force on the inward facing sides is needed to part arm portion 737a and 737b to allow member 729 to be released from the receptacle of securing mechanism 735. It should be appreciated that protrusions 733a and 733b may be dimensioned in any way to achieve desired forces needed to engage and disengage member 729 with securing mechanism 735, as the aspects are not limited in this respect. Thus, radio frequency helmet 730 can be secured to and released from member 729 by applying a force in the appropriate direction. That is, securing mechanism 735 is releasable because after arm portions 737a and 737b grip member 729, the grip can be released by providing sufficient force on helmet 730 so that member 729 parts the arm portions 737a and 737b and releases the member.

Figure 7B:
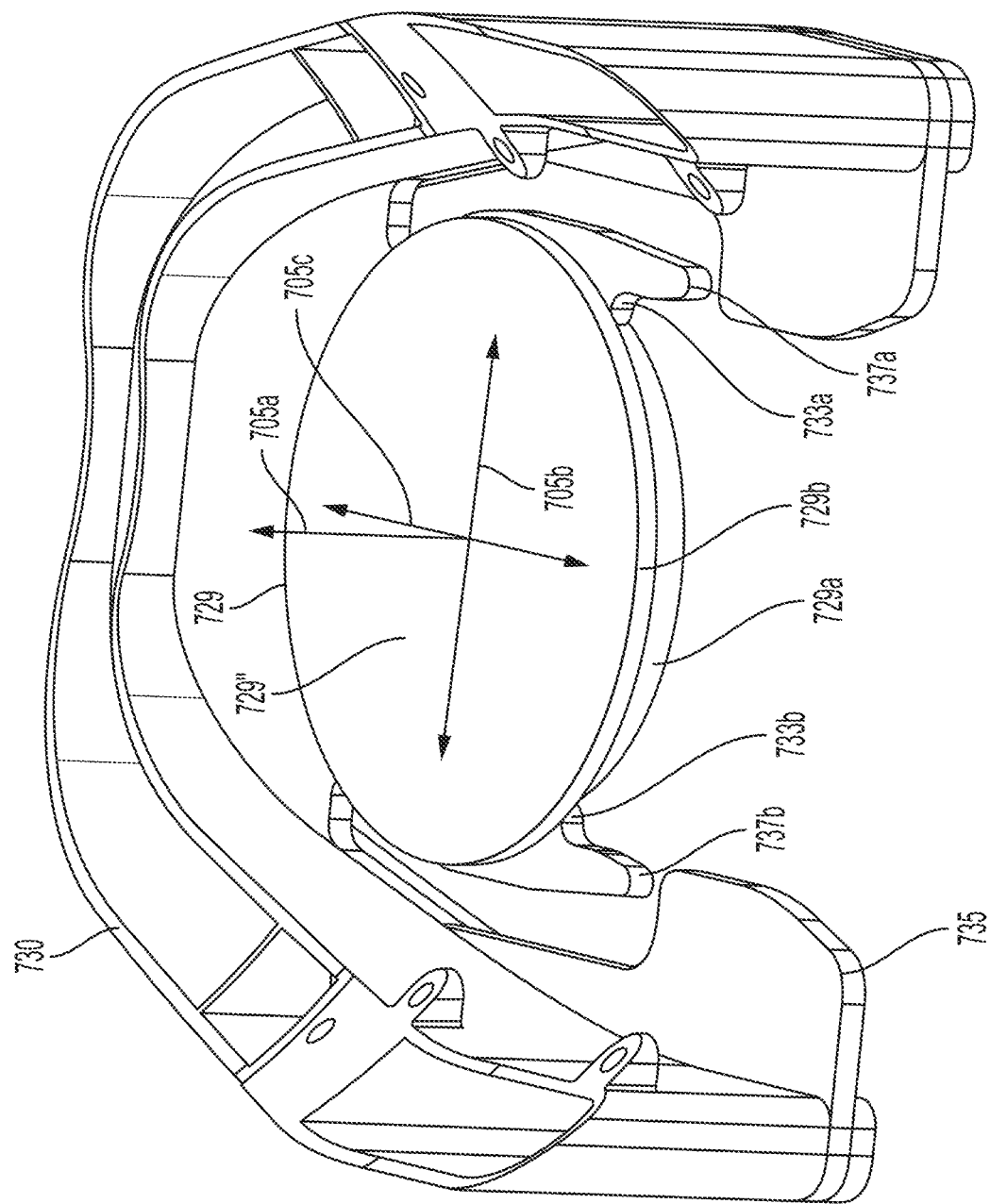

As discussed above, the view in FIG. 7A is of the underside of the radio frequency helmet 730 and member 729 so that surface 729' is visible. However, this surface is attached to the MRI system at a location so that when radio frequency helmet 730 is engaged with the member, the helmet and target anatomy of the patient are positioned with the imaging region of the MRI system (e.g., as shown in FIGS. 4A-4I). FIG. 7B illustrates a top view of releasable securing mechanism 735 engaged with member 729 of an MRI system. As shown, arm portions 737a and 737b fit underneath larger diameter portion 729b and protrusions 733a and 733b grip smaller diameter portion 729a. In this manner, larger diameter portion 729b prevents radio frequency helmet 730 from being lifted away from member 729. That is, larger diameter portion 729b restricts movement of radio frequency helmet 730 in the direction indicated by arrow 705a. In addition, arms 737a and 737b restrict movement of radio frequency helmet 730 in the directions illustrated by arrows 705b and 705c (securing mechanism 735 restricts movement of member 727 in the plane of the top surface 729" of member 729). While the resistance to movement of radio frequency helmet 730 out of securing mechanism 735 can be overcome by applying sufficient force to the helmet as discussed above, absent such a force, translational movement of radio frequency helmet 730 is generally prevented in all directions. However, releasable securing mechanism 735 may be configured to allow radio frequency helmet to be rotated about member 729 (e.g., about the axis along arrow 705a). By allowing radio frequency helmet 730 this degree of freedom, radio frequency coil can be oriented as desired about the center of the MRI system, providing flexibility as to the directions in which the patient can be inserted into the MRI system. According to some embodiments, an additional securing mechanism is provided to prevent rotation after a desired orientation has been reached, as discussed in further detail in connection with FIGS. 8A and 8B.

Figure 8A:
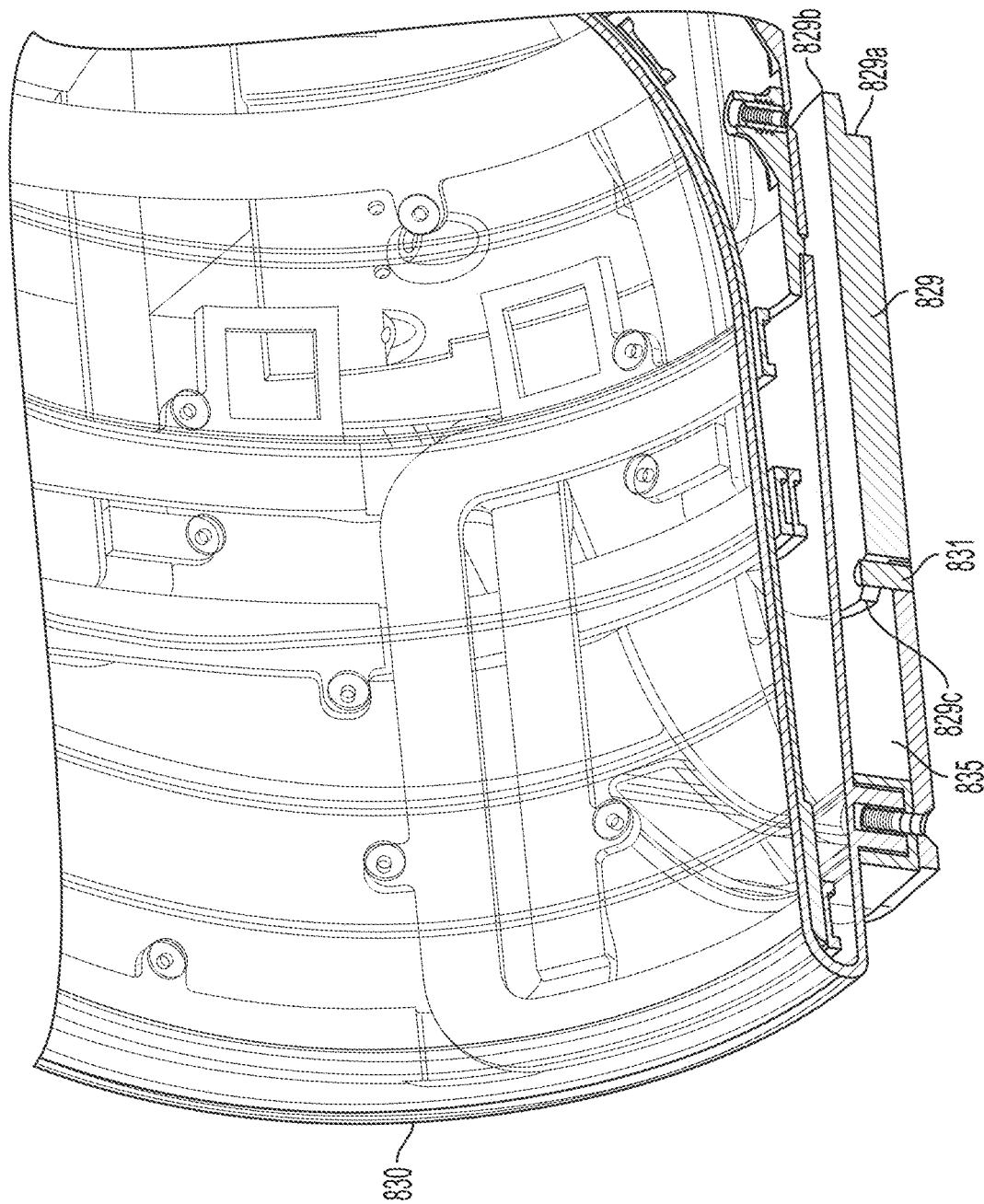
FIGS. 8A-B illustrate aspects of a releasable securing mechanism of a radio frequency coil apparatus, in accordance with some embodiments.
Figure 8B:
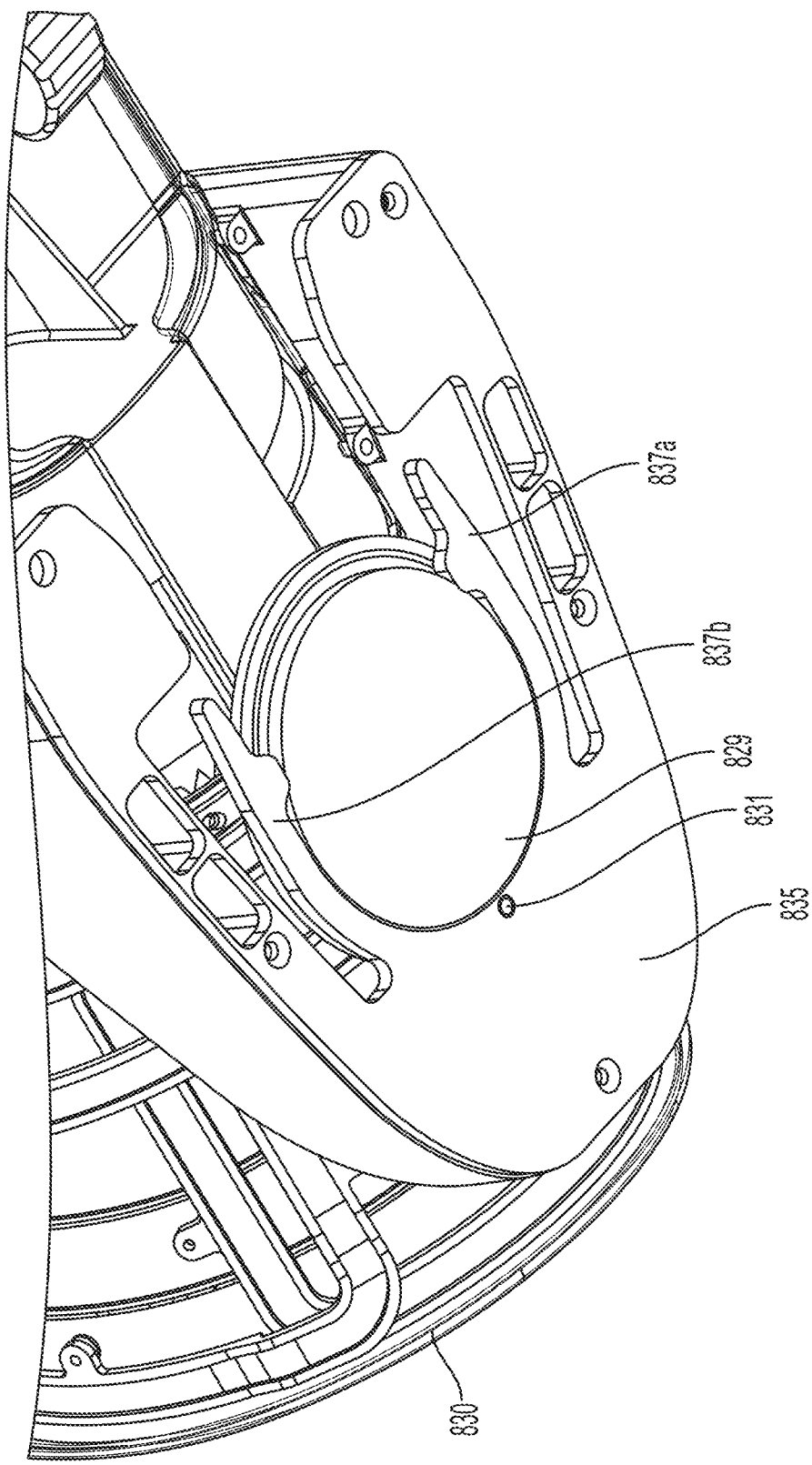

FIGS. 8A and 8B illustrate an example of a releasable securing mechanism that allows for rotation of the radio frequency coil apparatus about a securing member of the MRI system to provide the above discussed flexibility, and that comprises an additional securing mechanism to hold the radio frequency coil apparatus in place once a desired orientation has been reached, in accordance with some embodiments. FIG. 8A illustrates a cross-sectional view of a radio frequency helmet 830 comprising a releasable securing mechanism 835 configured to engage member 829 to secure the radio frequency helmet 830 to an MRI system. Releasable securing mechanism 835 may be similar to releasable securing mechanism 735 illustrated in FIGS. 7A and 7B. In particular, releasable securing mechanism 835 may include arm portions 837a and 837b (shown in FIG. 8B) configured to grip member 829 to resist translational movement of radio frequency helmet 830, but allow for rotation about member 829. In addition, a second securing mechanism 831 is provided to hold radio frequency helmet 830 at a particular orientation about the member 829. For example, securing mechanism 831 may be a peg, pin or post configured to cooperate with at least one recess 829c (e.g., a slot, notch or other recess) provided in larger diameter portion 829b of member 829. When radio frequency helmet 830 engages with member 829, the helmet can be rotated until the securing mechanism 831 finds recess 829c to hold the helmet at the fixed orientation of the recess. In this manner, helmet 830 can be secured to member 829 and quickly rotated and held in place at a corresponding desired orientation. It should be appreciated that member 829 may be provided with as many recesses around its perimeter as desired to allow a radio frequency helmet to be secured to an MRI system at the different corresponding orientations.

Figure 9A:
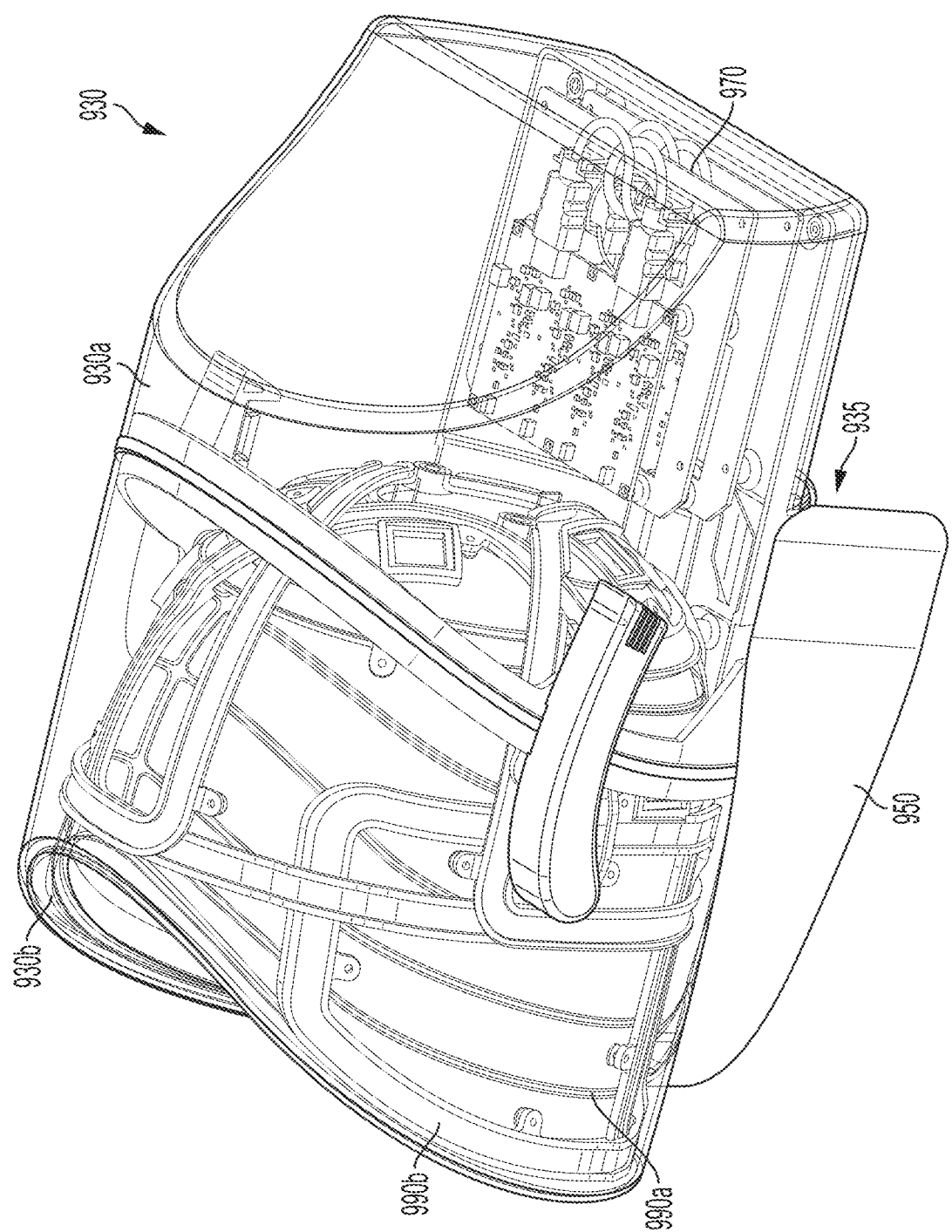
FIGS. 9A-B illustrate a see-through radio frequency helmet, in accordance with some embodiments.
Figure 9B:
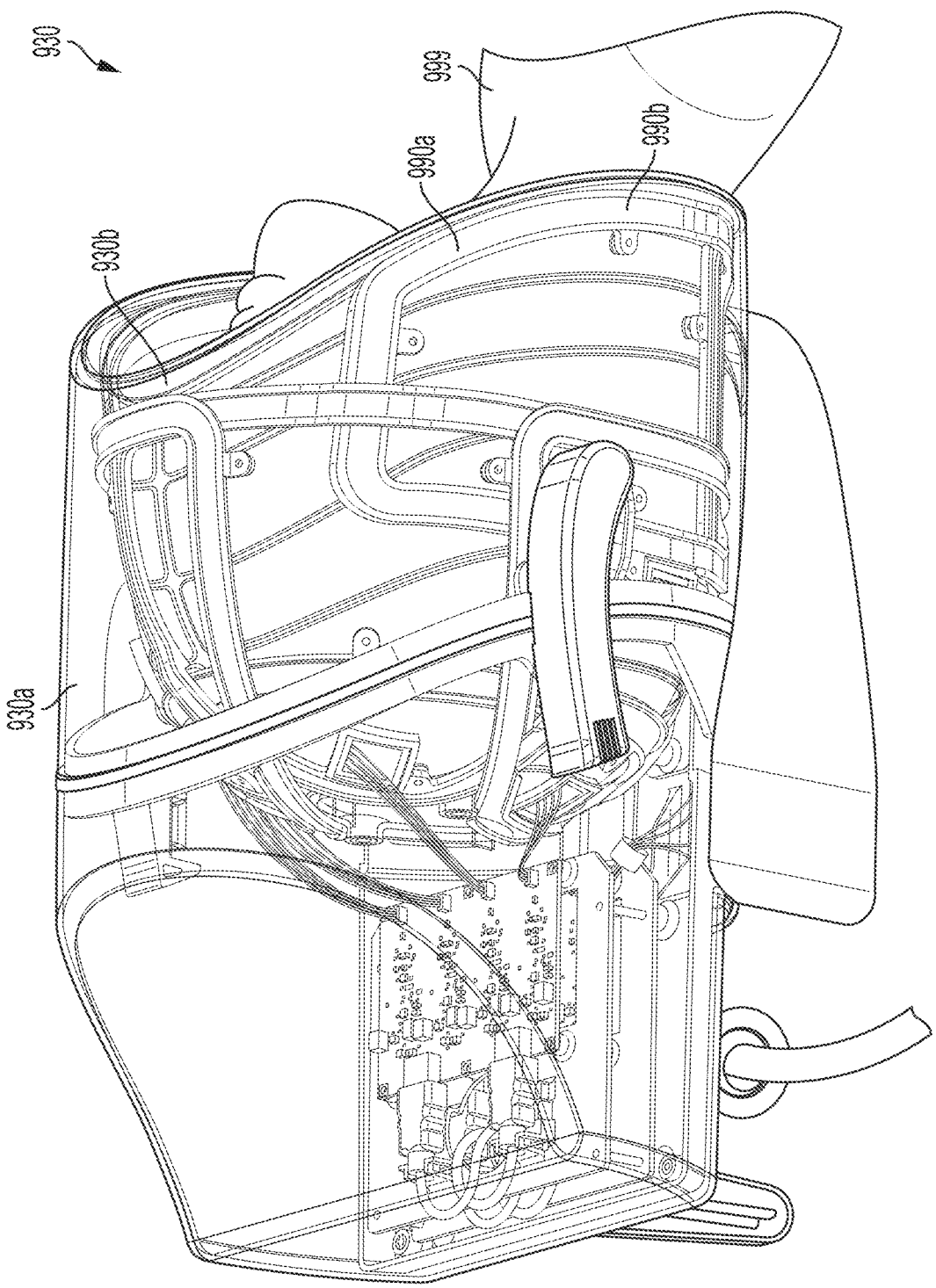

FIGS. 9A and 9B illustrate a see-through radio frequency helmet 930 to assist medical personnel in properly positioning a patient within helmet 930. According to some embodiments, helmet 930 comprises an outer housing 930a and a coil support 930b for transmit and/or receive coils, both made of see-through material. The term see-through refers to structure or material that is transparent or semitransparent (e.g., translucent) so that the location of a patient's head can be viewed through the helmet. That is, see-through material refers to material that is sufficiently transparent to allow medical personnel to visually assess whether a patient is positioned correctly by looking through the helmet. Coil support 930b may be adapted to accommodate a patient's head and provide a surface to which the transmit and/or receive coils are disposed. Exemplary coil support 930b provides a surface for transmit coil(s) 990a and receive coils 990b. It should be appreciated that any configuration or geometry of transmit and/or receive coils may be used, as the aspects are not limited in this respect.

Exemplary housing 930a may contain electronics 970 that are used in the operation of transmit/receive coils 930a and 930b, though such electronic may be positioned outside the housing, as the aspects are not limited in this respect. Housing 930a may be attached to base 950 comprising a releasable securing mechanism 935 according to any one or more of the techniques described herein to releasably secure helmet 930 to a magnetic resonance imaging system within the imaging region of the system. FIG. 9B illustrates a radio frequency helmet 930 with a patient 999 positioned within coil support 930b. Because outer housing 930a and coil support 930b are see-through (e.g., constructed from a transparent or semitransparent plastic material), the patient's head can be viewed through helmet 930, thus facilitating proper positioning of patient 999 within helmet 930. It should be appreciated that while exemplary helmet 930 comprises a housing and a coil support, this is not a requirement. For example, according to some embodiments, a radio frequency helmet may consist of a single surface on which transmit/receive coils are provided, and this surface may be made from see-through material to assist medical personnel in positioning a patient properly within the helmet.

As discussed above, techniques for providing a releasable securing mechanism may also be applied to a radio frequency coil apparatus comprising one or more radio frequency coils adapted to accommodate an appendage, such as a leg or an arm, or a portion of an appendage such as an ankle, foot, wrist, hand, etc. FIGS. 10A-D illustrate aspects of a foot coil adapted to accommodate a foot and configured to secure the foot coil to an MRI system so that the foot is positioned within the imaging region of the MRI system (e.g., within the imaging region of the exemplary low-field MRI systems described in the foregoing). According to some embodiments, a radio frequency apparatus is adapted to accommodate a foot and configured to be secured within the imaging region of an MRI system having a bi-planar $B_0$ magnet configuration in which the space between upper and lower $B_0$ magnets may be limited, some examples of which are described in further detail below.

Figure 10A:
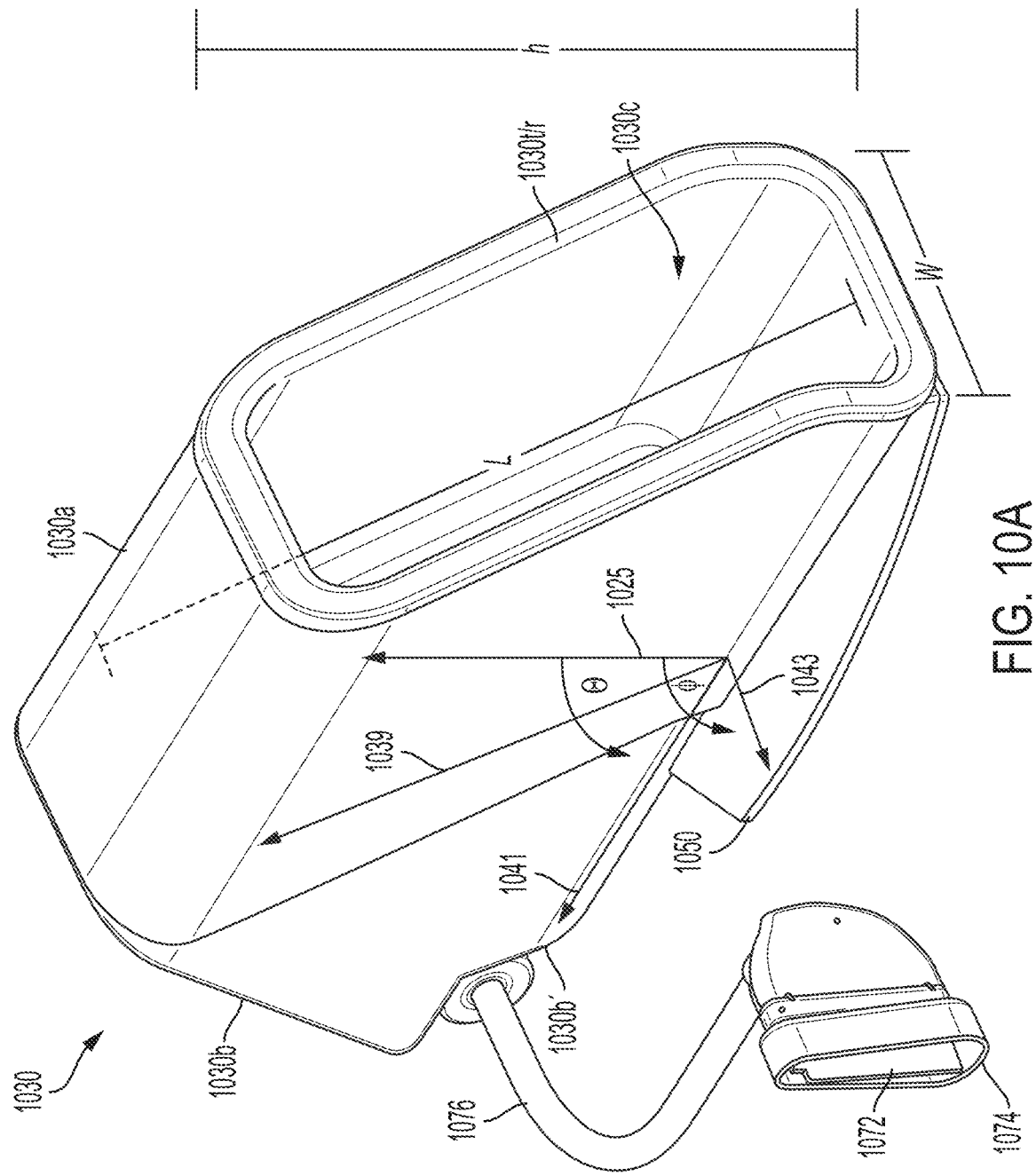
FIGS. 10-D illustrate view of a foot coil, in accordance with some embodiments.
Figure 10B:
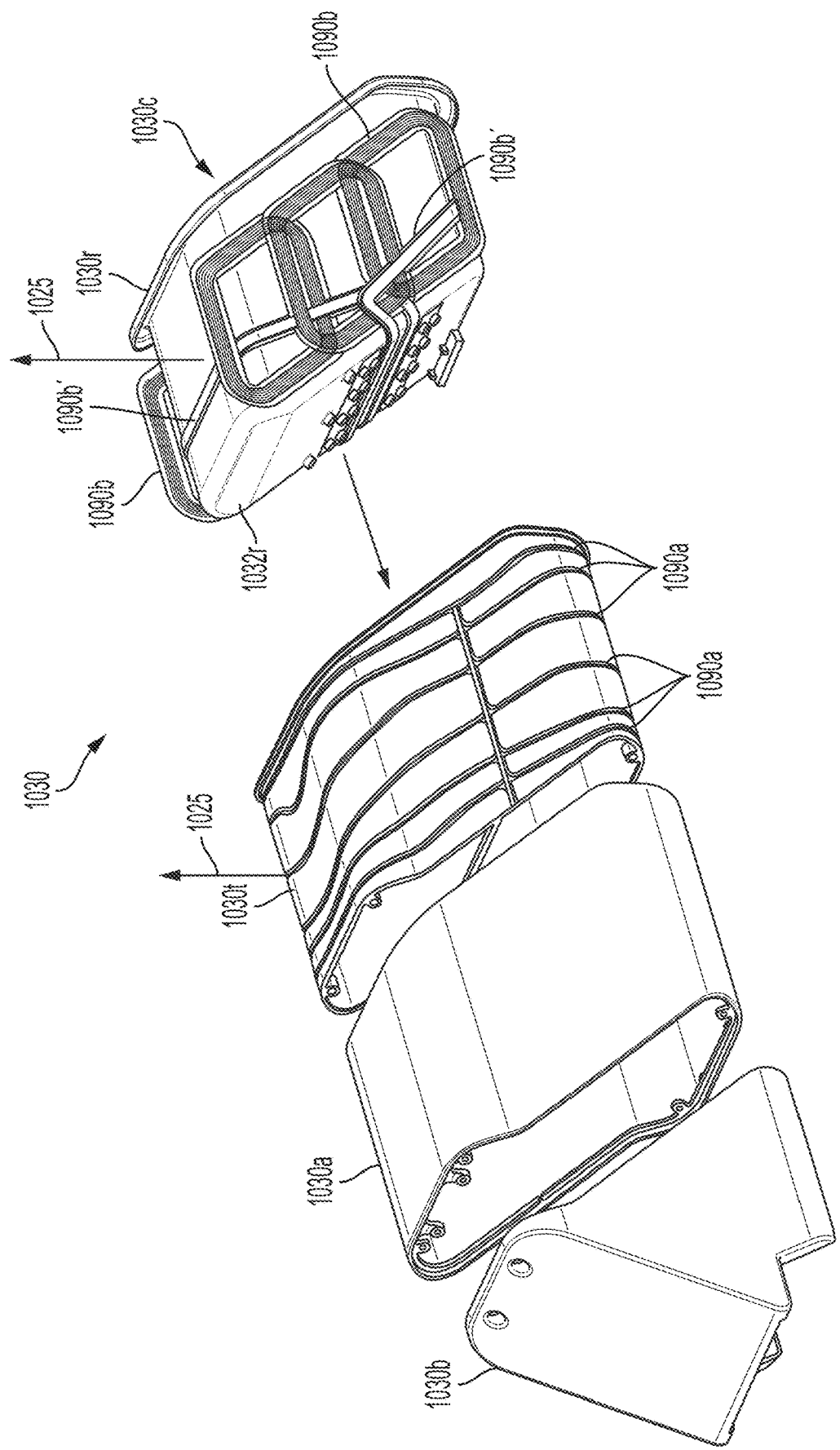
Figure 10C:
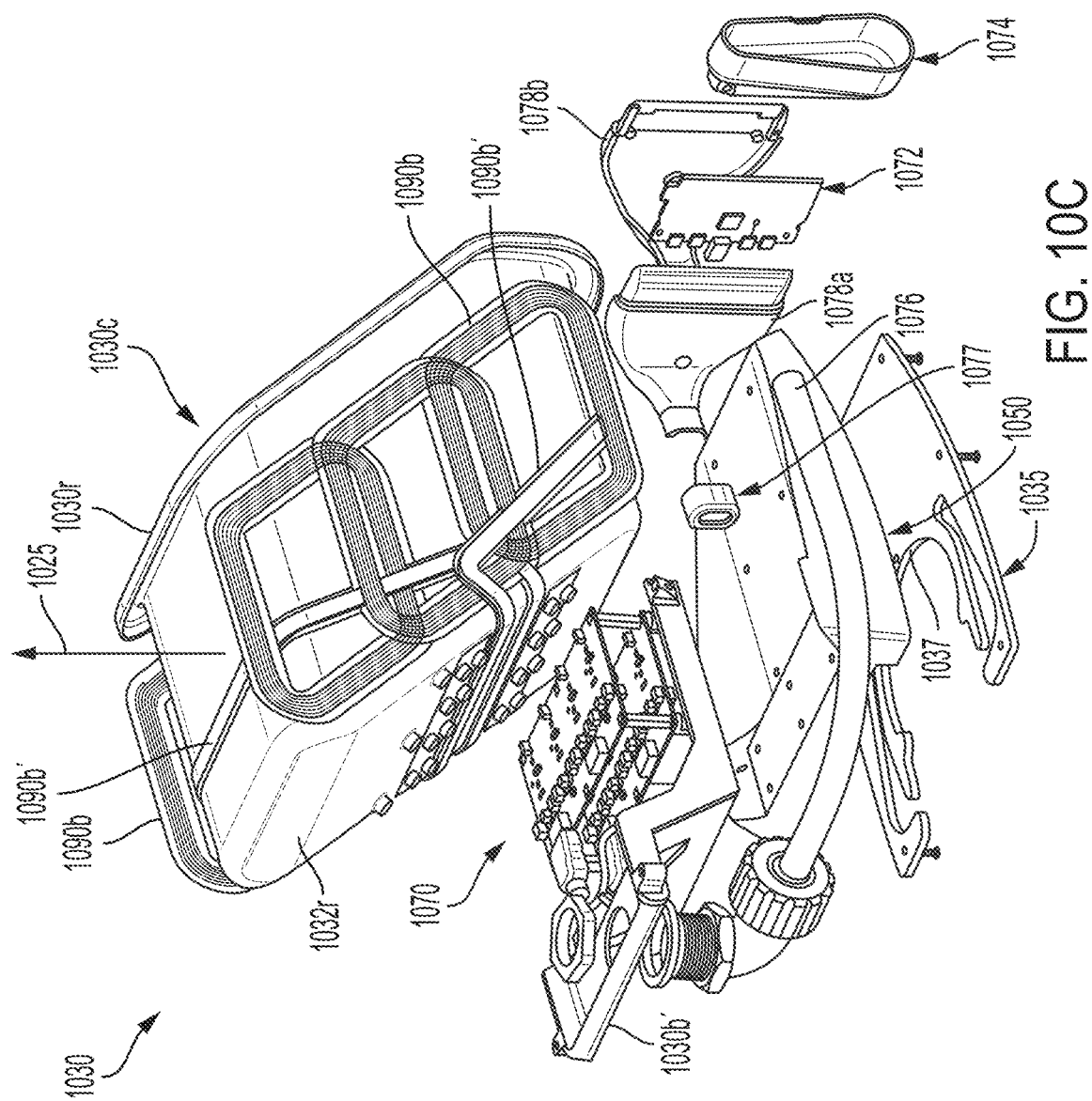

FIG. 10A illustrates a view of a radio frequency apparatus 1030 (referred to generally herein as a "foot coil," adapted to accommodate a foot for one or more MRI procedures. Foot coil 1030 comprises transmit/receive housings or supports 1030t/r on or within which transmit and/or receive coils for the radio frequency apparatus are provided. According to some embodiments, foot coil 1030 comprises a transmit housing for transmit coils and a receive housing for receive coils, examples of which are illustrated in FIGS. 10B and 10C, respectively, discussed in further detail below. According to some embodiments, the transmit and receive coils may be provided on or within the same housing (e.g., transmit coils and receive coils may be provided on the same side of a shared housing, on outer and inner sides of the same housing and/or one or more coils may be used for both transmit and receive), as the aspects are not limited in this respect.

Exemplary foot coil 1030 also comprises an outer housing 1030a to at least partially cover transmit/receive housing(s) 1030t/r and to form a volume 1030c adapted to accommodate a foot. As illustrated in FIG. 10A, volume 1030c has a height h and a w that allows a foot to be inserted into the interior of foot coil 1030. In the embodiment illustrated in FIG. 10A, foot coil 1030 is constructed at an angle θ relative to the vertical axis. The inventors have recognized that angling the foot coil relative to the vertical axis (e.g., generally pointing the toes away from the vertical axis) may provide a number of advantages over a vertical orientation. For example, a foot coil set at an angle relative to the vertical (i.e., with a podal axis greater than zero degrees) facilitates accommodating larger feet within the imaging region of the MRI system. In particular, the distance between the upper and lower $B_0$ magnets in the bi-planar configuration described in the foregoing places a limit on the height h of the foot coil (e.g., the distance D labeled in FIG. 4G constrains the height of the foot coil that can be accommodated by the MRI system). As shown in FIG. 10A, axis 1039 is tilted from vertical by an angle θ. Axis 1039, referred to herein as the podal axis, is the principal axis of the foot coil that is aligned with the foot when inserted into volume 1030c and the angle θ defines the angle of the podal axis away from the vertical axis 1025 in the direction of the longitudinal axis 1041. That is, the podal axis refers to the axis that is aligned in the direction from the bottom of the foot coil where the heel of the foot is positioned towards the toes of the foot when placed within the foot coil. A podal axis at zero degrees from the vertical axis 1025 in the direction of the longitudinal axis 1041 (i.e., θ=0°) is aligned with the vertical axis in this respect, and a podal axis of 90 degrees from the vertical axis 1025 in the direction of the longitudinal axis 1041 (i.e., θ=90°) is aligned with the longitudinal axis in this respect. Exemplary foot coil 1030 has a podal axis 1039 of approximately 45 degrees from the vertical axis in the direction of the longitudinal axis.

By angling the foot coil (i.e., tilting the podal axis away from the vertical axis), a longer foot can be accommodated within the imaging region of, for example, the exemplary MRI systems described herein (e.g., MRI systems having the bi-planar configuration shown in FIGS. 2-4). That is, the length of a foot that can be accommodated by the foot coil is greater than the height of the foot coil in the vertical direction (i.e., L>h as shown in FIG. 10A). The more that foot coil 1030 is angled relative to the vertical axis, the longer the foot that can be accommodated within the same vertical height (i.e., the greater the length L is relative to the height h). Because the human foot tends to rest with the toes pointed away from the vertical axis (i.e., rather than having the toes straight above the heal), a foot coil that generally mimics the natural repose of the foot may improve patient comfort during an imaging procedure. Specifically, the angled or tilted foot coil may obviate the need for the patient to orient and hold their foot straight up and down, which may cause discomfort or pain, particularly in circumstances where the foot is injured from disease, infection or trauma. Though large angles (e.g., angles between 60 and 75 degrees) may compromise the comfort of the patient in certain circumstances, such angles may be used to construct a foot coil capable of accommodating longer feet.

To accommodate even larger feet, the foot coil may additionally be tilted away from the vertical axis in a direction towards the latitudinal axis. That is, the podal axis may be tilted by an angle φ away from the vertical axis 1025 in the direction of latitudinal axis 1043 illustrated in FIG. 10A. The different tilt angles (i.e., tilt angles θ and φ) may be used alone or in combination to accommodate a wide variety of foot sizes. A podal axis at zero degrees from the vertical axis 1025 in the direction of the latitudinal axis 1043 (i.e., φ=0°) is aligned with the vertical axis in this respect, and a podal axis of 90 degrees from the vertical axis 1025 in the direction of the latitudinal axis 1043 (i.e., φ=90°) is aligned with the latitudinal axis in this respect.

It should be appreciated that the podal axis may be chosen as desired to suit the needs of the imaging application and/or the patient and multiple foot coils may be manufactured with different podal axes and dimensions to facilitate MRI of a wide variety of feet under differing circumstances and conditions. According to some embodiments, the foot coil is tilted relative to vertical in the direction of the longitudinal axis at an angle between 5 degrees and 60 degrees (i.e., a podal axis with an angle θ between 5 and 60 degrees), more preferably between 15 degrees and 50 degrees and, more preferably between 30 and 45 degrees (e.g., as illustrated by podal axis 1039 for exemplary foot coil 1030 illustrated in FIG. 10A). According to some embodiments, the foot coil is tilted relative to vertical in the direction of the latitudinal axis at an angle between 5 degrees and 60 degrees (i.e., a podal axis with an angle φ between 5 and 60 degrees), more preferably between 15 degrees and 50 degrees and, more preferably between 30 and 45 degrees, or at an angle of approximately zero degrees as illustrated in FIG. 10A. It should be appreciated that a foot coil may be tilted to have a θ component, a φ component, or both. As discussed above, it should be appreciated that different foot coils may be constructed at different angles to accommodate a wide variety of feet under a wide variety of different conditions and circumstances, and the exemplary podal axis and dimensions described herein are not limiting.

Foot coil 1030 also comprises back portion 1030b that houses the electronics for the foot coil when connected with bottom portion 1030b'. For example, the electronics forming portions of the radio frequency signal chain (e.g., the transmit/receive circuitry) for operating the transmit and receive coils may be housed in back portion 1030b, 1030b', as discussed in further detail below. Bottom portion 1030b' further comprises a terminal connection for cable bundle 1076 which carries power, control and/or data (e.g., MR signal data) from the MRI system to the transmit/receive circuitry housed in the back portion. In the embodiment illustrated in FIG. 10A, the interface to the MRI system comprises board 1072 for providing power, control and/or data between the radio frequency apparatus and the MRI system and an adapter 1074 constructed to prevent board 1072 from being connected to the MRI system in an incorrect orientation. In this manner, foot coil 1030 can be easily and simply connected to, operated by, and disconnected from the MRI system. Foot coil 1030 further comprises a base 1050 coupled to a releasable mechanism that allows the foot coil to engage with and disengage from the MRI system. For example, as described in further detail in connection with FIGS. 10C and 10D, base 1050 may be affixed to or otherwise coupled to a releasable mechanism that engages with a cooperating member situated within the imaging region of the MRI system.

FIG. 10B illustrates another view of foot coil 1030 showing the nested structure of the exemplary foot coil. In particular, FIG. 10B illustrates receive housing 1030r and transmit housing 1030t before insertion into outer housing 1030a. In the exemplary foot coil illustrated in FIG. 10B, receive coil housing 1030r (which supports receive coils 1090b, 1090b' described below) is configured as the inner most housing providing the volume 1030c adapted to accommodate the foot. Transmit housing 1030t is adapted to fit over received housing 1030r and the nested transmit/receive housing 1030t/r is configured to be inserted into outer housing 1030a. However, it should be appreciated that the order of the nesting may be switched and/or a single housing may be provided to support or carry both the transmit and receive coils, as discussed in further detail below.

As visible in the view shown in FIG. 10B, transmit coil(s) 1090a are provided on transmit housing 1030t and, more particularly, provided on an outside surface of the transmit housing. Alternatively or additionally, transmit coil(s) 1090a may be provided on an inner surface of transmit housing 1030t, provided in grooves or contours fabricated into the housing or otherwise integrated into transmit housing 1030t. Transmit coil(s) 1090a may comprise one or more conductors arranged in a three-dimensional geometry about volume 1030c to produce radio frequency pulses configured to cause MR signals to be emitted from a patient's foot positioned within volume 1030c when foot coil 1030 is engaged with and operated by the MRI system. According to some embodiments, transmit coil 1090a comprises a single conductor provided about transmit housing 1030t in a number of turns over one or more surfaces of the transmit housing. Alternatively, transmit coil 1090a may comprise multiple separate conductors provided over one or more surfaces of transmit housing 1030t.

In the embodiment illustrated in FIGS. 10A-D, transmit coil(s) 1090a operate as transmit only coils and the receive coils are provided as a separate receive coil array, as discussed in further in detail in connection with FIG. 10C. However, according to some embodiments, radio frequency coil(s) 1090a may also operate as one or more receive coils configured to detect MR signals emitted from a foot being imaged in response to a selected pulse sequence produced, at least in part, by the same coils operating in transmit mode. In such embodiments, radio frequency coil(s) 1090a operate as transmit and receive coils. The geometry of transmit coil(s) 1090a (e.g., the relative spacing of the turns, the geometry of the contours, etc., may be determined to generally optimize characteristics of the radio frequency pulses emitted based on the geometry of volume 1030c using, for example, any of the techniques described in U.S. Patent Publication No. 2016/0334479, published Nov. 17, 2016 and titled "Radio Frequency Coil Methods and Apparatus." For example, a magnetic model may be used to determine a geometry for transmit coil(s) 1090a that generally optimize the magnetic pulses delivered to volume 1030c.

As discussed above, receive housing 1030r may be configured to fit within transmit housing 1030t. As visible in the view shown in FIG. 10B, a plurality of receive coils 1090b and 1090b' configured to detect magnetic resonance signals emitted from the foot of a patient in response to radio frequency pulses emitted by the transmit coils (e.g., transmit coil(s) 1090a) are provided on receive housing 1030r. As with the transmit coils, receive coils may alternatively or additionally be provided on an inner surface of receive housing 1030r or otherwise integrated within the housing. In the embodiment illustrated in FIGS. 10B and 10C, the receive coils comprise eight separate receive coils; six receive coils 1090b (e.g., three overlapping receive coils on each side of receive housing 1030r) and two receive coils 1090b' (e.g., a receive coil provided at least partially on top and bottom portions of the receive housing).

In the exemplary configuration illustrated in FIGS. 10B and 10C, the receive coils 1090b are positioned in an overlapping arrangement to reduce the inductive coupling between the coils. Spatially, receive coils 1090b are stacked in the vertical direction (e.g., in the direction of the $B_0$ magnetic field illustrated generally by arrow 1025) with the same characteristic tilt of the foot coil. That is, the receive coils may be aligned with the podal axis of the foot coil so that each successive receive coil is offset from the adjacent receive coil in a horizontal direction (e.g., in the longitudinal direction. With this arrangement, receive coils are configured to detect MR signals emitted from a patient's foot in directions along an axis orthogonal to the $B_0$ magnetic field generated, for example, by the exemplary MRI systems illustrated and described in the foregoing. Receive coils 1090b' are positioned on the top and bottom sides of receive housing 1030r to generally detect magnetic resonance imaging signals emitted in directions along another axis orthogonal to the $B_0$ magnetic field. In this manner, the receive coils can be configured approximately as quadrature coils to generally optimize the detection of MR signals. It should be appreciated that receive coils 1090b and 1090b' are merely exemplary and any number of coils in any suitable arrangement may be used, as the aspects are not limited in this respect.

As shown in FIG. 10C, receive housing 1030r includes a backside 1032r having electronic connections to electronics 1070 on bottom portion 1030b' that, when connected, allow power, control and/or data (e.g., MR signal data) to be exchanged between the MRI system and the foot coil (e.g., between the MRI system and transmit coils 1090a and receive coils 1090b, 1090b'). Specifically, power, control and/or data may be exchanged via the connection cable 1076 and board 1072 when adapter 1074 is connected to the MRI system in the manner discussed above in connection with FIG. 10A.

The view in FIG. 10C shows base 1050 that supports the radio frequency coil housings and releasable securing mechanism 1035 that, when assembled, is coupled to the bottom of base 1050. According to some embodiments, releasable securing mechanism 1035 includes a retention portion 1037 configured to grip a cooperating member affixed to the MRI system within the imaging region in a manner similar to or the same as the securing mechanism discussed above in connection with the radio frequency helmet described in FIGS. 7A-B and 8A-B. An example of one embodiment of securing mechanism 1035 is described in further detail in connection with the bottom view of foot coil 1030 illustrated in FIG. 10D.

Figure 10D:
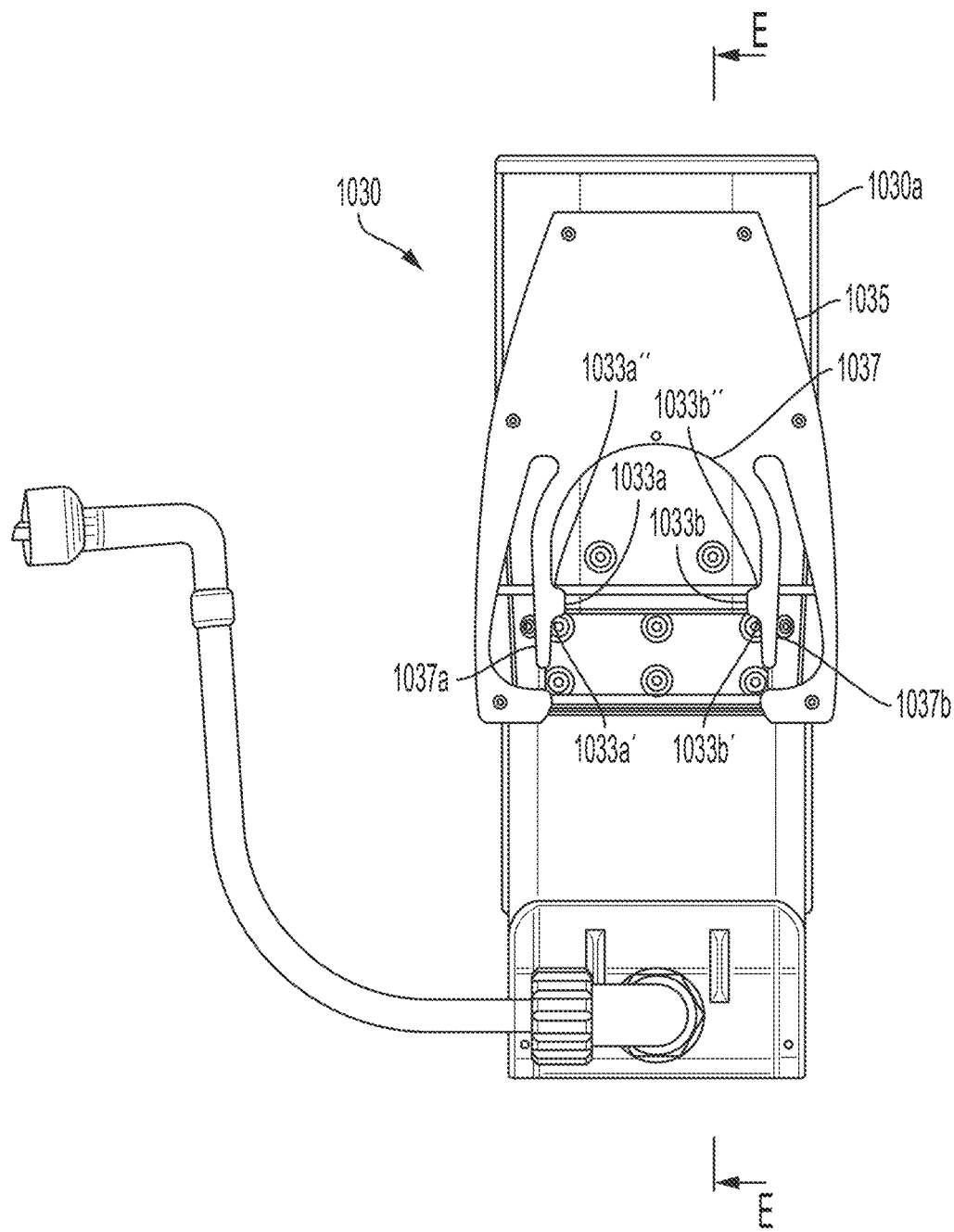

FIG. 10D illustrates a bottom view of foot coil 1030 showing securing mechanism 1035 configured to engage directly with an MRI system equipped with a cooperating member to secure foot coil 1030 within the imaging region of the MRI system, in accordance with some embodiments. In particular, in the embodiment illustrated in FIG. 10D, the outer housing 1030a may be coupled to base 1050 which in turn may be coupled to releasable securing mechanism 1035 configured to engage with and grip a cooperating member (e.g., member 729 illustrated in FIGS. 7A and 7B) attached to the MRI system at a location so that, when foot coil 1030 is engaged with the cooperating member, foot coil 1030 is positioned within the imaging region of the MRI system. In this manner, a patient's foot positioned within foot coil 1030 when attached to the MRI system is properly positioned for imaging.

Exemplary releasable securing mechanism 1035 comprises a circular receptacle portion dimensioned to accommodate the cooperating member attached to the MRI system and a retention portion 1037 configured to resist movement of the cooperating member once the member has been positioned within the receptacle. Exemplary retention portion 1037 comprises two arm portions 1037a and 1037b, respectively forming a portion of the receptacle and configured to grip the cooperating member when positioned within the receptacle. According to some embodiments, arm portions 1037a and 1037b include protrusions 1033a and 1033b, respectively, configured to resist movement of the cooperating member after it has been inserted into the receptacle of releasable securing mechanism 1035. Protrusions 1033a and 1033b comprise respective outward facing sides 1033a' and 1033b' and respective inward facing sides 1033a" and 1033b" dimensioned to facilitate securing the cooperating member of the MRI system to foot coil 1030.

According to some embodiments, the angle of the outward facing sides of protrusions 1033a and 1033b and the angle of the inward facing sides of the protrusions are configured such that less forced is required to allow the cooperating member to enter into the receptacle of securing mechanism 1035 than is required to allow the cooperating member to exit the receptacle (e.g., it requires less force to engage with the cooperating member than to disengage with the cooperating member). For example, as discussed above in connection with radio frequency helmet 735, the relative angles of the outward and inward facing sides may be selected so that a relatively small force on the outward facing sides is needed to part arm portions 1037a and 1037b to allow the cooperating member to enter the receptacle of releasable securing mechanism 1035 and a larger force on the inward facing sides is needed to part arm portions 1037a and 1037b to allow foot coil 1030 to be released from the cooperating member (e.g., to allow the cooperating member to be released from the receptacle of securing mechanism 1035).

It should be appreciated that protrusions 1033a and 1033b may be dimensioned in any way so that desired forces achieve engaging and disengaging securing mechanism 1035 with the cooperating member, as the aspects are not limited in this respect. Thus, foot coil 1030 can be secured to and released from the MRI system by applying a force in the appropriate direction. That is, securing mechanism 1035 is releasable because following engagement of arm portions 1037a and 1037b with the cooperating member, foot coil 1030 can released by providing sufficient force on the foot coil so that the cooperating member forces the arm portions 1037a and 1037b outward and releases the foot coil from the cooperating member. According to some embodiments, the cooperating member is similar to or the same as member 829 illustrated in FIGS. 8A and 8B that includes a recess (e.g., recess 829c) and the securing mechanism 1035 includes a pin or post (e.g., similar to or the same as pin 831 illustrated in FIGS. 8A and 8B) so that the foot coil can be rotated about the cooperating member until the pin finds the recess and prevents further rotation.

Figure 11:
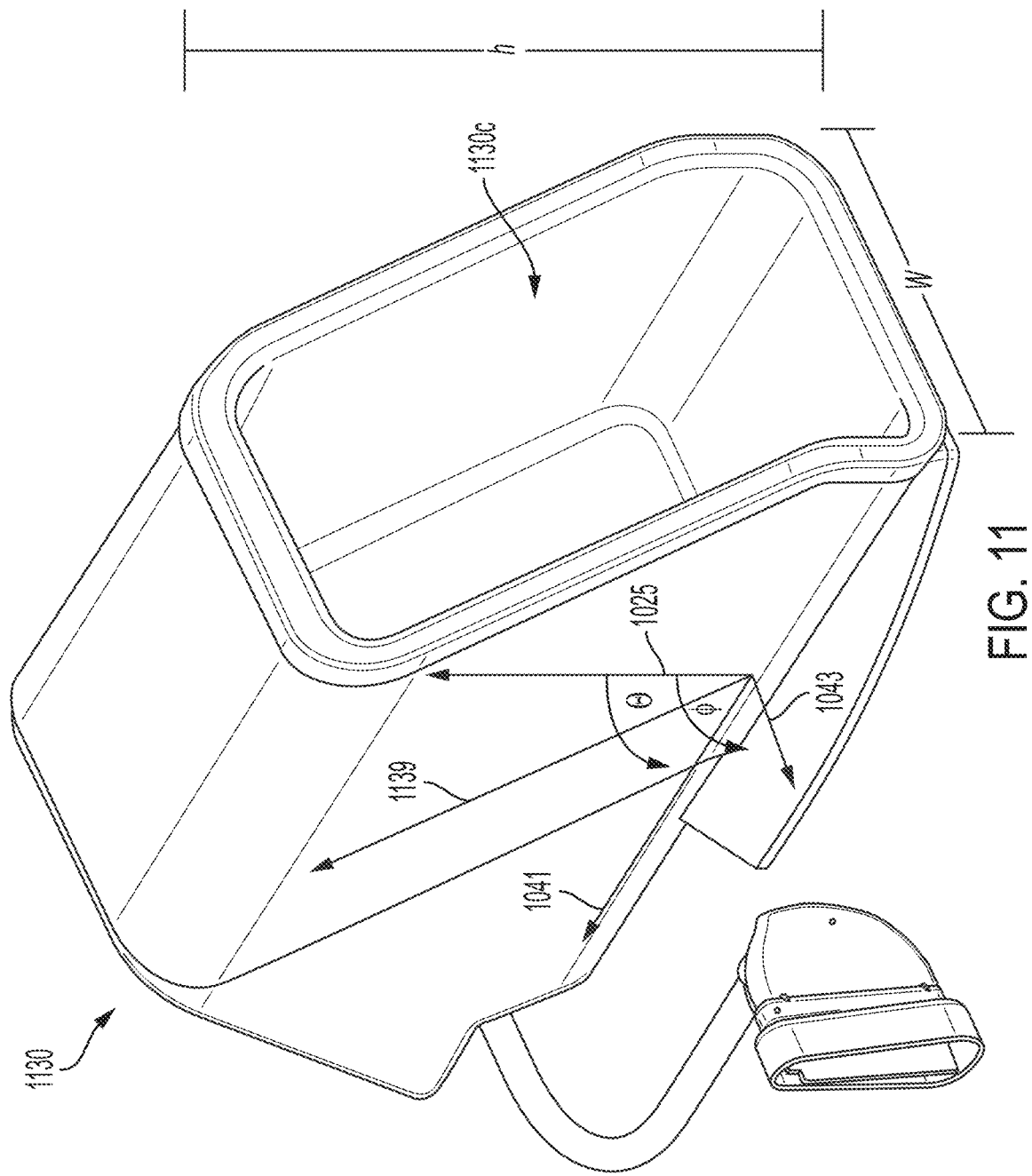
FIG. 11 illustrates a foot coil configured to accommodate a wider foot, in accordance with some embodiments.

FIG. 11 illustrates a foot coil adapted for a larger foot, for example, a swollen foot resulting from disease such as diabetes or complications that causes edema (e.g., congestive heart failure, kidney or liver disease, etc.), swelling that results from infection or trauma, or the foot of a larger person. Foot coil 1130 may be similar in many respects to foot coil 1030 illustrated in FIG. 10A. However, foot coil 1130 is constructed to have a width W that is greater than the width w of coil 1030 illustrated in FIG. 10A to accommodate a larger foot and, more particularly, a larger width foot characteristic of disease or edema, thus providing a larger volume 1130c for the foot coil 1130. As discussed above, the angle at which foot coil is tilted relative to vertical may be selected based on patient comfort, to accommodate larger feet, to accommodate other circumstances or imaging conditions, etc. Similarly, the podal axis of foot coil 1130 illustrated in FIG. 11 may also be varied for comfort and/or to accommodate longer feet. Similarly, different foot coils may be manufactured at different angles so that a wide variety of patients and imaging conditions can be accommodated.

Figure 12A:
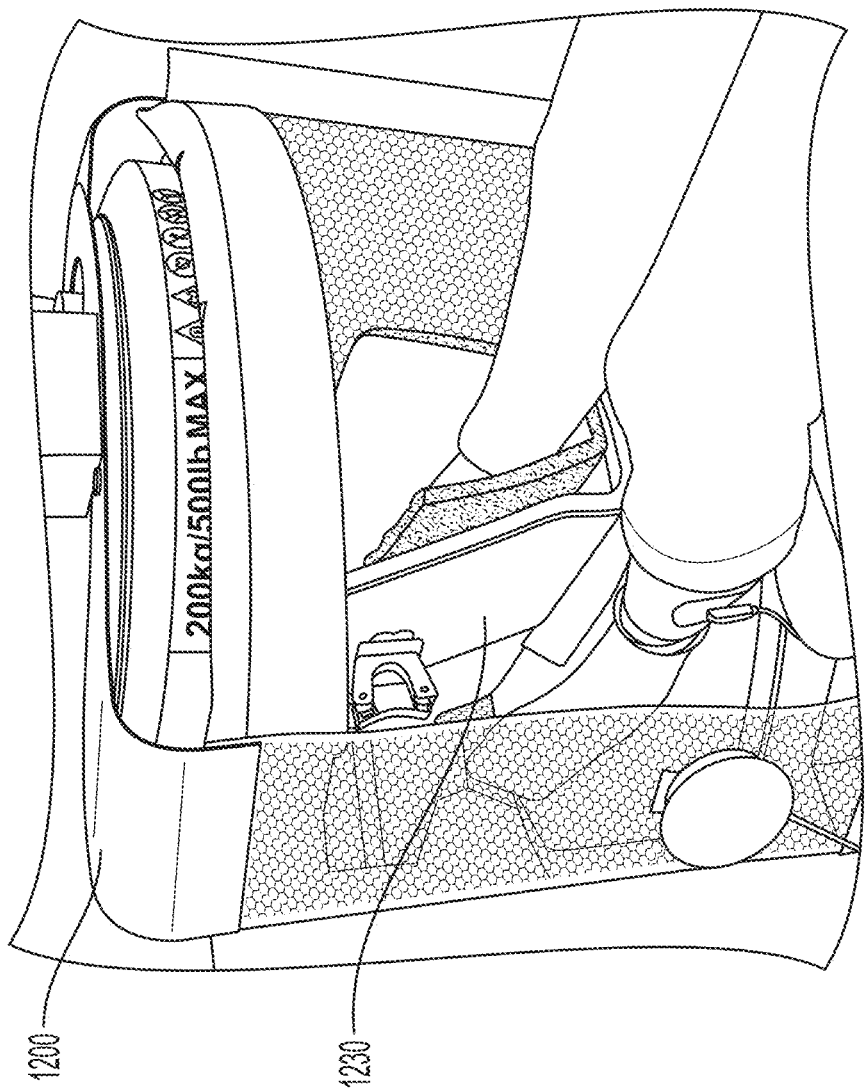
FIGS. 12A-D illustrate a foot coil positioned within a magnetic resonance imaging device, in accordance with some embodiments.
Figure 12B:
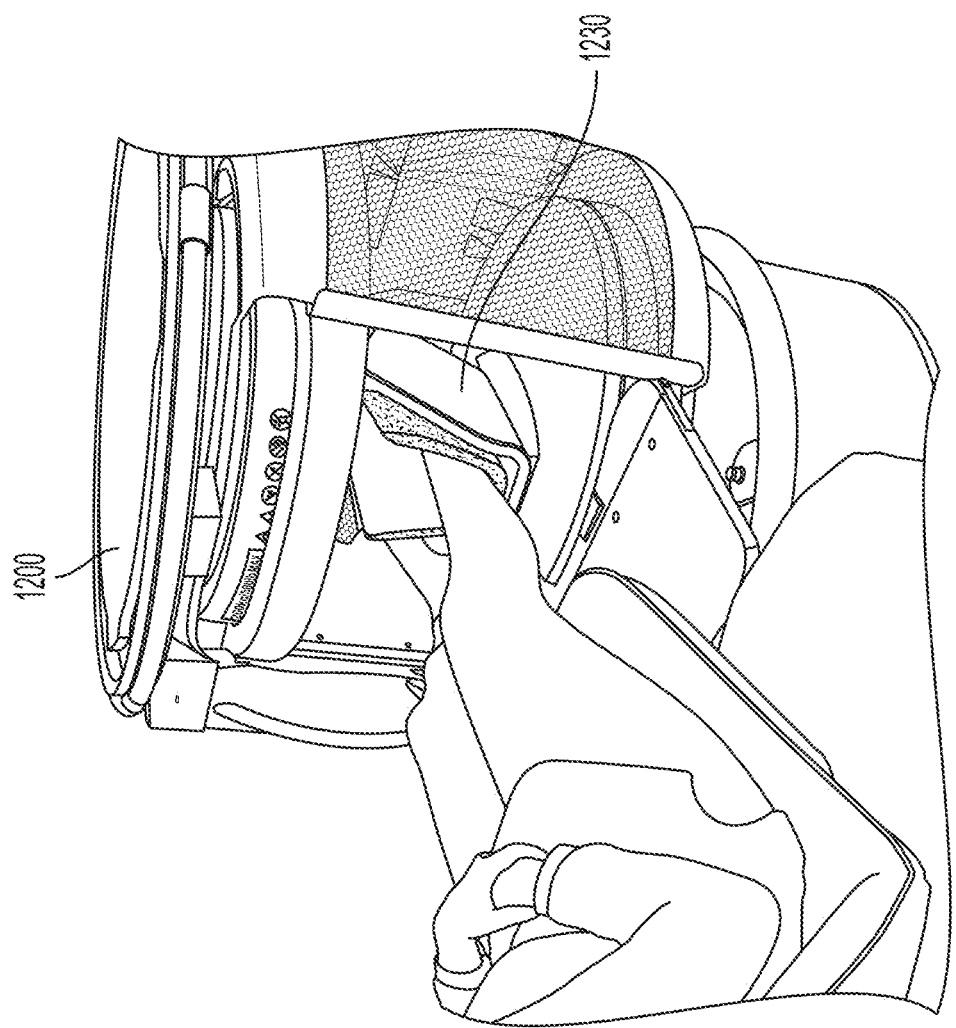
Figure 12C:
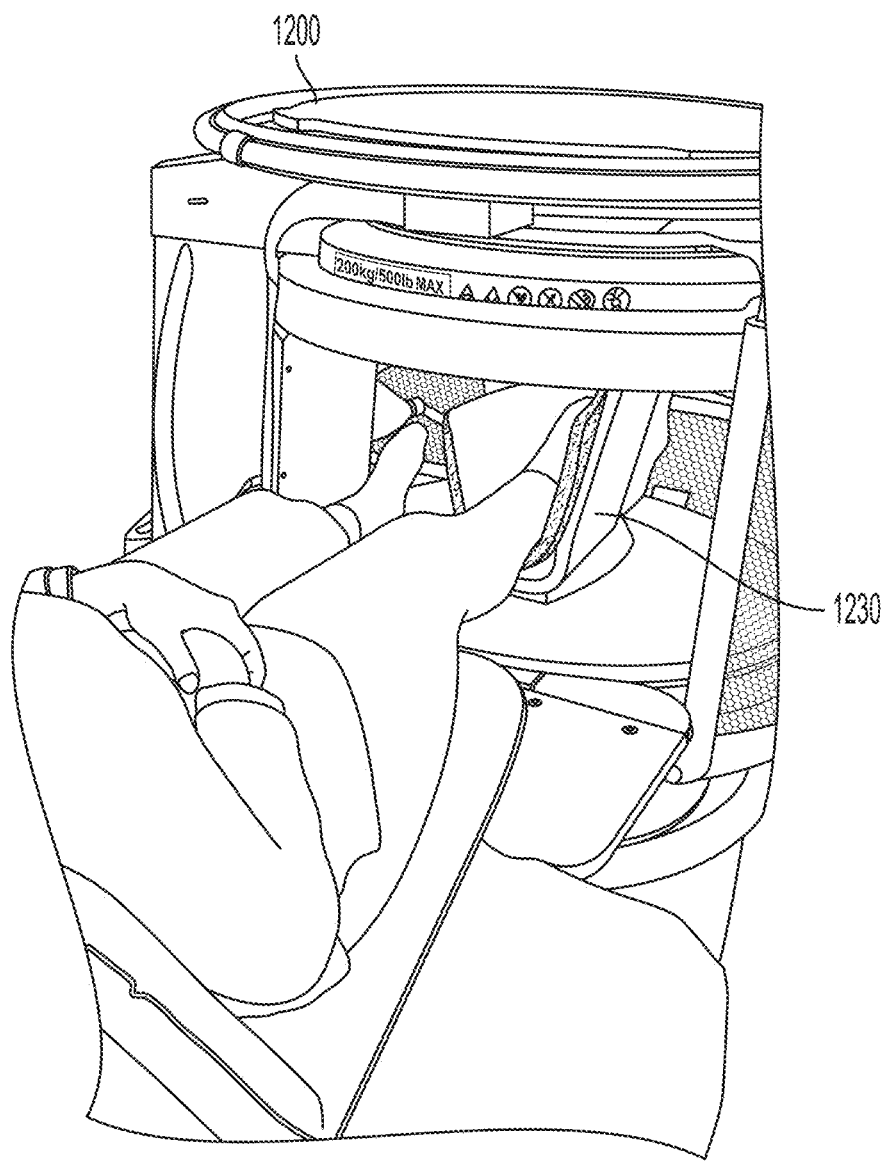
Figure 12D:
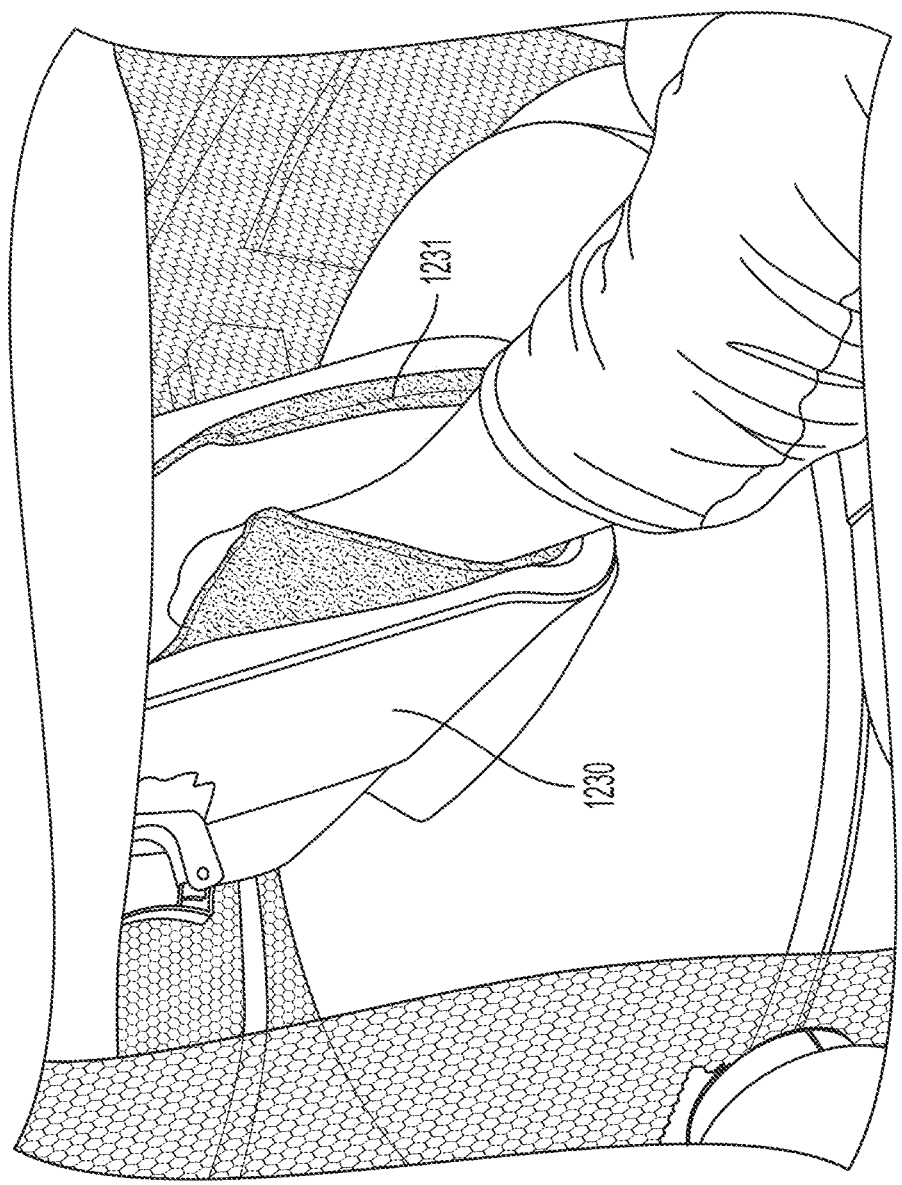

FIG. 12A illustrates a foot coil 1230 engaged with a cooperating member of MRI system 1200 so that the foot coil 1230 and the right foot positioned therein is within the imaging region of MRI system 1200 and positioned correctly for imaging. FIGS. 12B and 12C illustrate different views of the foot coil 1230 positioned with MRI system 1200. FIG. 12D illustrates foot coil 1230 accommodating the left foot. Also, FIG. 12D shows support 1231 (also visible in FIGS. 12A-12C) inserted within foot coil 1230 to support and provide comfort to the foot during an imaging procedure.

As discussed above, imaging a patient using MRI from, for example, a standard hospital bed typically requires positioning target anatomy of the patient within an MRI system located proximate the hospital bed on which the patient is lying. As discussed in connection with FIGS. 4A-I, the inventors have developed techniques for facilitating the positioning of a patient within the MRI system for imaging of desired anatomy of the patient from the patient's bed. For example, FIG. 4A illustrates a portable low-field MRI system 400 that has been moved into position proximate a standard hospital bed 490 to perform MRI on a patient 499 who may be confined to the bed for convenience, comfort or stabilization and/or because the patient is unconscious, immobilized or otherwise is not ambulatory or cannot be safely moved. Portable MRI system 400 may be a local installation deployed in an emergency room, operating room, intensive care unit, doctor's office, etc. that can be moved to bed 490, or in some cases, bed 490 can be wheeled to the MRI system. As discussed in detail in the foregoing, because of the low-field strengths of MRI system 400, bed 490 can be safely positioned in close proximity to MRI system 400.

To bridge the gap between bed 490 and MRI system 100, the MRI system may be equipped with a bridge 473 mounted to MRI system 100 to facilitate positioning patient 199 within the imaging region of MRI system 100. Specifically, bridge 473 provides a surface 474 over which patient 499 can be moved so that the patient's anatomy being imaged (e.g., the patient's head) can be positioned within the imaging region of the MRI system. However, the inventors have recognized that exemplary bridge 473 illustrated in FIG. 4A may be improved in a number of ways. For example, bridge 473 may be designed to work in cooperation with patient support 440 so that as long as the bridge 473 has dimension suitable to allowed the patient support to be transitioned over its surface, the dimensions of the bridge are sufficient. However, in some embodiments, a patient may be positioned within MRI system 400 without the assistance of a patient support. In such embodiments, it may be preferable to employ a larger dimensioned bridge both to facilitate ease and comfort of positioning the patient and to accommodate larger and heavier patients. The inventors have developed bridges adapted to facilitate patient positioning that are generally optimized for use either with or without a patient support.

As illustrated in FIG. 4A, fixed bridge 473 protrudes out from the MRI system, thereby increasing the footprint of the system. As a result, navigating the MRI system down hallways and through doorways is more difficult. Additionally, the useable surface of bridge 473 is limited and the construction of the bridge may not be suitable for heavier patients, particularly in cases where the patient is being positioned without the aid of a patient support. As a result, bridge 473 may be difficult to use with larger and/or heavier patients and may not be rated to support the heaviest patients. However, increasing the dimensions of the bridge to facilitate patient positioning without a patient support and/or to support heavier or larger patient, results in a bridge that protrudes even further from the MRI system and requires more robust construction.

The inventors have recognized the benefits of patient support bridge capable of supporting larger and heavier patients and have appreciated the benefits of such a bridge that can accommodate a range of gaps between the MRI system and a patient bed and/or that provide more overlap between the bridge and the bed. Specifically, for patient comfort, safety and/or to facilitate more convenient positioning of a patient, particularly larger and/or heavier patients, it is desirable to equip a portable MRI system with relatively large dimensioned bridges capable of safely supporting a wide range of patients. However, there are a number of issues associated with the design and development of relatively large dimensioned bridges capable of supporting the weight of larger patients.

For example, as mentioned above, larger bridges increase the footprint of the MRI system even further, making it more difficult (or impossible) to transport the MRI system down hallways and to fit the MRI system through the doorways of the health care facilities in which they are deployed. To address the problem of increased footprint for the MRI system, the inventors have developed a fold-out bridge that can be folded-down to facilitate positioning the patient within the imaging region of the MRI system and to support the patient during an imaging procedure and that can be folded-up during transport of the MRI system so that the MRI system can be more easily moved down hallways and through doorways to the patient.

Additionally, providing a bridge capable of safely supporting larger, heavier patients requires robust construction. Typically, such patient supports would be constructed using large amounts of metal material capable of withstanding the significant stresses resulting from supporting the weight of heavier patients. However, significant quantities of metal may negatively impact the operation of the magnetic resonance imaging system to which the bridge is attached by distorting the main magnetic field and/or producing substantial eddy currents during operation of the magnetic resonance imaging system that negatively impact image quality. To mitigate this problem, some embodiments include a fold-up bridge in which the metal composition of the bridge is minimized to the extent possible to provide a bridge capable of supporting heavier patient while minimizing the impact on the operation of the magnetic resonance imaging system. Thus, the exemplary fold-up bridges described herein may be capable of supporting large and/or heavy patients safely and securely, thus taking advantage of the benefits of larger dimensioned bridges without significantly impacting the ability to move the MRI system down hallways and through doorways.

Following below are more detailed descriptions of various concepts related to, and embodiments of, a fold-out bridge that can be moved from a vertical position for stowing during transport of a portable low-field MRI system or when the MRI system is not in use to a horizontal position to facilitate positioning of the patient for point-of-care MRI. It should be appreciated that the embodiments described herein may be implemented in any of numerous ways. Examples of specific implementations are provided below for illustrative purposes only. It should be appreciated that the embodiments and the features/capabilities provided may be used individually, all together, or in any combination of two or more, as aspects of the technology described herein are not limited in this respect or to the specific combinations described.

Figure 13A:
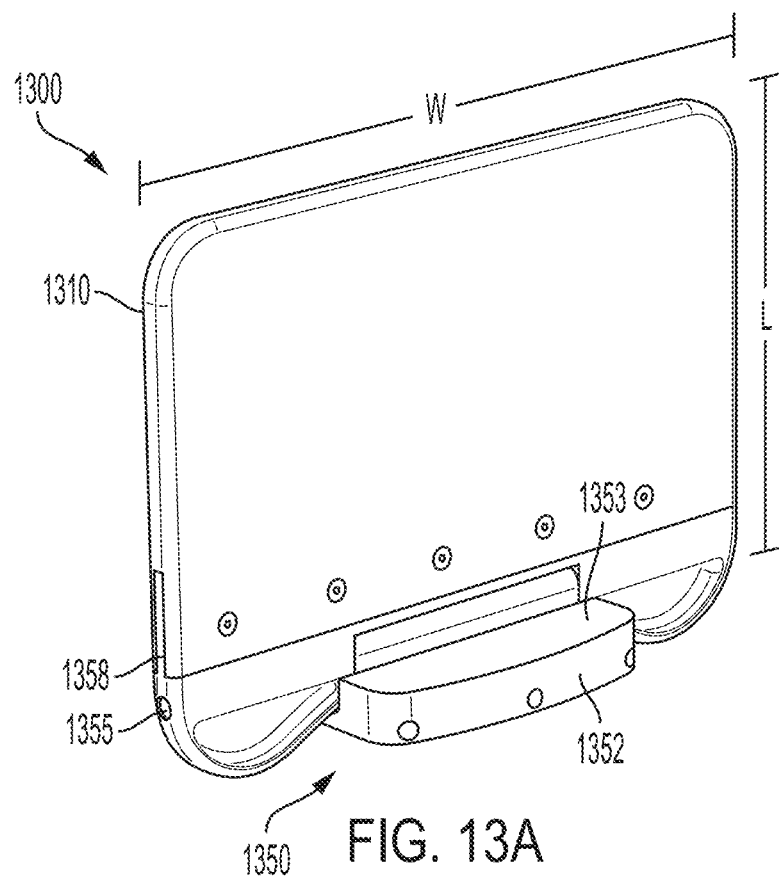
FIG. 13A illustrates a fold-up bridge shown in a vertical or up position, in accordance with some embodiment.
Figure 13B:
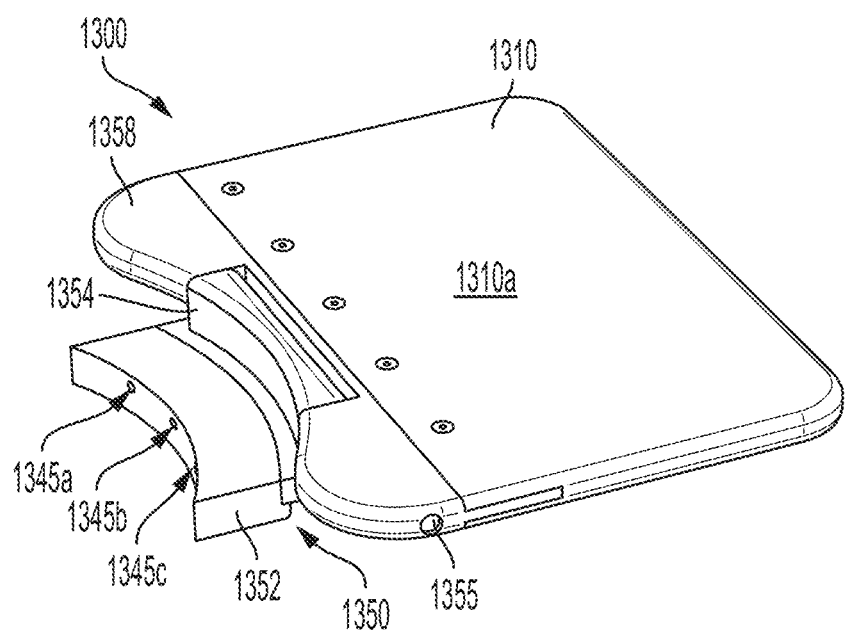
FIG. 13B illustrates the fold-up bridge illustrated in FIG. 13A in a horizontal or down position, in accordance with some embodiments.

FIGS. 13A and 13B illustrate an exemplary fold-out bridge for supporting a patient during positioning and imaging, in accordance with some embodiments. Bridge 1300 is configured to be placed in a stowed or "folded-up" position (also referred to simply as the "up" or "vertical" position) or placed in an operational or "folded-down" position (also referred to simply as the "down" or "horizontal" position), respectively. Bridge 1300 includes a support 1310 configured to bridge a gap between the MRI system to which the bridge is attached and, for example, a hospital bed to which the MRI system is proximately located. Support 1310 comprises a surface 1310a designed to support the patient during positioning and imaging when the bridge is placed in the down position shown in FIG. 13B.

When bridge 1300 is in the down position, surface 1310a of support 1310 is substantially horizontal to provide support for the patient. Support 1310, and particularly surface 1310a, may be made of material that reduces friction between a patient and the bridge, such as a smooth plastic, to facilitate positioning of the patient within the imaging region of the MRI system without producing eddy currents during operation of the system. As shown in FIG. 13A, when bridge 1300 is in the up position, surface 1310a (which is visible in FIG. 13B) of support 1310 is substantially vertical so that the support does not add substantially, if at all, to the dimensions of the magnetic resonance imaging system (e.g., when the bridge is in the up position, the bridge does not increase the outer perimeter or footprint of the system).

Bridge 1300 comprises a hinge 1350 that allows support 1310 to pivot from the up position to the down position and vice versa (e.g., hinge 1350 allows bridge 1300 to be moved between the positions illustrated in FIGS. 13A and 13B). According to some embodiments, hinge 1350 comprises a shaft 1355 that allows support 1310 to pivot or rotate from the vertical position shown in FIG. 13A to the horizontal position shown in FIG. 13B and vice versa. Specifically, exemplary bridge 1300 comprises a base 1352 and a pivot portion 1358 through which shaft 1355 passes to allow the pivot portion 1358 to rotate about the shaft when folding up and folding down the bridge. Base 1352 is configured to attach to the MRI system and includes stop 1353 (see FIG. 13A) and stop 1354 (see FIG. 13B) that provide end stops to prevent further pivoting of the bridge when the horizontal position and vertical position are reached, respectively.

Figure 17A:
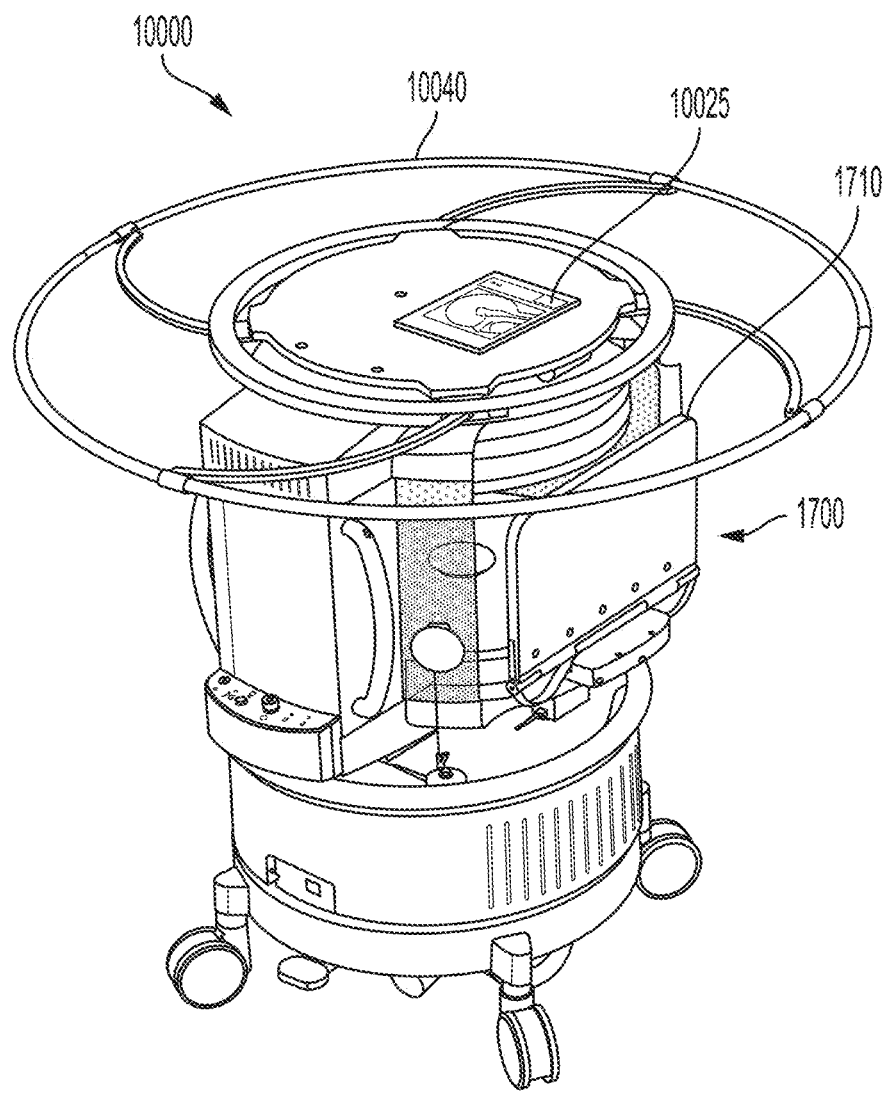
FIG. 17A illustrates a portable MRI system with a bridge in the vertical position.
Figure 17B:
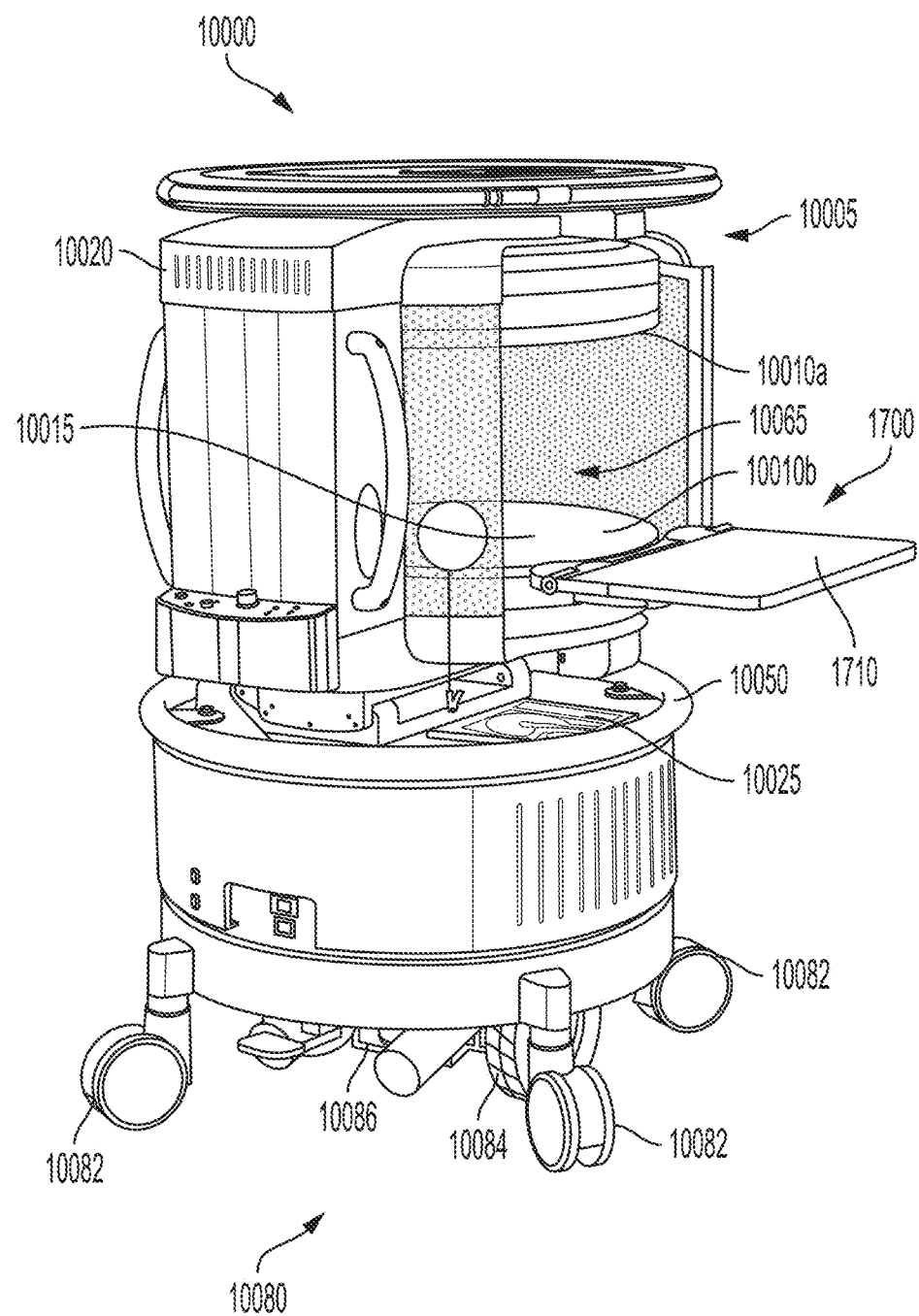
FIG. 17B illustrates a portable MRI system with a bridge in the horizontal position.
Figure 17C:
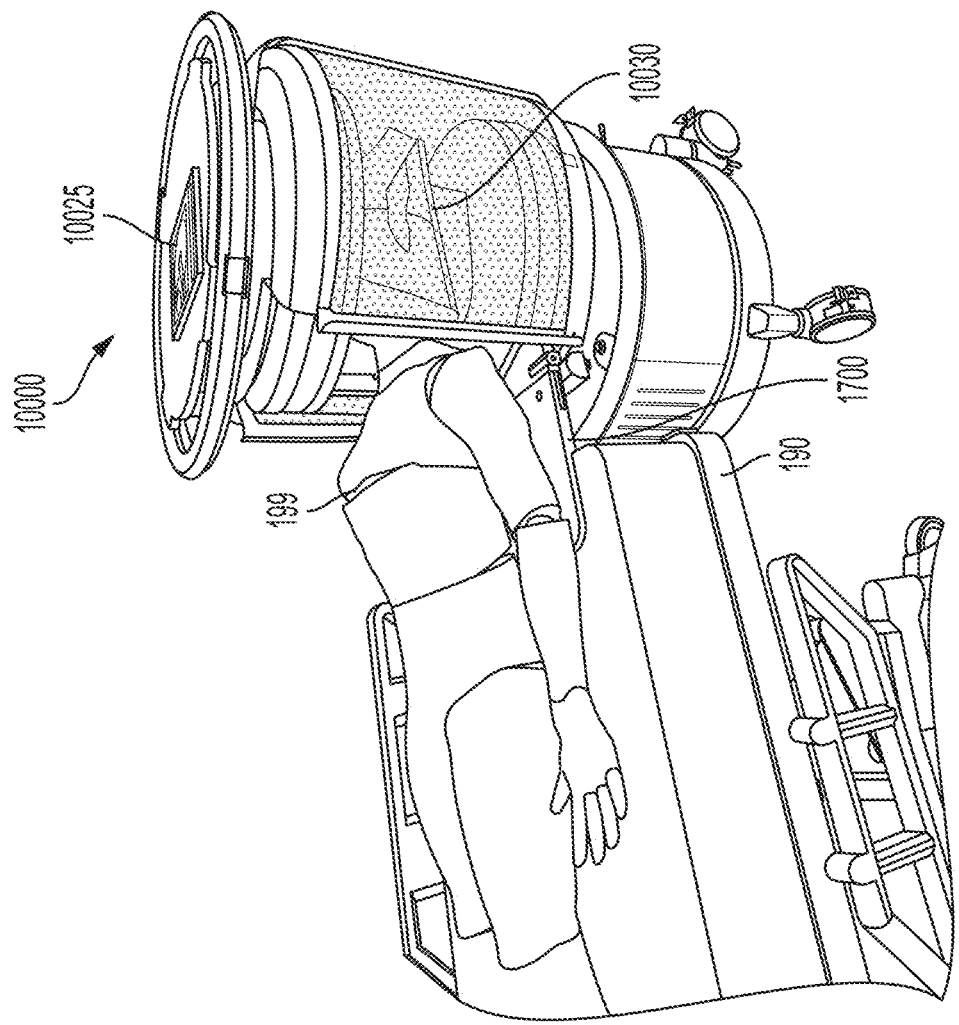
FIG. 17C illustrates a patient positioned within a portable MRI system and supported by a fold-out bridge.

Base 1352 further comprises counter-bores 1345 (e.g., bores 1345*a*, 1345*b* and 1345*c*) to accommodate bolts that allow bridge 1300 to be securely attached to the MRI system. For example, according to some embodiments, base 1352 is constructed with three counter-bores to accommodate respective M8 bolts that securely attach the base of the bridge directly to the B$_0$ magnet of the MRI system (e.g., as shown in FIGS. 17A-17C discussed below). Bolting the bridge to the MRI system in this manner contributes to the bridge being able to withstand the torque produced by the weight of a patient.

As discussed above, the inventors have recognized the benefits of providing a bridge that can accommodate larger (e.g., wider) and heavier patients and that can bridge larger gaps between a patient bed and the MRI system and/or that provide additional overlap with the patient bed when placed in the down position. According to some embodiments, a fold-out bridge is constructed having a width of between 12 and 36 inches and a length of between 8 and 24 inches. For example, exemplary bridge 1300 has a width W of at least 24 inches and a length L of at least 12 inches to provide a relatively large surface to accommodate a variety of patients and to bridge a variety of gaps. The length of the bridge refers to the dimension generally in a direction outward from the MRI system. By increasing the length of the bridge, larger gaps can be bridged and/or larger overlaps with a patient bed can be achieved.

The width of the bridge refers to the dimension generally in a direction tangent to the MRI system. By increasing the width of the bridge, wider patients may be more comfortably accommodated and supported. Hospital equipment for acute care is often rated to accommodate patients weighing 500 lbs. (e.g., hospital beds are often rated to support 500 lb. patients). According to some embodiments, bridge 1300 is also rated for 500 lb. patients and may be constructed to have a safety factor of at least 2.5 (i.e., that have a yield strength of at least 2.5 times the rating). According to some embodiments, bridge 1300 is rated for 500 lb. patients and is constructed to have a safety factor of 4.0 or more, examples of which are described in further detail below.

Figure 14:
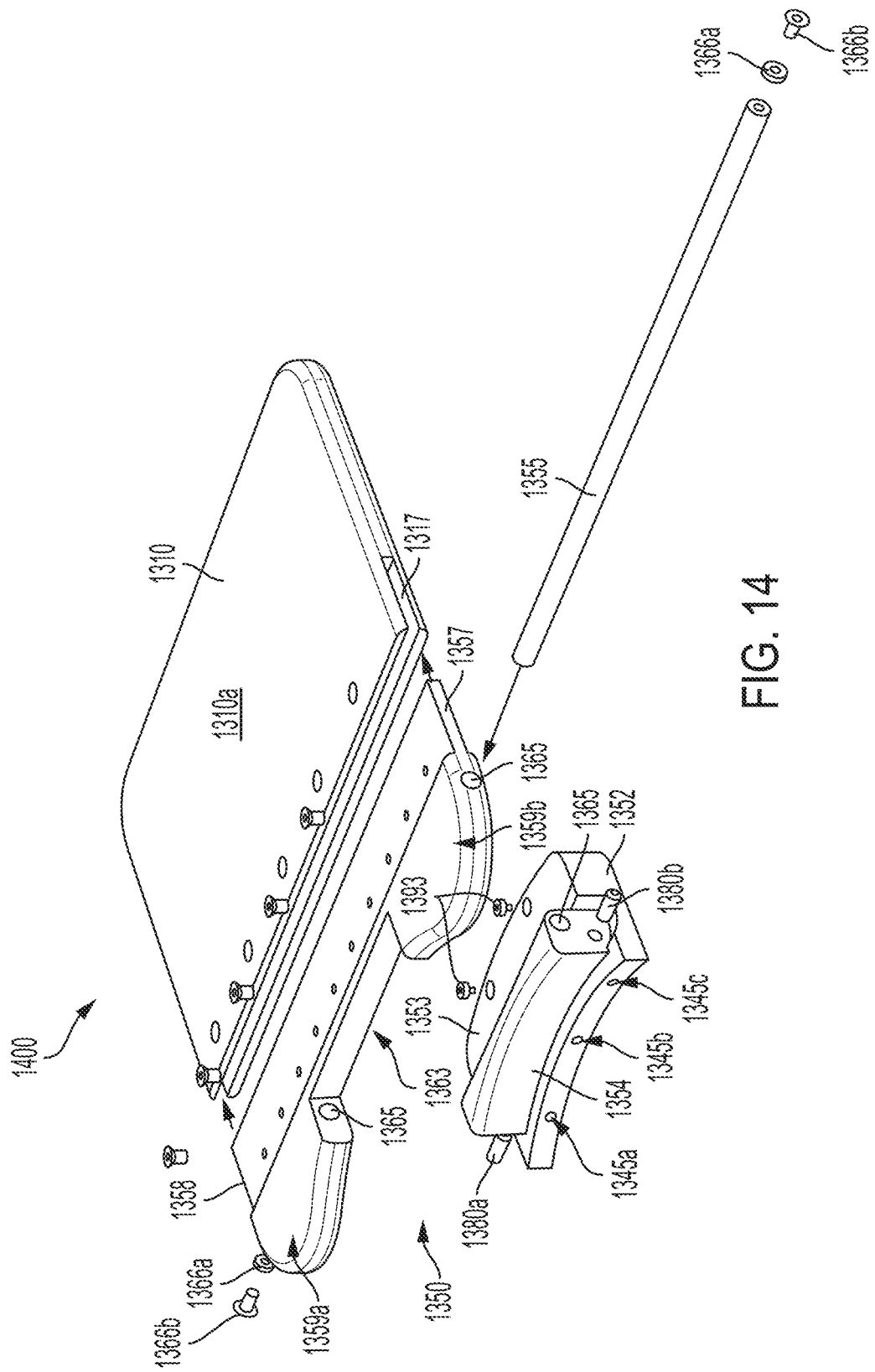
FIG. 14 illustrates components of a fold-up bridge, in accordance with some embodiments.

FIG. 14 illustrates components of a fold-out bridge 1400 to illustrate exemplary construction details, in accordance with some embodiments. Similar to bridge 1300 described above, bridge 1400 includes a support 1310 having a surface 1310*a* configured to support a patient during positioning and imaging. Bridge 1400 further includes a hinge 1350 comprising base 1352 and pivot portion 1358 that, when coupled together via shaft 1355, allows support 1310 to pivot from a vertical position to a horizontal position and vice versa. For exemplary bridge 1400, support 1310 may be coupled to pivot portion 1358 using a tongue-and-groove interface. Specifically, support 1310 includes a groove 1317 configured to receive tongue 1357, which extends out from pivot portion 1358. To couple the support to the pivot portion, tongue 1357 may be inserted into groove 1317 and screwed or bolted into place to secure support 1310 to pivot portion 1358.

To construct hinge 1350, pivot portion 1358 comprises shoulders 1359*a* and 1359*b* between which is provided gap 1363 sized to accommodate base 1352. Shoulders 1359*a*, 1359*b* and stop 1354 of base 1352 include cooperating bores 1365 through which shaft 1355 is inserted to allow support 1310 to pivot between the up and down positions. When constructed, shaft 1355 is secured within bores 1365 of the base and pivot portions with nuts 1366*a* and bolts 1366*b* at both ends of the shaft. Thus, pivot portion 1358 is allowed to rotate about the shaft so that support 1310 can be moved from the vertical position (i.e., in which planar surface 1310*a* is substantially vertical) when not in use to the horizontal position (i.e., in which the planar surface 1310*a* is substantially horizontal) to facilitate positioning a patient within the imaging region of the MRI system and to support the patient during imaging. As discussed above, bridge 1400 can be bolted to the MRI system via bolt holes 1345*a-c* (e.g., bolted to the lower B$_0$ magnet of the MRI system so that it is level with the patient surface within the imaging region of the MRI system as shown in FIGS. 6A-C discussed below).

Bridge 1400 may further include ball plungers 1380*a* and 1380*b* that facilitate holding the bridge in the vertical position when the bridge is not being used. For example, ball or spring plungers 1380*a* and 1380*b* may be positioned on either side of base 1352 to interact with shoulders 1359*a* and 1359*b* of pivot portion 1358. Specifically, to move bridge 1400 from the vertical to the horizontal position, the shoulders of the pivot portion must first overcome the resistance provided by the spring loaded ball plungers (i.e., to pivot bridge 1400 out of the vertical position, shoulders 1359*a* and 1359*b* must first move over the ball plungers, which provide a counter-resistance to the initial rotation of the pivot portion). Accordingly, because an initial force exceeding the resistance of the ball plungers is needed to move the bridge out of the vertical position, a measure of safety is provided by reducing the chances that bridge 1400 will unintentionally fall from the vertical position to the horizontal position. Bridge 1400 may also include rubber stoppers 1393 configured to fit within corresponding holes provided in stop 1353 of base 1352 to reduce noise produced when shoulders 1359*a*, 1359*b* contact stop 1353 when the bridge is moved to the down position and/or to absorb some of the impact of the bridge should the bridge fall or if the bridge is roughly handled during transition to the horizontal position.

Figure 15A:
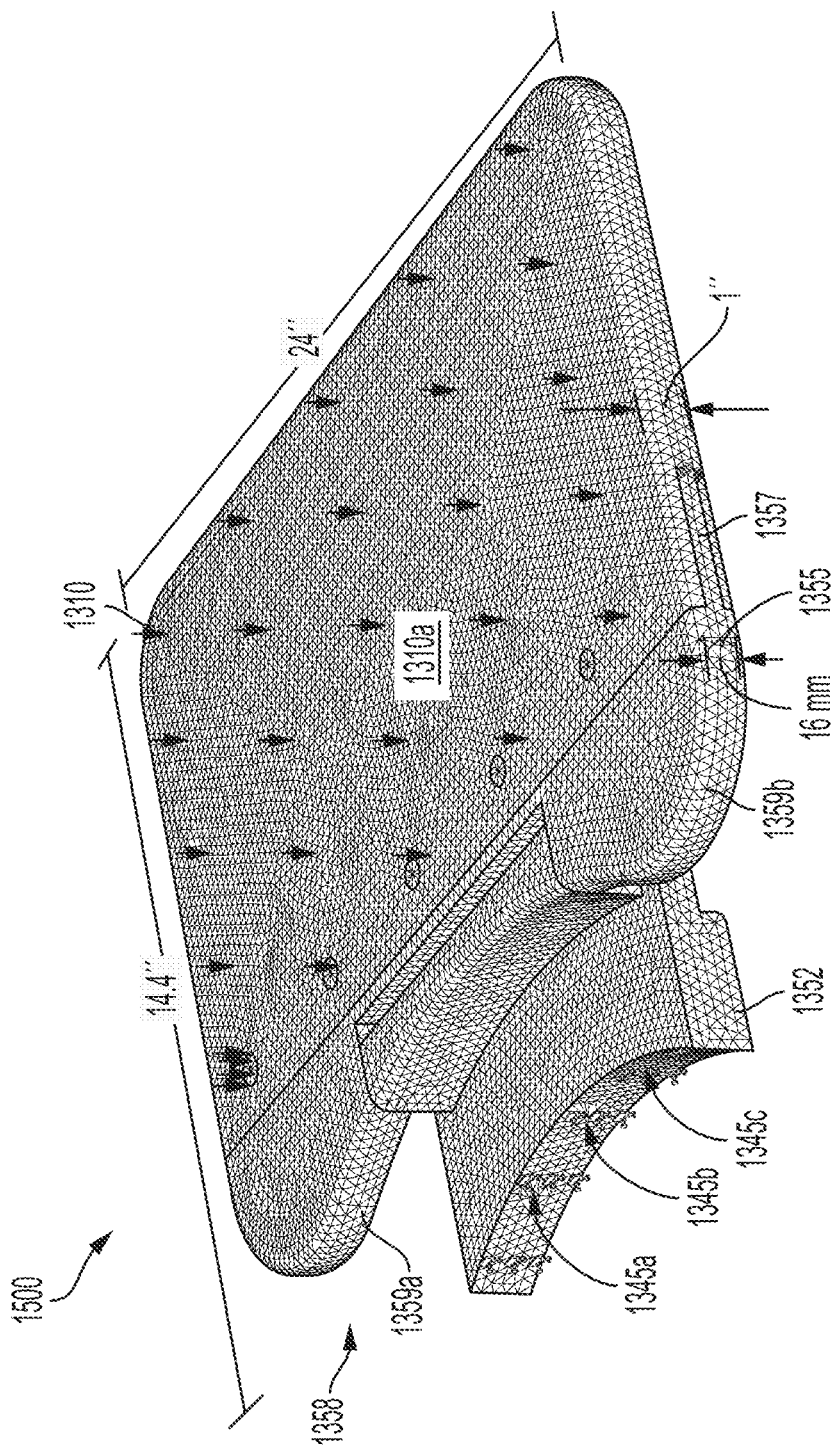
FIG. 15A illustrates a model of a bridge, in accordance with some embodiments.

FIG. 15A illustrates a model of a fold-out bridge 1500 constructed to support larger and/or heavier patients, in accordance with some embodiments. The model illustrated in FIG. 15A was used to perform a number of performance tests on exemplary bridge 1500 designed to provide a relatively large surface to facilitate patient positioning and constructed to support heavier patients (e.g., to achieve a 500 lb. rating). The following dimensions, materials and construction details are provided merely as description of exemplary bridge 1500 on which stress tests were performed and do not limit the aspects of a fold-out bridge in this respect. In particular, different dimensions, materials and designs may be used to construct a fold-out bridge and different aspects of a fold-out bridge discussed herein may be used in different combinations. Bridge 1500 merely illustrates one example of a suitable fold-out bridge capable of supporting larger and/or heavirt patients and that provides a relatively large surface to facilitate patient positioning and support.

Bridge 1500 is provided with a support 1310 having a relatively large surface area, for example, a width of 24 inches and a length of 14.4 inches measured from the far side of support 1310 to the center of the curved interface of base 1352 where bridge 1500 is bolted to the MRI system (i.e., at counter-bore 1345*b*). Support 1310 is formed, at least in part, by a 1 inch thick plastic platform that provides a surface 1310*a* over which a patient can be moved to position the patient within the MRI system. Similar to the construction of exemplary bridge 1400, pivot portion 1358 is coupled to support 1310 via a tongue-and-groove interface and coupled to the base via a 16 mm diameter shaft 1355 inserted through shoulder portions 1359*a* and 1359*b*. For exemplary bridge 1500, shoulders 1359*a* and 1359*b* are constructed of metal (e.g., aluminum) and tongue portion 1357 is constructed of plastic (or other non-metallic material). Base 1352 for exemplary bridge 1550 is constructed of metal, such as steel, and comprises three counter-bores 1345*a-c* for bolting bridge 1500 to the $B_0$ magnet of the MRI system (e.g., using three corresponding M8 bolts). In this way, components of bridge 1500 that undergo the greatest amount of stress may be constructed of metal and components that undergo less stress may be made of plastic (or other non-metallic material) to minimize eddy current production when the MRI system is operated, while providing a bridge with a robust construction.

To evaluate the performance of exemplary bridge 1500, stress tests were simulated on the model of bridge 1500 to ensure that the design achieves a 500 lb. rating with a safety factor suitable for patient support equipment. In particular, using the above described construction details, a mesh was applied to the model of bridge 1500 as shown in FIG. 15A and the stresses resulting from the weight of a patient were simulated via finite element analysis. The weight that bridge 1500 is required to support for a 500 lb. patient was obtained from the International Electrotechnical Commission (IEC) 60601-1 International Standard. Specifically, IEC 60601-1 establishes a number of safety requirements and performance standards for medical equipment.

Figure 15B:
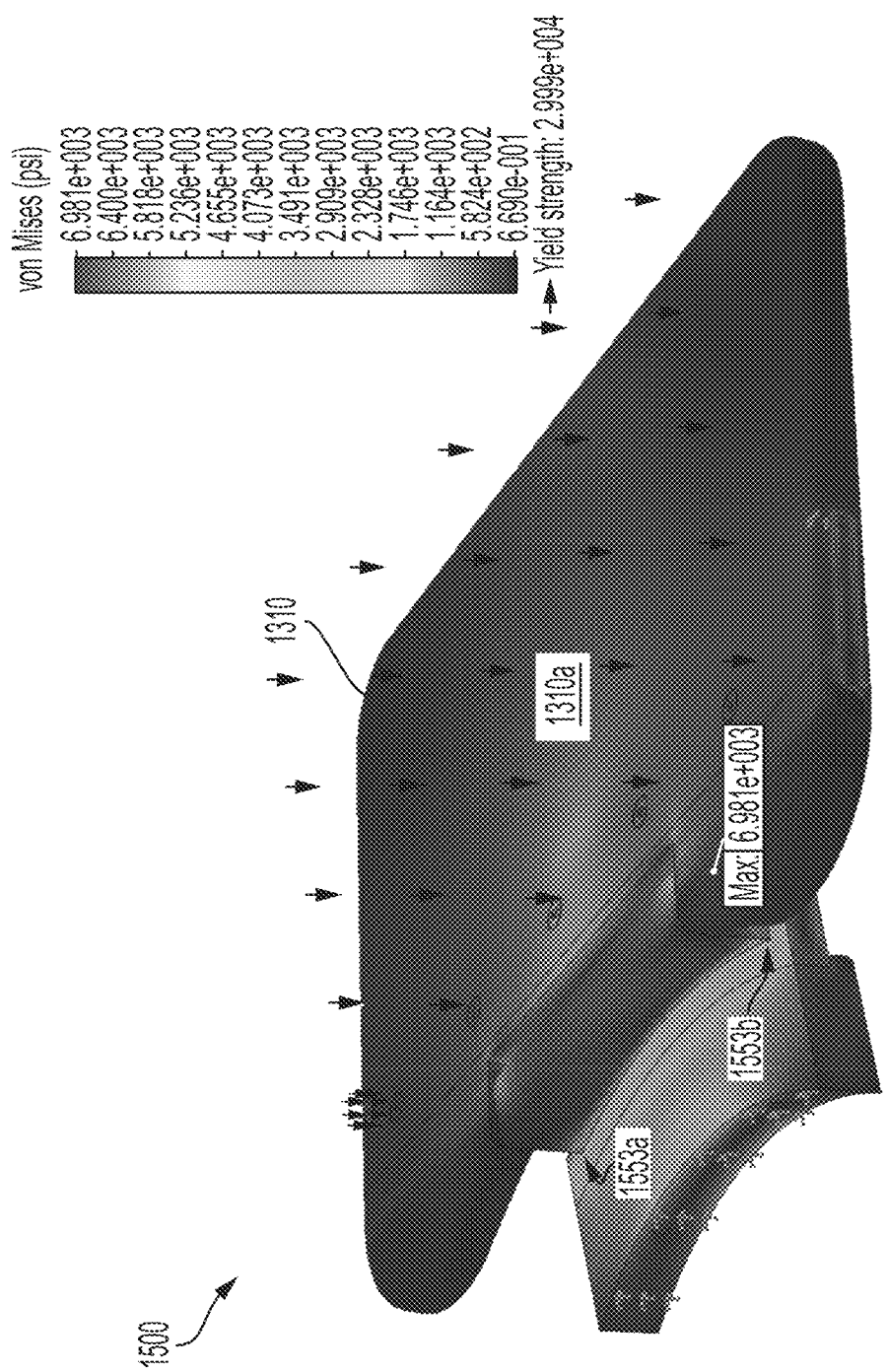
FIG. 15B illustrates a stress plot of the model of the bridge illustrated in FIG. 15A.
Figure 15C:
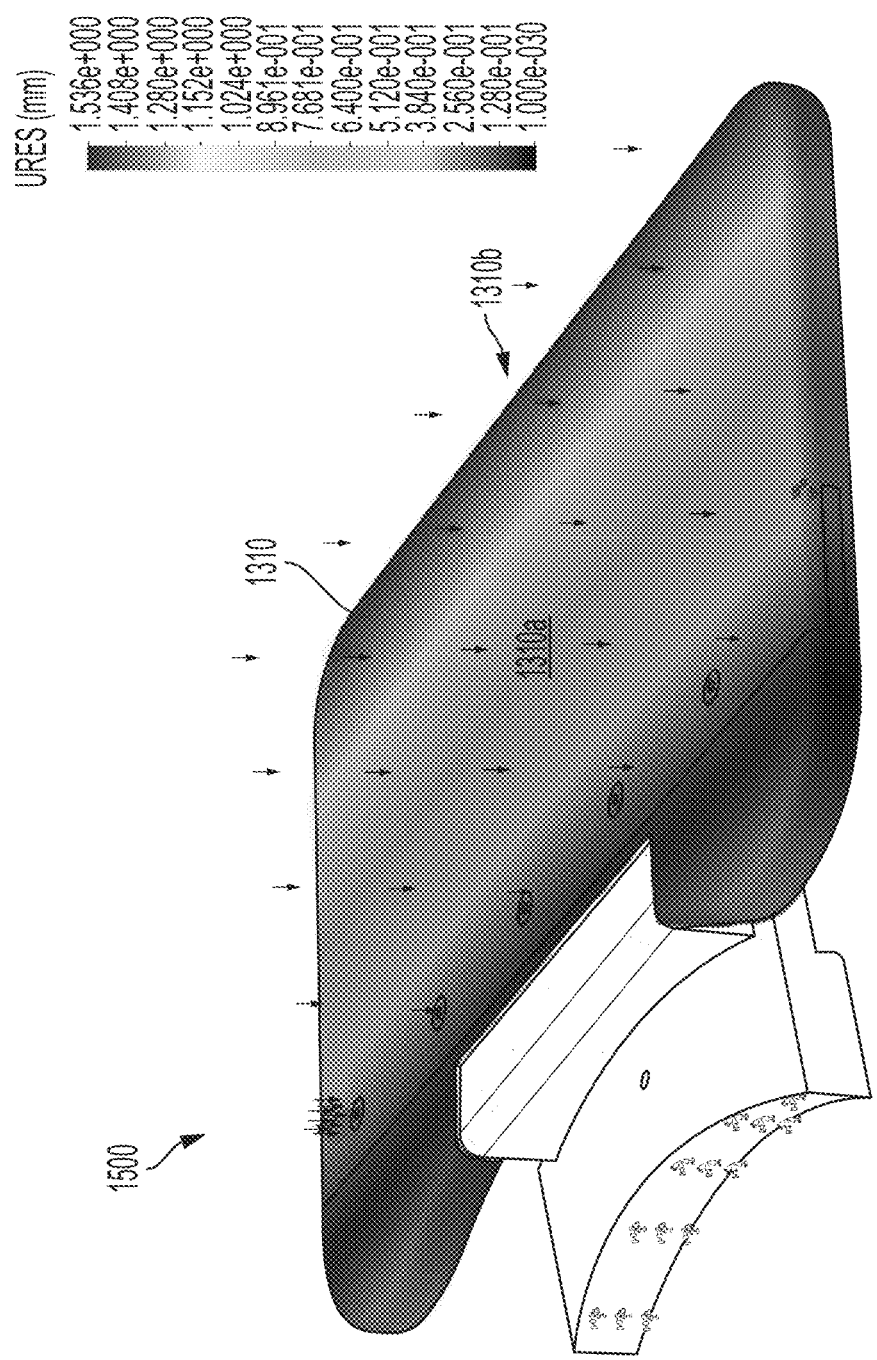
FIG. 15C illustrates a deflection plot of the model of the bridge illustrated in FIG. 15A.
Figure 15D:
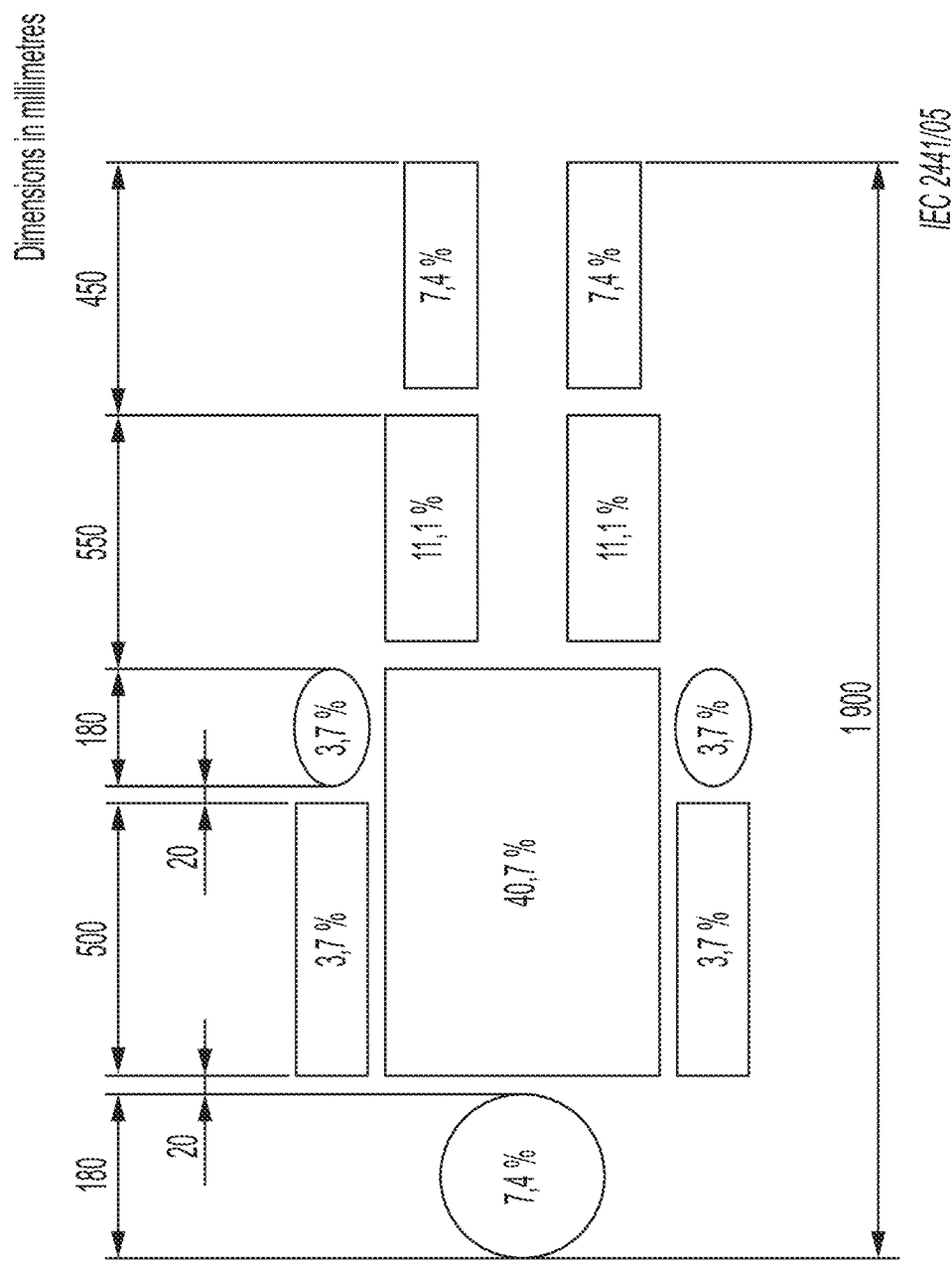
FIG. 15D is Figure A.19 from the IEC 60601-1 illustrating the human body mass distribution for patient support surfaces.

Figure A.19 of IEC 60601-1, which is reproduced herein as FIG. 15D, shows an example of human body mass distribution that was used to determine how the weight of a 500 lb. patient is distributed over the patient support surface of the exemplary bridges described herein. As shown in FIG. 15D, Figure A.19 of IEC 60601-1 specifies the length dimension (in millimeters) and the percent of a patient's body mass that is contributed by significant segments of the human body lying in a supine position. Specifically, the head accounts for 7.4% of the mass of the patient, the torso accounts for 40.7%, the upper arms together account for 7.4% and the lower arms another 7.4%, the upper legs account for 22.2% and the lower legs account for 14.8%. When a patient is positioned within a portable MRI system, the head lies within the imaging region and is supported by the MRI system (e.g., by the helmet on which the transmit/receive coils are located) so that the bridge need support at least some portion of the torso, shoulder and arm portions of the body. The full contribution of the torso and the upper arms is approximately 50% (48.1%) of the body mass of the patient. Accordingly, in approximate numbers, for a bridge having a 500 lb. rating and a safety factor of 1, the bridge would be required to support 250 lbs. (i.e., 50% of the patient's total weight). For a safety factor of 2.5, the bridge would need to support 625 lbs (i.e., 50% of the patient's weight times 2.5) and, for a safety factor of 4, the bridge would need to support 1000 lbs. (i.e., 50% of the patients weight times 4).

To evaluate bridge 1500 for a 500 lb. rating, the stresses on bridge 1500 resulting from a 500 lb. patient were simulated by distributing 250 lbs. of weight over the surface of the bridge (i.e., 50% of the patient's weight that the bridge needs to support), as shown by the downward arrows in FIGS. 15A-15C. Using the materials and dimensions discussed above, this distributed weight produced the stress plot shown in FIG. 15B. A maximum stress of 6,981 psi resulted at the corners of the base indicated by arrows 1553*a* and 1553*b*. The yield strength of exemplary bridge 1500 was also assessed to evaluate the maximum stress that bridge 1500 can withstand. The yield strength of bridge 1500 was determined to be 30,000 psi. Thus, exemplary bridge 1500 achieves a 500 lb. rating with a safety factor of 4.3. Specifically, the yield strength of the bridge is 4.3 times greater than the maximum stress resulting from simulating the forces applied on bridge 1500 by a 500 lb. patient.

FIG. 15C illustrates a deflection plot showing the deformation of the bridge under the 250 lb. simulated weight. The maximum deflection of the bridge resulting from the simulation was 1.5 mm at the far end of support 1310. In particular, the arrows show the location of the bridge without the simulated force applied. In FIGS. 15B and 15C, the displacement resulting from the applied 250 lbs. is shown at 36.4 scale to exaggerate the displacement so that it can be visualized (i.e., the actual displacement is 36.4 times smaller than it appears in the plots shown in FIGS. 15B and 15C.). Thus, a 250 lb. weight distributed across bridge 1500 to simulate the stresses resulting from a 500 lb. patient resulted in a maximum displacement of 1.5 mm at end 1310*b* of support 1310.

The inventors have recognized that some embodiments of a fold-out bridge may be relatively large and heavy, particularly when dimensioned and constructed to facilitate positioning and support of larger, heavier patients. For example, an exemplary bridge may be dimensioned to have a length of between 1 and 2 feet or more and a width of between 1.5 and 2.5 feet or more, resulting in bridges that can weigh between 8 and 15 lbs. or more. Larger, heavier bridges have the potential to injure if the bridge accidentally falls from the vertical position. To prevent a bridge from being able to free fall, the inventors have developed a counter-balance mechanism configured to slow the rate at which the bridge can transition from the up position to the down position. The counter-balance mechanism provides an additional safety precaution that protects patients and medical personnel from possible injury, as discussed in further detail below.

Figure 16B:
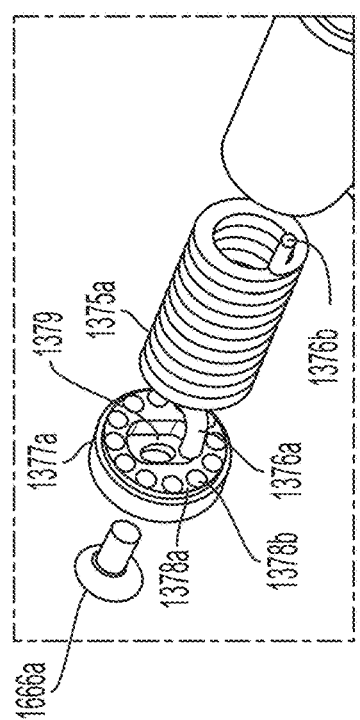
FIGS. 16A and 16B illustrate components of a fold-up bridge with a counter-balance mechanism, in accordance with some embodiments.
Figure 16A:
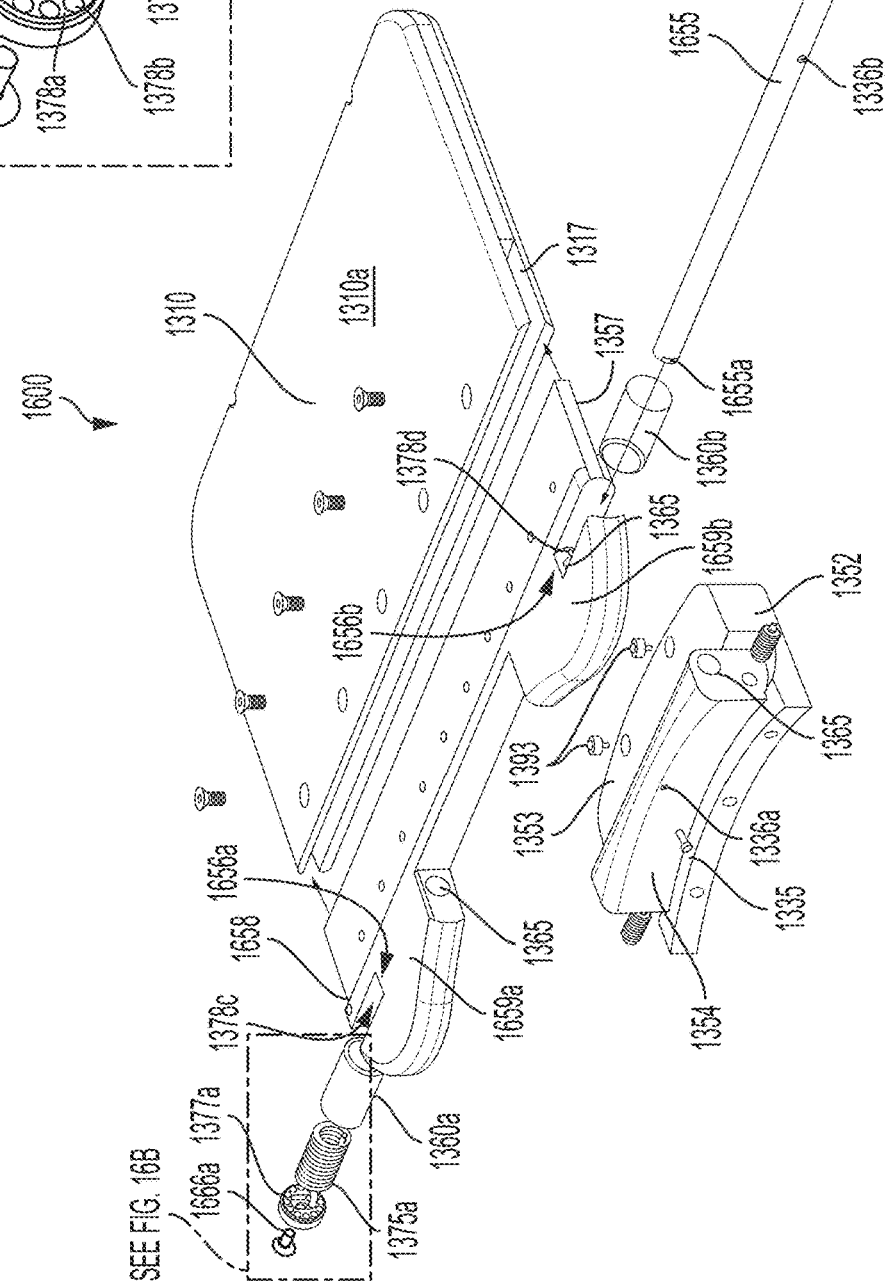

FIGS. 16A and 16B illustrate components for a bridge 1600, in accordance with some embodiments. Exemplary fold-out bridge 1600 may comprise many of the same components described in connection with bridge 1400 illustrated in FIG. 14 and/or bridge 1500 illustrated in FIGS. 15A-C. However, bridge 1600 includes a counter-balance mechanism configured to slow the rate at which fold-out bridge 1600 can pivot to the horizontal position. According to some embodiments, the counter-balance mechanism comprises torsion springs 1375*a* and 1375*b*. Torsion springs 1375*a* and 1375*b* are configured to fit over respective ends of shaft 1655. Each torsion spring 1375*a*, 1375*b* is configured with end portions 1376*a* and 1376*b* that protrude out from the spring in the direction of the shaft's longitudinal axis, as can be seen best in the magnified portion of one end of the counter-balance component illustrated in FIG. 16B.

In particular, end portions 1376a are arranged in the direction of the axis of shaft 1655 and positioned on the perimeter of the respective torsion spring and are configured to fit into a corresponding indexing hole 1378 provided in indexing components 1377a, 1377b. End portions 1376b are similarly arranged and configured to fit into respective indexing holes 1378 provided in shoulders 1659a and 1659b of pivot portion 1658. Specifically, indexing components 1377a, 1377b comprise a plurality of indexing holes 1378 around the perimeter (see e.g., exemplary indexing holes 1378a and 1378b illustrated in FIG. 16B) to accommodate end portions 1376a. Shoulders 1659a and 1659b comprise notches 1656a and 1656b to accommodate respective torsion springs. Notches 1656a and 1656b comprise bores 1365 through which shaft 1655 passes and further comprise indexing holes 1378 into which end portions 1376b are inserted (as best seen by indexing hole 1378d provide next to bore 1365 within notch 1656b). For example, end portion 1376b of each torsion spring 1375a, 1375b fits into the respective indexing holes 1378c and 1378d so that the torsion spring is coupled to indexing component 1377 at one end and pivot component 1658 at the other end.

Shaft 1655 includes flats 1655a and 1655b configured to fit into respective indexing components 1377a and 1377b. Specifically, flats 1655a and 1655b are configured to be inserted into slots 1379 provided in respective indexing components 1377a, 1377b (as seen best in the magnified view shown in FIG. 16B) and secured by screws 1666a and 1666b at opposite ends of shaft 1655. To facilitate operation of the counter-balance mechanism, corresponding screw holes 1336a and 1336b are provided through stop 1354 of base 1352 and into shaft 1655, respectively, to accommodate screw 1335 to hold shaft 1355 in place. Specifically, screw 1335 is inserted through screw hole 1336a in the base and into screw hole 1336b in shaft 1655 to prevent the shaft from rotating when pivot portion 1658 rotates during transitions between the up and down positions. Preventing shaft 1355 from rotating ensures that rotation of pivot portion 1658 causes the torsion springs 1375a, 1375b to wind-up or tighten to slow the rate at which pivot portion 1658 can rotate, as discussed in further detail below. Sleeves 1360a and 1360b cover respective torsion springs 1375a and 1375b when the bridge is assembled.

When constructed as described above, shaft 1655 is fixed in place and prevented from rotating by inserting the shaft through bores 1365 and into slots 1379 of the respective indexing portions 1377a, 1377b and screwing the shaft in place via screws 1666a, 1666b and 1335. By inserting end portions 1376a and 1376b of the torsion springs 1375a, 1375b into the indexing portions 1377a, 1377b and pivot portion 1658, respectively, rotation of pivot portion 1658 from the vertical position to the horizontal position causes the torsion springs to tighten due to the fixed connection between end portions 1376a and the indexing components 1377a, 1377b (which does not rotate) and the fixed connection between end portions 1376b and the indexing holes 1378c, 1378d in notches 1656a, 1656b, respectively, by which end portions 1376b are rotated along with the pivot portion 1658. That is, because indexing holes 1378c and 1378d and end portions 1376b are aligned in the direction of the shaft axis but are positioned off-axis, the rotation of the pivot portion causes the torsion spring to tighten as indexing holes 1378c and 1378d rotate about the axis of the shaft. Thus, when the bridge pivots from a vertical to a horizontal position, the twisting of the torsion springs slows the rotation of support 1310 to prevent the bridge from rotating in free fall. The spring constant of the torsion springs can be selected to achieve the desired level of control of the rate at which the bridge is allowed to transition between the up and down positions. In this manner, bridge 1600 includes a counter-balance mechanism providing an additional safety mechanism to reduce the chances of injury when using a fold-out bridge.

As discussed above, the exemplary fold-out bridges described herein are configured to attach to a portable magnetic resonance imaging system to facilitate positioning and supporting a patient during point-of-care MRI. FIGS. 17A, 17B and 17C illustrate a portable low-field MRI system to which the exemplary fold-out bridges described herein can be attached. Specifically, portable low-field MRI system 10000 can be deployed in virtually any environment to image patients, for example, from a standard hospital bed located in emergency rooms, intensive care units, operating rooms, neonatal units, clinics, primary care offices, recovery units, etc. where conventional MRI is typically not available. Exemplary fold-out bridge may be configured to facilitate positioning and support of large, heavy patients without substantially increasing the footprint of the MRI system by virtue of being capable of being stowed in the vertical position during transport or when not in use and folded-down when needed to perform, for example, point-of-care MRI.

In particular, to facilitate transporting portable MRI system 10000 to locations at which MRI is needed, portable MRI system 10000 is equipped with a fold-out bridge 1700, which may include any one or more of the features of a fold-out bridge described herein. FIG. 17A illustrates bridge 1700 configured in its up position so that support 1710 is substantially vertical and does not add significantly (or at all) to the footprint of the MRI system. As a result, bridge 1700 does not impede moving the portable MRI system down hallways and through doorways. FIG. 17A also illustrates a deployable guard 10040 in its deployed position to indicate the 5-Gauss line for the MRI system as its being transported or when it is stored away or otherwise not in use. As discussed in U.S. application Ser. No. 16/389,004, titled "Deployable Guard for Portable Magnetic Resonance Imaging Device," filed on Apr. 19, 2019, and which is herein incorporated by reference in its entirety, the guard can be deployed to demarcate the physical boundary within which the magnetic field is above a specified field strength to provide a visual signal regarding the magnetic field when the MRI system is being moved to a different location. In addition, as illustrated in FIG. 17B, when bridge 1700 is up, the bridge provides a barrier to the imaging region of the MRI system where the magnetic field is strongest.

FIG. 17B illustrates portable MRI system 10000 with bridge 1700 configured in the down position and FIG. 17C illustrates bridge 1700 deployed in the down position to bridge the gap between a patient bed 490 and MRI system 10000 to allow patient 499 to be positioned within the imaging region of the MRI system and to support patient 499 during imaging. As discussed above, bridge 1700 may be bolted to the $B_0$ magnet to secure the bridge to the MRI system. For example, as shown in FIG. 17B, portable MRI system 10000 comprises a $B_0$ magnet 10005 that includes at least one first permanent $B_0$ magnet 10010a and at least one second permanent $B_0$ magnet 10010b magnetically coupled to one another by a ferromagnetic yoke 10020 configured to capture and channel magnetic flux to increase the magnetic flux density within the imaging region 10065 (field of view) of the MRI system. For exemplary MRI system 10000, bridge 1700 is bolted to the lower magnet 10010b so that when it is deployed (i.e., positioned in the down position as shown in FIGS. 17B and 17C), support 1710 provides a continuation of the planar surface 10015 of the magnet housing to facilitate positioning the patient within imaging region 10065 and providing relatively level support to the patient during imaging. FIG. 17B also illustrates a conveyance mechanism 10080 of MRI system 10000 that facilitates moving the MRI system from one location to another, as discussed in further detail below.

FIG. 17C illustrates patient 499 positioned within the imaging region of MRI system 1000 for imaging of the patient's head from hospital bed 490. As shown, once the patient is positioned with the imaging region and during the imaging process, the patient's head is supported by helmet 10030 (which comprises radio frequency transmit and receive coils), at least a portion of the patient's torso and arms are supported by fold-out bridge 1700 and the remainder of the patient's weight is supported by patient bed 490. As discussed above, some embodiments of a fold-out bridge are dimensioned and constructed to support large and heavy patients. For example, bridge 1700 may be rated for a 500 lb. patient with a safety factor of 2.5 or more. According to some embodiments, bridge 1700 may be rated for a 500 lb. patient with a safety factor of 4.0 or more (e.g., a safety factor of 4.3), for example, using the various exemplary bridge constructions described above in connection with any of exemplary bridges 1400, 1500 or 1600.

As discussed above, portable MRI system 10000 includes a conveyance mechanism configured to allow the portable MRI system to be transported to desired locations. Referring to FIG. 17B, portable MRI system 10000 comprises a conveyance mechanism 10080 having a drive motor 10086 coupled to drive wheels 10084. Conveyance mechanism 10080 may also include a plurality of castors 1082 to assist with support and stability as well as to facilitate transport of the MRI system. In this manner, conveyance mechanism 10080 provides motorized assistance in transporting MRI system 10000 to desired locations.

According to some embodiments, conveyance mechanism 10080 includes motorized assistance controlled using a controller (e.g., a joystick or other controller that can be manipulated by a person) to guide the portable MRI system during transportation to desired locations. According to some embodiments, the conveyance mechanism comprises power assist means configured to detect when force is applied to the MRI system and to engage the conveyance mechanism to provide motorized assistance in the direction of the detected force. For example, rail 10050 illustrated in FIG. 17B may be configured to detect when force is applied to the rail (e.g., by personnel pushing on the rail) and engage the drive motor to provide motorized assistance to drive the wheels in the direction of the applied force. As a result, a user can guide the portable MRI system with the assistance of the conveyance mechanism that responds to the direction of force applied by the user. The drive motor may be operated in other ways, such as via buttons, roller ball or other suitable mechanism located on the MRI system, or using touch screen controls on a mobile computing device 10025 communicatively coupled to the MRI system, as the aspects of motorized control is not limited in this respect.

Thus, low-field MRI system 10000 equipped with fold-out bridge 1700 can be used to perform point-of-care MRI on a patient, including large and heavy patients. For example, to perform point-of-care MRI on a patient from a standard medical bed, the MRI system and the bed can be positioned proximate one another. In some embodiments, the MRI system is portable and can be moved into position near the hospital bed by medical personnel pushing the MRI system into place and/or using a motor drive conveyance system to move the MRI system into position. In some instances, the MRI system may need to be transported from another room or unit within the hospital. In other instances, the MRI system may already be located in the same room as the patient and need only be moved next to the bed of the patient. In other circumstances, a hospital bed is transported to the MRI system and moved into place proximate the MRI system for imaging. During the positioning of the MRI system and the patient bed near one another, a fold-out bridge attached to the MRI system may be positioned in the vertical or up position (e.g., in the vertical position illustrated in FIG. 17A) to facilitate transport of the system down hallways and/or through doorways and/or to facilitate positioning the MRI system and the bed in close proximity (e.g., positioning the MRI system and the foot or head of the bed adjacent one another).

Once the MRI system and the bed are positioned proximate one another, the fold-out bridge may be moved from the vertical position to a horizontal position so that the bridge at least partially overlaps the bed (e.g., the fold-out bridge 1700 may be moved from the vertical position illustrated in FIG. 17A to the horizontal position illustrated in FIGS. 17B and 17C). The fold-out bridge then provides a surface that bridges the gap between the MRI system and the bed over which the patient can be moved. For example, the portion of anatomy of the patient to be imaged may be positioned within an imaging region of the MRI system via the bridge and the bridge may provide support for the patient during and after positioning the patient within the imaging region. After positioning the patient within the MRI system, at least one magnetic resonance image of the portion of the anatomy of the patient may be acquired while the patient is at least partially supported by the bed and at least partially support by the bridge (e.g., as shown in FIG. 17C). In this way, point-of-care MRI may be performed.

Having thus described several aspects and embodiments of the technology set forth in the disclosure, it is to be appreciated that various alterations, modifications, and improvements will readily occur to those skilled in the art. Such alterations, modifications, and improvements are intended to be within the spirit and scope of the technology described herein. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

The above-described embodiments can be implemented in any of numerous ways. One or more aspects and embodiments of the present disclosure involving the performance of processes or methods may utilize program instructions executable by a device (e.g., a computer, a processor, or other device) to perform, or control performance of, the processes or methods. In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above. The computer readable medium or media can be transportable, such that the program or programs stored thereon can be loaded onto one or more different computers or other processors to implement various ones of the aspects described above. In some embodiments, computer readable media may be non-transitory media.

The terms "program" or "software" are used herein in a generic sense to refer to any type of computer code or set of computer-executable instructions that can be employed to program a computer or other processor to implement various aspects as described above. Additionally, it should be appreciated that according to one aspect, one or more computer programs that when executed perform methods of the present disclosure need not reside on a single computer or processor, but may be distributed in a modular fashion among a number of different computers or processors to implement various aspects of the present disclosure.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as a controller that controls the above-discussed function. A controller can be implemented in numerous ways, such as with dedicated hardware, or with general purpose hardware (e.g., one or more processor) that is programmed using microcode or software to perform the functions recited above, and may be implemented in a combination of ways when the controller corresponds to multiple components of a system.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smartphone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible formats.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

What is claimed is:

1. A system configured to perform magnetic resonance imaging of a patient's head, the system comprising:
   a magnetic resonance imaging (MRI) device for performing the magnetic resonance imaging of the patient's head, the MRI device comprising at least one $B_0$ magnet configured to generate a $B_0$ magnetic field for the MRI device;
   a member attached to the MRI device; and
   a helmet configured to accommodate the patient's head during the magnetic resonance imaging, the helmet comprising:
      at least one radio frequency transmit and/or receive coil; and
      at least one first releasable securing mechanism configured to engage with the member attached to the MRI device such that when the at least one first releasable securing mechanism engages with the member, the helmet is positioned within an imaging region of the MRI device.

2. The system of claim 1, wherein the at least one first releasable securing mechanism comprises:
   a receptacle dimensioned to accommodate the member; and
   a retention portion configured to resist movement of the member once the member has been positioned within the receptacle.

3. The system of claim 2, wherein the retention portion comprises a first arm portion and a second arm portion, each forming at least a portion of the receptacle, wherein the first arm portion comprises a first protrusion and the second arm portion comprises a second protrusion, and wherein the first protrusion and the second protrusion are configured to impede the member from entering and exiting the receptacle, such that force on the first protrusion and the second protrusion is needed to allow the member to enter and exit the receptacle.

4. The system of claim 3, wherein the first protrusion and the second protrusion are configured such that a first force required to allow the member to enter the receptacle is less than a second force required to allow the member to exit the receptacle.

5. The system of claim 1, wherein the first releasable securing mechanism allows rotation of the helmet about the member.

6. The system of claim 1, wherein the MRI device is a low-field MRI device and the $B_0$ magnet is configured to generate a $B_0$ field of 0.2 Tesla (T) or less and greater than or equal to 20 mT.

7. The system of claim 6, wherein the MRI device is a low-field MRI device and the $B_0$ magnet is configured to generate a $B_0$ field of 0.1 T or less and greater than or equal to 50 mT.

8. The system of claim 1, wherein the MRI device is a portable MRI device comprising a base and a conveyance mechanism coupled to the base for transporting the portable MRI device.

9. A method for performing magnetic resonance imaging of a patient's head, the method comprising:
   securing a helmet configured to accommodate the patient's head during magnetic resonance imaging to a magnetic resonance imaging (MRI) device, wherein the helmet comprises at least one radio frequency transmit and/or receive coil and wherein securing the helmet comprises:
      engaging at least one first releasable securing mechanism of the helmet with a member attached to the MRI device such that the helmet is positioned within an imaging region of the MRI device; and
   imaging the patient's head using the at least one radio frequency transmit and/or receive coil.

10. The method of claim 9, further comprising releasing the helmet from the member at least in part by releasing the at least one first releasable securing mechanism from the member.

11. The method of claim 9, further comprising, subsequent to engaging the at least one first releasable securing mechanism of the helmet with the member attached to the MRI device, positioning the patient's head in the helmet.

12. The method of claim 9, wherein engaging the at least one first releasable securing mechanism of the helmet with the member attached to the MRI device comprises positioning the member within a receptacle of the at least one first releasable securing mechanism, wherein the at least one first releasable securing mechanism further comprises a retention portion configured to resist movement of the member once the member has been positioned within the receptacle.

13. The method of claim 12, wherein the retention portion comprises a first arm portion and a second arm portion, each forming at least a portion of the receptacle, wherein the first arm portion comprises a first protrusion and the second arm portion comprises a second protrusion, and wherein the first protrusion and the second protrusion are configured to impede the member from entering and exiting the receptacle, such that force on the first protrusion and the second protrusion is needed to allow the member to enter and exit the receptacle.

14. The method of claim 9, further comprising engaging at least one second releasable securing mechanism of the helmet with at least one recess of the member attached to the MRI device, wherein the at least one second releasable securing mechanism is configured to prevent rotation of the helmet about the member when the at least one second releasable securing mechanism engages with the at least one recess.

15. A method for performing magnetic resonance imaging of a patient's head, the method comprising:
   securing a helmet configured to accommodate the patient's head during magnetic resonance imaging to a magnetic resonance imaging (MRI) device, wherein the helmet comprises at least one radio frequency transmit and/or receive coil and wherein securing the helmet comprises:

engaging at least one first releasable securing mechanism of the helmet with a member attached to the MRI device such that the at least one first releasable securing mechanism resists translation of the helmet relative to the member, but permits rotation about the member; and engaging at least one second releasable securing mechanism with a cooperating portion of the member attached to the MRI device such that the at least one second releasable securing mechanism prevents rotation of the helmet about the member; and imaging the patient's head using the at least one radio frequency transmit and/or receive coil.

16. The method of claim 15, further comprising releasing the helmet from the member at least in part by releasing the at least one first releasable securing mechanism from the member and releasing the at least one second releasable securing mechanism from the cooperating member.

17. The method of claim 15, further comprising, subsequent to engaging the at least one first releasable securing mechanism of the helmet with the member attached to the MRI device and engaging the at least one second releasable securing mechanism with the cooperating portion of the member attached to the MRI device, positioning the patient's head in the helmet.

18. The method of claim 15, wherein engaging the at least one first releasable securing mechanism of the helmet with the member attached to the MRI device comprises positioning the member within a receptacle of the at least one first releasable securing mechanism, wherein the at least one first releasable securing mechanism further comprises a retention portion configured to resist movement of the member once the member has been positioned within the receptacle.

19. The method of claim 15, wherein engaging the at least one second releasable securing mechanism of the helmet with the cooperating portion of the member comprises engaging the at least one second releasable securing mechanism with at least one recess of the cooperating member, wherein the at least one recess is configured to prevent rotation of the helmet about the member when the at least one second releasable securing mechanism engages with the at least one recess.

20. The method of claim 19, wherein engaging the at least one second releasable securing mechanism of the helmet with the cooperating portion of the member further comprises fitting a pin of the at least one second releasable securing mechanism within at least one notch of the recess.

* * * * *